(12) United States Patent
Mevellec et al.

(10) Patent No.: US 10,342,795 B2
(45) Date of Patent: Jul. 9, 2019

(54) SUBSTITUTED 4,5,6,7-TETRAHYDRO-PYRAZOLO[1,5-A]PYRIMIDINE DERIVATIVES AND 2,3-DIHYDRO-1H-IMIDAZO[1,2-B]PYRAZOLE DERIVATIVES AS ROS1 INHIBITORS

(71) Applicant: Janssen Pharmaceutica NV, Beerse (BE)

(72) Inventors: Laurence Anne Mevellec, Louviers (FR); Matthieu Ludovic Jeanty, Louviers (FR); Thierry Francois Alain Jean Jousseaume, Beringen (CH)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/129,618

(22) PCT Filed: Mar. 26, 2015

(86) PCT No.: PCT/EP2015/056501
§ 371 (c)(1),
(2) Date: Sep. 27, 2016

(87) PCT Pub. No.: WO2015/144801
PCT Pub. Date: Oct. 1, 2015

(65) Prior Publication Data
US 2017/0173014 A1   Jun. 22, 2017

(30) Foreign Application Priority Data

Mar. 27, 2014   (EP) .................................... 14161959

(51) Int. Cl.
*A61K 31/506* (2006.01)
*C07D 471/04* (2006.01)
(Continued)

(52) U.S. Cl.
CPC ........ *A61K 31/506* (2013.01); *A61K 31/4409* (2013.01); *A61K 31/519* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | | |
|---|---|---|---|---|
| 5,624,931 A * | 4/1997 | Oku | ...................... | C07D 487/04 514/233.2 |
| 2006/0079536 A1 | 4/2006 | Yasuma et al. | | |
| 2010/0029657 A1 * | 2/2010 | Levin | ................... | C07D 519/00 514/249 |

FOREIGN PATENT DOCUMENTS

| | | |
|---|---|---|
| EP | 1505068 A1 | 2/2005 |
| WO | WO 2004/058176 A2 | 7/2004 |

(Continued)

OTHER PUBLICATIONS

Davies et al., Molecular Pathways: ROS1 Fusion Proteins in Cancer. Clinical Cancer Research, 2013, 19, 4040-4045.*

(Continued)

*Primary Examiner* — Po-Chih Chen

(57) ABSTRACT

The present invention relates to substituted 4,5,6,7-tetra-hydro-pyrazolo[1,5-a]pyrimidine derivatives and 2,3-di-hydro-1H-imidazo[1,2-b]pyrazole derivatives of formula (I)

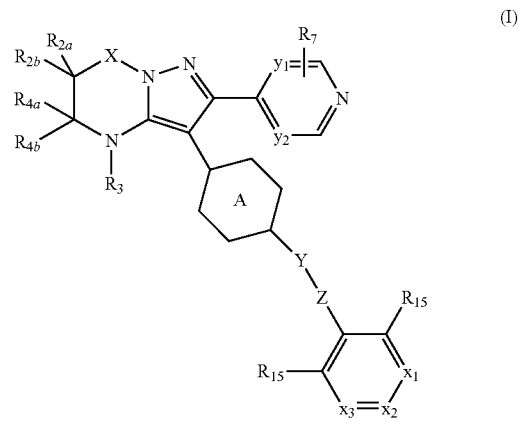

and also compounds of formula (I')

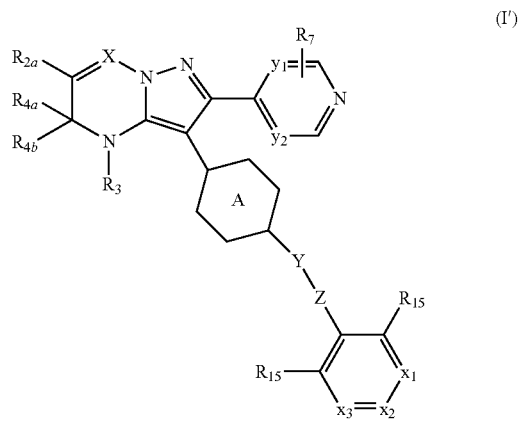

wherein the variables have the meaning defined in the claims. The compounds according to the present invention are useful as ROS1 inhibitors. The invention further relates to processes for preparing novel compounds of the present invention, pharmaceutical compositions comprising com- (Continued)

pounds of the present invention as an active ingredient as well as the use of compounds of the present invention as a medicament.

14 Claims, No Drawings

(51) Int. Cl.
*C07D 487/04* (2006.01)
*A61K 31/4409* (2006.01)
*A61K 31/519* (2006.01)

(56) References Cited

FOREIGN PATENT DOCUMENTS

| WO | WO 2009/086129 A1 | 7/2009 |
|----|-------------------|--------|
| WO | WO 2009/108838 A1 | 9/2009 |
| WO | WO 2009/140128 A2 | 11/2009 |
| WO | WO 2011/153553 A2 | 12/2011 |

OTHER PUBLICATIONS

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

International Search Report of the International Searching Authority relating to corresponding International Patent Application No. PCT/EP2015/056501, filed Mar. 26, 2015, dated May 4, 2015.

Written Opinion of the International Searching Authority relating to corresponding International Patent Application No. PCT/EP2015/056501, filed Mar. 26, 2015, dated May 4, 2015.

Andres et al., "Synthesis, In Vivo Occupancy, and Radiolabeling of Potent Phosphodiesterase Subtype-10 Inhibitors as Candidates for Positron Emission Tomography Imaging.", J. Med. Chem., 2011, 54, pp. 5820-5835.

Davies et al., "Identifying and Targeting ROS1 Gene Fusions in Non-Small Cell Lung Cancer.",Clin Cancer Res., 2012,18(17), pp. 4570-4579.

Gu et al., "Survey of Tyrosine Kinase Signaling Reveals ROS Kinase Fusions in Human Cholangiocarcinoma.", PLoS One, 2011, 6(1):e15640.

Kim et al., "Clinical and prognostic implications of ALK and ROS1 rearrangements in never-smokers with surgically resected lung adenocarcinoma.", Lung Cancer, 2014, 83, pp. 389-395.

Li et al., "Spectrum of Oncogenic Driver Mutations in Lung Adenocarcinomas from East Asian Never Smokers.", PLoS One, 2011, 6, pp. 28204.

Rimkunas et al., "Analysis of Receptor Tyrosine Kinase ROS1-Positive Tumors in Non-Small Cell Lung Cancer: Identification of a FIG-ROS1 Fusion.", Clin Cancer Res., 2012, 18, pp. 4449-4457.

Takeuchi et al., "RET, ROS1 and ALK fusions in lung cancer.", Nature Medicine, Mar. 2012, 18(3), pp. 378-381.

Wiesner et al., "Kinase fusions are frequent in Spitz tumours and spitzoid melanomas.", Nat Commun., 2014, 5, pp. 3116.

\* cited by examiner

SUBSTITUTED 4,5,6,7-TETRAHYDRO-PYRAZOLO[1,5-A]PYRIMIDINE DERIVATIVES AND 2,3-DIHYDRO-1H-IMIDAZO[1,2-B]PYRAZOLE DERIVATIVES AS ROS1 INHIBITORS

CROSS REFERENCE TO RELATED APPLICATIONS

This application is a national stage application of International Patent Application No. PCT/EP2015/056501, filed 26 Mar. 2015, which claims priority from EPO Patent Application No. 14161959.3 filed 27 Mar. 2014.

FIELD OF THE INVENTION

The present invention relates to substituted 4,5,6,7-tetrahydro-pyrazolo[1,5-a]pyrimidine derivatives and 2,3-dihydro-1H-imidazo[1,2-b]pyrazole derivatives useful as ROS1 inhibitors. The invention further relates to processes for preparing such compounds, pharmaceutical compositions comprising said compounds as an active ingredient as well as the use of said compounds as a medicament.

BACKGROUND OF THE INVENTION

Ros1 is a receptor tyrosine kinase closely related to the ALK and LTK kinases based on sequence similarity of their kinase domains. The Ros1 protein is composed of an extracellular domain containing several fibronectin-like repeats and a cytoplasmic kinase domain. The function of Ros1 has not been fully elucidated, but the presence of fibronectin domains suggests a role in cell adhesion or interactions with the extracellular matrix. However, endogenous Ros1 ligands have not yet been identified. Its expression in adult humans has been detected in several tissues, such as the kidney, cerebellum, and gastrointestinal tract, but appears to be low or absent in other tissues. Its expression in the developing kidney and intestine suggests that it may have a role in epithelial-mesenchymal transition. ROS1 deficient mice are healthy and viable, but males are infertile due to defects in the epididymis that result in incomplete spermatocyte maturation.

Several distinct genomic rearrangements involving ROS1 have been detected in a variety of cancers including non-small cell lung cancer (NSCLC), glioblastoma, cholangiocarcinoma, colorectal cancer, gastric adenocarcinoma, ovarian cancer, angiosarcoma, epithelioid hemangioendothelioma, melanoma, and inflammatory myofibroblastic tumors. These rearrangements result in proteins that contain the C-terminal kinase domain of Ros1 fused to the N-terminal domains of a number of different unrelated proteins. Several of these fusion proteins have been shown to be oncogenic. Expression in fibroblasts promotes their proliferation, growth in soft agar, and ability to form tumors in mice. Expression in murine Ba/F3 cells renders them independent of IL-3 for growth and promotes their ability to form tumors in mice (Takeuchi K, et al., Nat Med. 2012, 18:378-81; Gu T L, et al., PLoS One 2011, 6:e15640). The rate of oncogenic Ros1 fusions is generally low, ranging from 1-2% in NSCLC (Kim M H, et al., Lung Cancer 2014, 83:389-95; Takeuchi K, et al., Nat Med. 2012, 18:378-81; Davies K D, et al., Clin Cancer Res. 2012, 18:4570-9; Li C, et al., PLoS One 2011, 6:e28204; Rimkunas V M, et al., Clin Cancer Res. 2012, 18:4449-57), but may be relatively high in other cancers, up to 9% in cholangiocarcinoma (Gu T L, et al., PLoS One 2011, 6(1):e15640) and 17% in spitzoid (melanoma) tumors (Wiesner T, et al., Nat Commun. 2014, 5:3116).

Because of the similarity between ALK and Ros1 kinase domains, many ALK inhibitors also inhibit Ros1. Ros1 inhibition negatively affects proliferation of engineered Ba/F3 cells expressing Ros1 fusion proteins as well as the proliferation of NSCLC patient derived HCC78 cells that harbor a SLC34A2-ROS1 fusion. Ros1 inhibition also negatively affects growth of engineered Ba/F3 and HEK293 tumors containing Ros1 fusion proteins in mice.

Recently, a number of inhibitors described to have activity on Ros1 have entered clinical testing. The first, crizotinib (Xalkori®), has been shown to reduce tumors and significantly prolong survival in patients with ROS1 rearrangements. However, following an initial response, resistance is seen and in one report this has been linked to a G2032R mutation in the Ros1 kinase domain that is expected to affect crizotinib binding.

WO-2004/058176 discloses acyclic pyrazole compounds for the inhibition of mitogen activated protein kinase-activated protein kinase-2.

J. Med. Chem., 2011, 54, 5820-5835 discloses pyrazolo derivatives as phosphodiesterase subtype-10 inhibitors.

WO-2009/086129 relates generally to pyrazolo [1,5-a] pyrimidine-based modulators of Liver X receptors.

WO-2009/108838 relates to pyrazolo[1,5-a]pyrimidine compositions that are useful for inhibiting abnormal growth of certain cell types.

EP1505068 relates to pyrazolo-[1,5-a]-pyrimidine derivatives and analogues as NAD(P)H oxydase inhibitors.

WO-2004/017908 provides a calcium receptor modulator.

There is thus a strong need for novel Ros1 kinase inhibitors thereby opening new avenues for the treatment or prevention of cancer, in particular non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia. In a particular embodiment, there is a need for Ros1 kinase inhibitors that are not affected by mutations that abrogate inhibition of the first wave of Ros1 inhibitors.

It is accordingly an object of the present invention to provide such compounds.

SUMMARY OF THE INVENTION

It has been found that the compounds of the present invention are useful as ROS1 inhibitors. The compounds according to the invention and compositions thereof, may be useful for the treatment or prevention, in particular for the treatment, of cancer, in particular non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia, and the like.

This invention concerns compounds of formula (I)

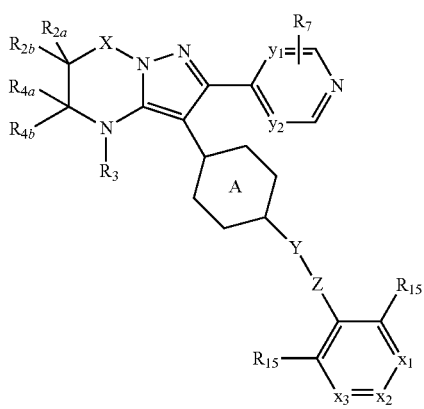

tautomers and stereoisomeric forms thereof, wherein
$y_1$ is $CR_{7a}$ or N;
$y_2$ is CH or N;
$R_{7a}$ is hydrogen, halo, trifluoromethyl or cyano;
$R_7$ is hydrogen, $-NH_2$, $-NHCH_3$, $-NH(CH_2CH_3)$, methyl, $-CH_2OH$, halo or cyano;
or when $y_1$ represents $CR_{7a}$, this $R_{7a}$ can be taken together with a $R_7$ on an adjacent carbon atom to form CH=CH—NH— or —N=CH—NH—;
X is $-CR_1R_{1a}-$ or a covalent bond;
$R_1$ is hydrogen or $C_{1-6}$alkyl;
$R_{1a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one $-NR_{9a}R_{9b}$; or $-C(=O)-NR_{9a}R_{9b}$;
$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of $-NR_{9a}R_{9b}$, cyano and $C_{1-4}$alkyloxy;
$R_{2b}$ is hydrogen or $C_{1-6}$alkyl; or
$R_{2a}$ and $R_{2b}$ are taken together to form $-CH_2-CH_2-$, $-CH_2-NR_2$, $-CH_2-$, $-CH_2-CH_2-CH_2-$, $-CH_2-O-CH_2-$, $-CH_2-CH_2-CH_2-CH_2-$, $-CH_2-CH_2-NR_{2c}-CH_2-$ or =O;
$R_{2c}$ is hydrogen; $C_{1-4}$alkyl optionally substituted with one or two hydroxyl groups; mono- or polyhalo$C_{1-6}$alkyl; $C_{1-6}$alkyloxy; $C_{1-6}$alkyl substituted with one cyano group; or $C_{1-6}$alkyl substituted with one $-NR_{9a}R_{9b}$;
$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; or $C_{1-6}$alkyl substituted with one $R_{11}$;
$R_{4a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo$C_{1-6}$alkylcarbonyl-; $R_{10a}R_{10b}N-C_{1-6}$alkyl-carbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one $-NR_{10a}R_{10b}$; $C_{2-6}$alkenyl; $C_{2-6}$alkynyl; hydroxy$C_{2-6}$alkenyl; hydroxy$C_{2-6}$alkynyl; $C_{1-6}$alkyloxy$C_{2-6}$alkenyl; $C_{1-6}$alkyloxy$C_{2-6}$alkynyl; $C_{2-6}$alkenyl substituted with one $-NR_{10a}R_{10b}$; $C_{2-6}$alkynyl substituted with one $-NR_{10a}R_{10b}$; $C_{1-6}$alkyl substituted with one or two hydroxyl groups and one $-NR_{10}R_{10b}$; $-C_{1-6}$alkyl-C$(R_{13})=N-O-R_{13}$; $-S(=O)_2-C_{1-6}$alkyl; $-S(=O)_2-NR_{9a}R_{9b}$; $C_{1-6}$alkyl substituted with one $-(C=O)-R_{14}$; $C_{1-6}$alkyl substituted with one or two hydroxyl groups and one $R_{14}$; $C_{1-6}$alkyl substituted with one $R_{14}$; $C_{2-6}$alkenyl substituted with one $R_{14}$; $C_{2-6}$alkynyl substituted with one $R_{14}$; or $R_{14}$;
$R_{4b}$ is hydrogen; or
$R_{4a}$ and $R_{4b}$ are taken together to form =O;
Y is —O— or —C(=O)—;
Z is $-CHR_6-$ or $-CH_2-C\equiv C-$;
$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one $-NR_{9a}R_{9b}$; or $-C(=O)-NR_{9a}R_{9b}$;
Ring A is phenyl or a 6 membered saturated, partially saturated or aromatic heterocyclyl, said heterocyclyl containing one or two nitrogen atoms; wherein the phenyl or the heterocyclyl is optionally substituted with one or two $R_8$ substituents; each $R_8$ is independently hydrogen; $C_{1-4}$alkyloxy; hydroxyl; cyano; $C_{1-4}$alkyl or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4):

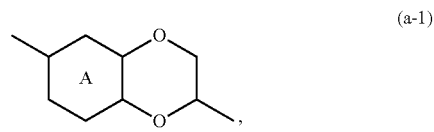

(a-1)

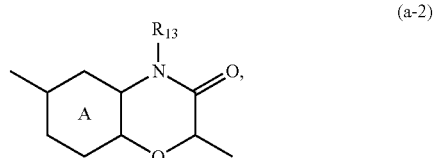

(a-2)

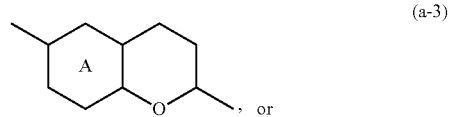

(a-3), or

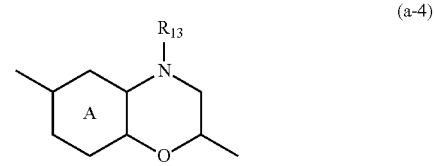

(a-4)

$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;
$R_{10a}$ and $R_{10b}$ each independently represent hydrogen; $C_{1-4}$alkyl; cyano$C_{1-6}$alkyl; $C_{1-6}$alkyl substituted with one $NR_{9a}R_{9b}$; $C_{1-6}$alkyl substituted with one $-C(=O)-NR_{9a}R_{9b}$; $C_{1-6}$alkyloxy optionally substituted with one or two hydroxyl groups; $C_{1-6}$alkyloxy$C_{1-6}$alkyl wherein each $C_{1-6}$alkyl is optionally substituted with one or two hydroxyl groups; $R_{14}$;

$C_{1-6}$alkyl substituted with one $R_{14}$; —(C=O)—$R_{14}$; $C_{1-6}$alkylcarbonyl-; $C_{1-6}$alkyl-O-carbonyl-; mono- or polyhalo$C_{1-6}$alkylcarbonyl-substituted with one or two hydroxyl groups; mono- or polyhalo$C_{1-6}$alkyl substituted with one or two hydroxyl groups; mono- or polyhalo$C_{1-6}$alkylcarbonyl-; $C_{1-6}$alkyl substituted with one —Si(CH$_3$)$_3$; —S(=O)$_2$—$C_{1-6}$alkyl optionally substituted with one or more halo substituents; —S(=O)$_2$—NR$_{9a}$R$_{9b}$;

$C_{1-6}$alkyl substituted with one —S(=O)$_2$—$C_{1-6}$alkyl wherein —S(=O)$_2$—$C_{1-6}$alkyl is optionally substituted with one or more halo substituents;

$C_{1-6}$alkyl substituted with one —S(=O)$_2$—NR$_{9a}$R$_{9b}$;

$C_{1-6}$alkyl substituted with one —NH—S(=O)$_2$—$C_{1-6}$alkyl wherein —NH—S(=O)$_2$—$C_{1-6}$alkyl is optionally substituted on a carbon atom with one or more halo substituents;

$C_{1-6}$alkyl substituted with one —NH—S(=O)$_2$—NR$_{9a}$R$_{9b}$; mono- or polyhalo$C_{1-4}$alkyl; or $C_{1-4}$alkyl substituted with one or two hydroxyl groups;

$R_{11}$ is cyano; —NR$_{10a}$R$_{10b}$; $C_{1-6}$alkyloxy optionally substituted with one or two hydroxyl groups; —S(=O)$_2$—$C_{1-6}$alkyl; —S(=O)$_2$—NR$_{9a}$R$_{9b}$; —NR$_{13}$—S(=O)$_2$—$C_{1-6}$alkyl; —NR$_{13}$—S(=O)$_2$—NR$_{9a}$R$_{9b}$; $C_{1-6}$alkylcarbonyloxy-; —C(=O)—NR$_{10a}$R$_{10b}$; —O—C(=O)—NR$_{10a}$R$_{10b}$; —COOH; —P(=O)(OH)$_2$; or —P(=O)(O—$C_{1-4}$alkyl)$_2$;

$R_{12}$ is —NR$_{9a}$R$_{9b}$, $C_{1-6}$alkyloxy, or cyano;

$R_{13}$ is hydrogen or $C_{1-4}$alkyl;

$R_{14}$ is a $C_{3-8}$cycloalkyl; or a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and NR$_{9a}$R$_{9b}$;

$x_1$ is CR$_{5a}$ or N;
$x_2$ is CR$_{5b}$ or N;
$x_3$ is CR$_{5c}$ or N;

each $R_{15}$ is independently selected from the group consisting of hydrogen, methyl, halo, $C_{1-4}$alkyloxy and hydroxyl;

$R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups; mono- or polyhalo$C_{1-6}$alkyl; mono- or polyhalo$C_{1-6}$alkyloxy; $C_{1-6}$alkyl substituted with one —NR$_{9a}$R$_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —NR$_{9a}$R$_{9b}$;

$R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —Si(CH$_3$)$_3$; $C_{1-6}$alkyl substituted with one $R_{12}$; $C_{1-6}$alkyl-O-carbonyl-; or $C_{1-6}$alkyloxy substituted with one $R_{12}$;

and the N-oxides, the pharmaceutically acceptable addition salts, and the solvates thereof.

This invention also concerns compounds of formula (I')

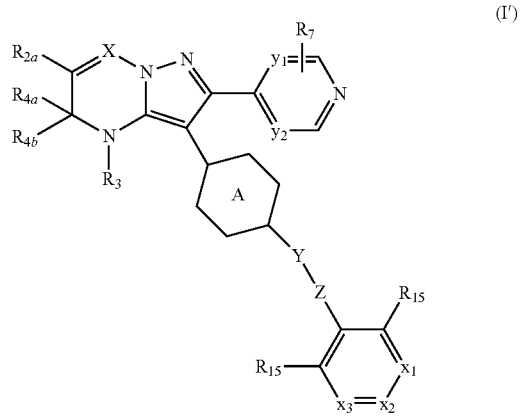

(I')

tautomers and stereoisomeric forms thereof, wherein $y_1$ is CR$_{7a}$ or N;

$y_2$ is CH or N;

$R_{7a}$ is hydrogen, halo, trifluoromethyl or cyano;

$R_7$ is hydrogen, —NH$_2$, —NHCH$_3$, —NH(CH$_2$CH$_3$), methyl, —CH$_2$OH, halo or cyano; or when $y_1$ represents CR$_{7a}$, this $R_{7a}$ can be taken together with a $R_7$ on an adjacent carbon atom to form —CH=CH—NH— or —N=CH—NH—;

X is —CR$_{1a}$—;

$R_{1a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one —NR$_{9a}$R$_{9b}$; —C(=O)—NR$_{9a}$R$_{9b}$; or $C_{1-6}$alkyl-O-carbonyl-;

$R_{2a}$ is hydrogen; $C_{1-6}$alkyl; mono- or polyhalo$C_{1-6}$alkyl; $C_{1-6}$alkyl substituted with one or two hydroxyl groups; $C_{1-6}$alkyloxycarbonyl; or $C_{1-6}$alkyl substituted with one substituent selected from the group consisting of —NR$_{9a}$R$_{9b}$, cyano and $C_{1-4}$alkyloxy;

$R_{4a}$ is hydrogen; halo; $C_{1-6}$alkyl; mono- or polyhalo $C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo$C_{1-6}$alkylcarbonyl-; $R_{10a}R_{10b}$N—$C_{1-6}$alkylcarbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one —NR$_{10a}$R$_{10b}$; $C_{2-6}$alkenyl; $C_{2-6}$alkynyl; hydroxy $C_{2-6}$alkenyl; hydroxy$C_{2-6}$alkynyl; $C_{1-6}$alkyloxy $C_{2-6}$alkenyl; $C_{1-6}$alkyloxy$C_{2-6}$alkynyl; $C_{2-6}$alkenyl substituted with one —NR$_{10a}$R$_{10b}$; $C_{2-6}$alkynyl substituted with one —NR$_{10a}$R$_{10b}$; $C_{1-6}$alkyl substituted with one or two hydroxyl groups and one —NR$_{10}$R$_{10b}$; —$C_{1-6}$alkyl-C(R$_{13}$)=N—O—R$_{13}$; —S(=O)$_2$—$C_{1-6}$alkyl; —S(=O)$_2$—NR$_{9a}$R$_{9b}$; $C_{1-6}$alkyl substituted with one —(C=O)—$R_{14}$; $C_{1-6}$alkyl substituted with one or two hydroxyl groups and one $R_{14}$; $C_{1-6}$alkyl substituted with one $R_{14}$; $C_{2-6}$alkenyl substituted with one $R_{14}$; $C_{2-6}$alkynyl substituted with one $R_{14}$; or $R_{14}$;

$R_{4b}$ and $R_3$ are taken together to form a bond; or $R_{4a}$ and $R_{4b}$ together form =O, in which case $R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; or $C_{1-6}$alkyl substituted with one $R_{11}$;

Y is —O— or —C(=O)—;

Z is —CHR$_6$— or —CH$_2$—C≡C—;

R$_6$ is hydrogen; C$_{1-4}$alkyl-O-carbonyl-; C$_{1-4}$alkyl; C$_{1-4}$alkyl substituted with one or two hydroxyl groups; C$_{1-4}$alkyl substituted with one —NR$_{9a}$R$_{9b}$; or —C(=O)—NR$_{9a}$R$_{9b}$;

Ring A is phenyl or a 6 membered saturated, partially saturated or aromatic heterocyclyl, said heterocyclyl containing one or two nitrogen atoms; wherein the phenyl or the heterocyclyl is optionally substituted with one or two R$_8$ substituents; each R$_8$ is independently hydrogen; C$_{1-4}$alkyloxy; hydroxyl; cyano; C$_{1-4}$alkyl or halo; or a R$_8$ substituent on an atom adjacent to the atom carrying the Y—Z substituent is taken together with the R$_6$ substituent of Z, by which ring A together with Y—Z forms a bicycle of formula (a-1), (a-2), (a-3) or (a-4):

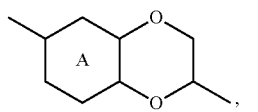

(a-1)

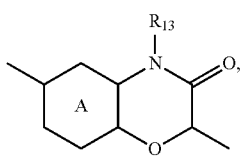

(a-2)

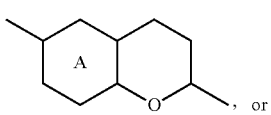

(a-3)

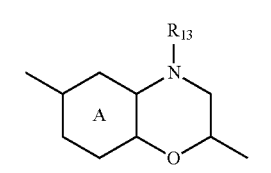

(a-4)

R$_{9a}$ and R$_{9b}$ each independently represent hydrogen; mono- or polyhaloC$_{1-4}$alkyl; C$_{1-4}$alkylcarbonyl-; C$_{1-4}$alkyl-O-carbonyl-; C$_{1-4}$alkyl substituted with one or two hydroxyl groups; or C$_{1-4}$alkyl optionally substituted with one substituent selected from the group consisting of C$_{1-4}$alkyloxy, cyano, amino and mono- or di(C$_{1-4}$alkyl)amino;

R$_{10a}$ and R$_{10b}$ each independently represent hydrogen; C$_{1-4}$alkyl; cyanoC$_{1-6}$alkyl; C$_{1-6}$alkyl substituted with one NR$_{9a}$R$_{9b}$; C$_{1-6}$alkyl substituted with one —C(=O)—NR$_{9a}$R$_{9b}$; C$_{1-6}$alkyloxy optionally substituted with one or two hydroxyl groups; C$_{1-6}$alkyloxyC$_{1-6}$alkyl wherein each C$_{1-6}$alkyl is optionally substituted with one or two hydroxyl groups; R$_{14}$; C$_{1-6}$alkyl substituted with one R$_{14}$; —(C=O)—R$_{14}$; C$_{1-6}$alkylcarbonyl-; C$_{1-6}$alkyl-O-carbonyl-; mono- or polyhaloC$_{1-6}$alkylcarbonyl-substituted with one or two hydroxyl groups; mono- or polyhaloC$_{1-6}$alkyl substituted with one or two hydroxyl groups; mono- or polyhaloC$_{1-6}$alkylcarbonyl-; C$_{1-6}$alkyl substituted with one —Si(CH$_3$)$_3$; —S(=O)$_2$—C$_{1-6}$alkyl optionally substituted with one or more halo substituents; —S(=O)$_2$—NR$_{9a}$R$_{9b}$;

C$_{1-6}$alkyl substituted with one —S(=O)$_2$—C$_{1-6}$alkyl wherein —S(=O)$_2$—C$_{1-6}$alkyl is optionally substituted with one or more halo substituents;

C$_{1-6}$alkyl substituted with one —S(=O)$_2$—NR$_{9a}$R$_{9b}$;

C$_{1-6}$alkyl substituted with one —NH—S(=O)$_2$—C$_{1-6}$alkyl wherein —NH—S(=O)$_2$—C$_{1-6}$alkyl is optionally substituted on a carbon atom with one or more halo substituents;

C$_{1-6}$alkyl substituted with one —NH—S(=O)$_2$—NR$_{9a}$R$_{9b}$; mono- or polyhaloC$_{1-4}$alkyl; or C$_{1-4}$alkyl substituted with one or two hydroxyl groups;

R$_{11}$ is cyano, —NR$_{10a}$R$_{10b}$; C$_{1-6}$alkyloxy optionally substituted with one or two hydroxyl groups; —S(=O)$_2$—C$_{1-6}$alkyl; —S(=O)$_2$—NR$_{9a}$R$_{9b}$; —NR$_{13}$—S(=O)$_2$—C$_{1-6}$alkyl; —NR$_{13}$—S(=O)$_2$—NR$_{9a}$R$_{9b}$; C$_{1-6}$alkylcarbonyloxy-; —C(=O)—NR$_{10a}$R$_{10b}$; —COOH, —O—C(=O)—NR$_{10a}$R$_{10b}$; —COOH, —P(=O)(OH)$_2$; or —P(=O)(O—C$_{1-4}$alkyl)$_2$;

R$_{12}$ is —NR$_{9a}$R$_{9b}$, C$_{1-6}$alkyloxy, or cyano;

R$_{13}$ is hydrogen or C$_{1-4}$alkyl;

R$_{14}$ is a C$_{3-8}$cycloalkyl; or a 4, 5 or 6 membered saturated heterocyclyl which is optionally substituted with one, two or three substituents selected from the group consisting of oxo, C$_{1-4}$alkyl, halogen, cyano, hydroxyl, C$_{1-6}$alkyloxy and NR$_{9a}$R$_{9b}$;

x$_1$ is CR$_{5a}$ or N;
x$_2$ is CR$_{5b}$ or N;
x$_3$ is CR$_{5c}$ or N;

each R$_{15}$ is independently selected from the group consisting of hydrogen, methyl, halo, C$_{1-4}$alkyloxy and hydroxyl;

R$_{5a}$ and R$_{5c}$ each independently are selected from the group consisting of hydrogen; hydroxyl; cyano; halo; C$_{1-6}$alkyl; C$_{1-6}$alkyl substituted with one or two hydroxyl groups; mono- or polyhaloC$_{1-6}$alkyl; mono- or polyhaloC$_{1-6}$alkyloxy; C$_{1-6}$alkyl substituted with one —NR$_{9a}$R$_{9b}$; C$_{1-6}$alkyl substituted with one cyano; C$_{1-6}$alkyloxyC$_{1-6}$alkyl wherein each of the C$_{1-6}$alkyl groups are optionally substituted with one or two hydroxyl groups; C$_{2-6}$alkenyl; C$_{1-6}$alkyl-O-carbonyl-; C$_{1-6}$alkyloxy; C$_{1-6}$alkyloxy substituted with one or two hydroxyl groups; C$_{1-6}$alkyloxyC$_{1-6}$alkyloxy wherein each of the C$_{1-6}$alkyl groups are optionally substituted with one or two hydroxyl groups; C$_{1-6}$alkyloxy substituted with one cyano; and C$_{1-6}$alkyloxy substituted with one —NR$_{9a}$R$_{9b}$;

R$_{5b}$ is hydrogen; C$_{1-6}$alkyl; C$_{3-6}$cycloalkyl optionally substituted with one cyano; hydroxyl; cyano; mono- or polyhaloC$_{1-6}$alkyloxy; mono- or polyhaloC$_{1-6}$alkyl; C$_{1-4}$alkyl substituted with one or two hydroxyl groups; C$_{2-6}$alkenyl; C$_{1-4}$alkyloxy; —Si(CH$_3$)$_3$; C$_{1-6}$alkyl substituted with one R$_{12}$; C$_{1-6}$alkyl-O-carbonyl-; or C$_{1-6}$alkyloxy substituted with one R$_{12}$;

and the N-oxides, the pharmaceutically acceptable addition salts, and the solvates thereof.

Compounds of formula (I') can be used to prepare compounds of formula (I).

The present invention also concerns methods for the preparation of compounds of the present invention and pharmaceutical compositions comprising them.

The compounds of the present invention were found to inhibit ROS1, and therefore may be useful in the treatment or prevention, in particular in the treatment, of cancer, in particular non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia, and the like. The compounds of the present invention may also have utility in male contraception.

In view of the aforementioned pharmacology of the compounds of Formula (I), (I'), and N-oxides, pharmaceutically acceptable addition salts, and solvates thereof, it follows that they may be suitable for use as a medicament.

In particular the compounds of Formula (I), (I'), and N-oxides, pharmaceutically acceptable addition salts, and solvates thereof, may be suitable in the treatment or prevention, in particular in the treatment, of cancer.

The present invention also concerns the use of compounds of Formula (I), (I'), and pharmaceutically acceptable addition salts, and solvates thereof, for the manufacture of a medicament for the inhibition of ROS1, for the treatment or prevention of cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. formula (I) or (I')), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Whenever a radical or group is defined as "optionally substituted" in the present invention, it is meant that said radical or group is unsubstituted or is substituted.

Lines drawn from substituents into ring systems indicate that the bond may be attached to any of the suitable ring atoms.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term "halo" as a group or part of a group is generic for fluoro, chloro, bromo, iodo unless otherwise is indicated or is clear from the context.

The term 'mono- or polyhalo$C_{1-4}$alkyl' or 'mono- or polyhalo$C_{1-6}$alkyl' as used herein as a group or part of a group refers to a $C_{1-4}$alkyl or $C_{1-6}$alkyl group as defined herein wherein one or more than one hydrogen atom is replaced with a halogen. There may be one, two, three or more hydrogen atoms replaced with a halogen, so the 'mono- or polyhalo$C_{1-4}$alkyl' or 'mono- or polyhalo $C_{1-6}$alkyl' may have one, two, three or more halogens. Examples of such groups include fluoroethyl, fluoromethyl, trifluoromethyl or trifluoroethyl and the like.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{1-6}$alkyloxy" as a group or part of a group refers to a radical having the Formula —$OR^b$ wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{1-6}$alkylcarbonyl" as a group or part of a group refers to a radical —C(=O)—$C_{1-6}$alkyl. The term "$C_{1-4}$alkylcarbonyl" as a group or part of a group refers to a radical —C(=O)—$C_{1-4}$alkyl.

The term "$C_{3-8}$cycloalkyl" alone or in combination, refers to a cyclic saturated hydrocarbon radical having from 3 to 8 carbon atoms. Non-limiting examples of suitable $C_{3-8}$cycloalkyl include cyclopropyl, cyclobutyl, cyclopentyl, cyclohexyl, cycloheptyl and cyclooctyl.

The term "$C_{3-6}$cycloalkyl" alone or in combination, refers to a cyclic saturated hydrocarbon radical having from 3 to 6 carbon atoms. Non-limiting examples of suitable $C_{3-6}$cycloalkyl include cyclopropyl, cyclobutyl, cyclopentyl and cyclohexyl.

The term "$C_{2-4}$alkenyl" or "$C_{2-6}$alkenyl" as used herein as a group or part of a group refers to a linear or branched hydrocarbon group containing from 2 to 4 or 2 to 6 carbon atoms and containing a carbon carbon double bond such as, but not limited to, ethenyl, propenyl, butenyl, pentenyl, 1-propen-2-yl, hexenyl and the like.

The term "$C_{2-4}$alkynyl" or "$C_{2-6}$alkynyl" as used herein as a group or part of a group refers to a linear or branched hydrocarbon group having from 2 to 4 or 2 to 6 carbon atoms and containing a carbon carbon triple bond.

The term "cyanoC$_{1-6}$alkyl" means C$_{1-6}$alkyl substituted with one cyano.

The term "hydroxyC$_{2-6}$alkenyl" means C$_{2-6}$alkenyl substituted with one hydroxy.

The term "hydroxyC$_{2-6}$alkynyl" means C$_{2-6}$alkynyl substituted with one hydroxy.

In particular, the 4, 5 or 6 membered saturated heterocyclyls (e.g. in the definition of R$_{14}$), contain 1, 2 or 3 heteroatoms selected from O, S and N, in particular 1 or 2 heteroatoms, in particular selected from O and N.

Examples of 4, 5 or 6 membered saturated heterocyclyls include, but are not limited to, pyrrolidinyl, dioxolanyl, oxazolidinyl, oxetanyl, tetrahydrofuranyl, and the like.

Examples of 6-membered aromatic heterocyclyls containing one or two nitrogen atoms (e.g. in the definition of ring A), include, but are not limited to, pyrimidinyl, pyridinyl, pyrazinyl and the like.

Examples of 6-membered partially saturated heterocyclyls containing one or two nitrogen atoms (e.g. in the definition of ring A), include, but are not limited to, 1,2,3,6-tetrahydro-pyridinyl and the like. In a particular embodiment, the 1,2,3,6-tetrahydro-pyridinyl is attached with its nitrogen atom to variable Y.

Examples of 6-membered saturated heterocyclyls containing one or two nitrogen atoms (e.g. in the definition of ring A), include, but are not limited to, piperidinyl and the like. In a particular embodiment, the piperidinyl is attached with its nitrogen atom to the pyrazolyl ring.

In case R$_{7a}$ is taken together with a R$_7$ on an adjacent carbon atom to form —CH=CH—NH—, it is intended that the CH in position alpha

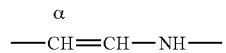

is attached to the carbon atom in the position of y1 as clearly shown below:

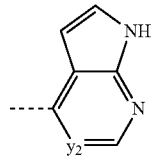

In case R$_{7a}$ is taken together with a R$_7$ on an adjacent carbon atom to form —N=CH—NH—, it is intended that the nitrogen in position alpha

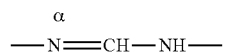

is attached to the carbon atom in the position of y1 as clearly shown below:

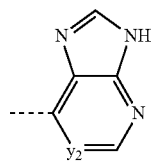

In case Z is —CH$_2$—C≡C—, it is intended that the CH$_2$ group is attached to variable Y.

It will be clear that when a R$_8$ substituent on an atom adjacent to the atom carrying the Y—Z substituent is taken together with the R$_6$ substituent of Z, compounds of formula (I-a-1), (I-a-2), (I-a-3) and (I-a-4) are formed:

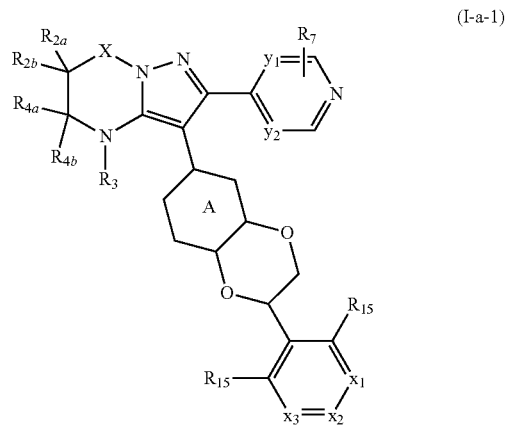

(I-a-1)

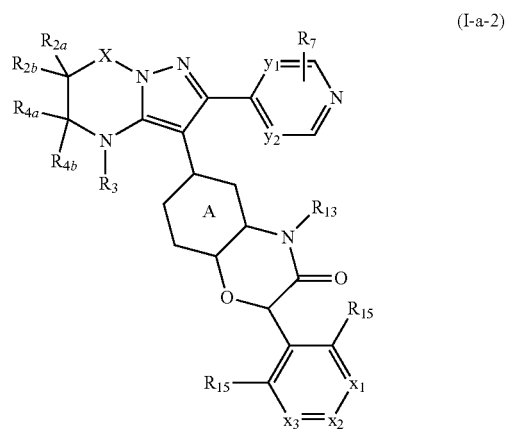

(I-a-2)

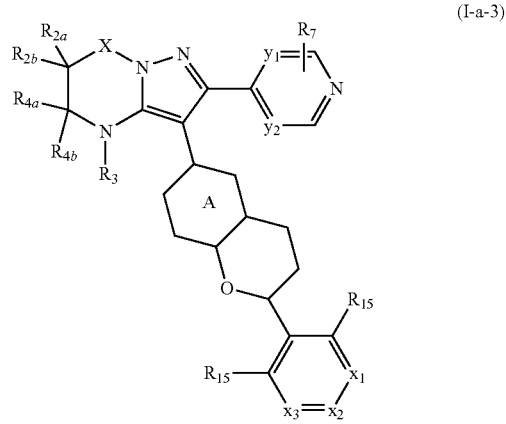

(I-a-3)

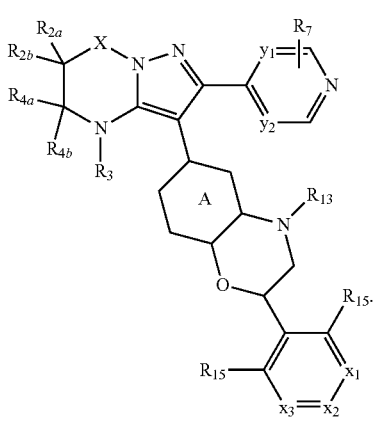

(I-a-4)

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I), (I'), and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Whenever one of the ring systems, is substituted with one or more substituents, those substituents may replace any hydrogen atom bound to a carbon or nitrogen atom of the ring system.

Hereinbefore and hereinafter, the term "compound of Formula I)" is meant to include the stereoisomers thereof and the tautomeric forms thereof.

Hereinbefore and hereinafter, the term "compound of Formula (I')" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as F, this means that the compound is substantially free of the Z isomer; when a compound of Formula (I) is for instance specified as cis, this means that the compound is substantially free of the trans isomer.

Some of the compounds of Formula (I) or (I') may also exist in their tautomeric form. Such forms in so far as they may exist, are intended to be included within the scope of the present invention.

It follows that a single compound may exist in both stereoisomeric and tautomeric form.

For therapeutic use, salts of the compounds of Formula (I), (I'), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), (I'), and N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), (I'), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) or (I') are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), (I'), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I) or (I'), comprises all isotopes and isotopic mixtures of this element, either naturally occurring or synthetically produced, either with natural abundance or in an isotopically enriched form. Radiolabelled compounds of Formula (I) or (I') may comprise a radioactive isotope selected from the group of $^{2}H$, $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$.

In particular, deuterated compounds are intended to be included within the scope of the present invention As used in the specification and the appended claims, the singular forms "a", "an," and "the" also include plural referents unless the context clearly dictates otherwise. For example, "a compound" means 1 compound or more than 1 compound.

In an embodiment, the present invention concerns novel compounds of Formula (I), tautomers and stereoisomeric forms thereof, wherein $y_1$ is $CR_{7a}$ or N;
$y_2$ is CH;
$R_{7a}$ is hydrogen;
$R_7$ is hydrogen, —$NH_2$, —$CH_2OH$, halo or cyano; or when $y_1$ represents $CR_{7a}$, this $R_{7a}$ can be taken together with a $R_7$ on an adjacent carbon atom to form —CH=CH—NH—;
X is —$CR_1R_{1a}$—;
$R_1$ is hydrogen or $C_{1-6}$alkyl;
$R_{1a}$ is hydrogen;
$R_{2a}$ is hydrogen; $C_{1-6}$alkyl; $C_{1-6}$alkyl substituted with one hydroxyl group; or $C_{1-6}$alkyl substituted with one substituent selected from the group consisting of —$NR_{9a}R_{9b}$;
$R_{2b}$ is hydrogen; or
$R_{2a}$ and $R_{2b}$ are taken together to form —$CH_2$—$CH_2$—, —$CH_2$—$NR_{2c}$—$CH_2$— or =O;
$R_{2c}$ is hydrogen; or $C_{1-6}$alkyl substituted with one —$NR_{9a}R_{9b}$;
$R_3$ is hydrogen; $C_{1-6}$alkyl; $C_{1-6}$alkyl substituted with one or two hydroxyl groups; $C_{1-6}$alkyl substituted with one or two hydroxyl groups and one $C_{1-6}$alkyloxy; or $C_{1-6}$alkyl substituted with one $R_{11}$;
$R_{4a}$ is hydrogen; $C_{1-6}$alkyl; $C_{1-6}$alkyl substituted with one hydroxyl group; or $C_{1-6}$alkyl substituted with one $R_{11}$;
$R_{4b}$ is hydrogen; or
$R_{4a}$ and $R_{4b}$ are taken together to form =O;
Y is —O— or —C(=O)—;
Z is —$CHR_6$— or —$CH_2$—C≡C—;
$R_6$ is hydrogen; $C_{1-4}$alkyl-O-carbonyl-; $C_{1-4}$alkyl; $C_{1-4}$alkyl substituted with one hydroxyl group; $C_{1-4}$alkyl substituted with one —$NR_{9a}R_{9b}$; or —C(=O)—$NR_{9a}R_{9b}$;
Ring A is phenyl or a 6-membered saturated, partially saturated or aromatic heterocyclyl, said heterocyclyl containing one or two nitrogen atoms; wherein the phenyl or the heterocyclyl is optionally substituted with one or two $R_8$ substituents; each $R_8$ is independently hydrogen; $C_{1-4}$alkyloxy; cyano; or halo;
or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a) or (a-4b):

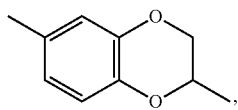
(a-1a)

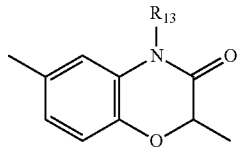
(a-2a)

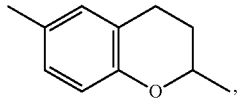
(a-3a)

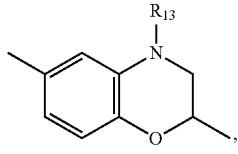
(a-4a)

-continued (a-4b)
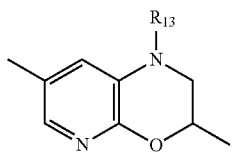

R$_{9a}$ and R$_{9b}$ each independently represent hydrogen; C$_{1-4}$alkyl substituted with one hydroxyl group; or C$_{1-4}$alkyl;

R$_{10a}$ and R$_{10b}$ each independently represent hydrogen; C$_{1-4}$alkyl; C$_{1-6}$alkyl-O-carbonyl-; mono- or polyhaloC$_{1-4}$alkyl; or C$_{1-4}$alkyl substituted with one hydroxyl group;

R$_{11}$ is cyano; —NR$_{10a}$R$_{10b}$; C$_{1-6}$alkyloxy optionally substituted with one hydroxyl group; —S(=O)$_2$—C$_{1-6}$alkyl; C$_{1-6}$alkylcarbonyloxy-; —C(=O)—NR$_{10a}$R$_{10b}$; —COOH; or —P(=O)(O—C$_{1-4}$alkyl)$_2$;

R$_{12}$ is —NR$_{9a}$R$_{9b}$, C$_{1-6}$alkyloxy, or cyano;

R$_{13}$ is hydrogen or C$_{1-4}$alkyl;

R$_{14}$ is a 5 membered saturated heterocyclyl which is optionally substituted with one, two or three substituents selected from the group consisting of oxo and C$_{1-4}$alkyl;

x$_1$ is CR$_{5a}$ or N;

x$_2$ is CR$_{5b}$;

x$_3$ is CR$_5$, or N;

each R$_{15}$ is independently selected from the group consisting of hydrogen, methyl, halo, and C$_{1-4}$alkyloxy;

R$_{5a}$ and R$_{5c}$ each independently are selected from the group consisting of hydrogen; hydroxyl; cyano; halo; C$_{1-6}$alkyl substituted with one or two hydroxyl groups; C$_{1-6}$alkyl substituted with one —NR$_{9a}$R$_{9b}$; C$_{1-6}$alkyloxyC$_{1-6}$alkyl; C$_{1-6}$alkyloxy; C$_{1-6}$alkyloxy substituted with one hydroxyl group; and C$_{1-6}$alkyloxyC$_{1-6}$alkyloxy;

R$_{5b}$ is hydrogen; C$_{1-6}$alkyl; C$_{3-6}$cycloalkyl optionally substituted with one cyano; cyano; mono- or polyhalo C$_{1-6}$alkyloxy; mono- or polyhaloC$_{1-6}$alkyl; C$_{1-4}$alkyl substituted with one hydroxyl group; C$_{2-6}$alkenyl; C$_{1-4}$alkyloxy; —Si(CH$_3$)$_3$; C$_{1-6}$alkyl substituted with one R$_{12}$; or C$_{1-6}$alkyl-O-carbonyl-;

and the N-oxides, the pharmaceutically acceptable addition salts, and the solvates thereof.

Another embodiment of the present invention relates to those compounds of formula (I) and the N-oxides, the pharmaceutically acceptable addition salts, and the solvates thereof, or any subgroup thereof as mentioned in any of the other embodiments wherein the bicycles of formula (a-1), (a-2), (a-3) and (a-4) are limited to bicycles of formula (a-1a), (a-2a), (a-3a), (a-4a) and (a-4b) having the following structures:

(a-1a)
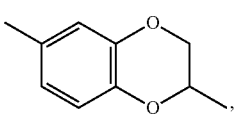

(a-2a)
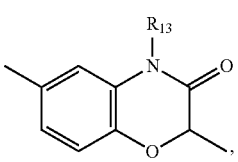

(a-3a)
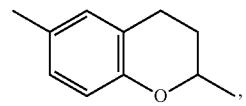

(a-4a)
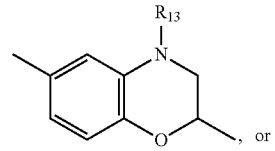

, or (a-4b)
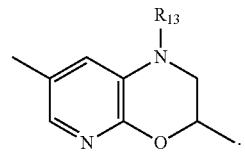

In an embodiment, the present invention concerns novel compounds of Formula (I), tautomers and stereoisomeric forms thereof, wherein y$_1$ is CR$_{7a}$ or N;

y$_2$ is CH;

R$_{7a}$ is hydrogen;

R$_7$ is hydrogen, —NH$_2$, —CH$_2$OH, halo or cyano;

or when y$_1$ represents CR$_{7a}$, this R$_{7a}$ can be taken together with a R$_7$ on an adjacent carbon atom to form —CH=CH—NH—;

X is —CR$_1$R$_{1a}$—;

R$_1$ is hydrogen or C$_{1-6}$alkyl;

R$_{1a}$ is hydrogen;

R$_{2a}$ is hydrogen; C$_{1-6}$alkyl; C$_{1-6}$alkyl substituted with one hydroxyl group; or C$_{1-6}$alkyl substituted with one substituent selected from the group consisting of —NR$_{9a}$R$_{9b}$;

R$_{2b}$ is hydrogen; or

R$_{2a}$ and R$_{2b}$ are taken together to form —CH$_2$—CH$_2$—, —CH$_2$—NR$_{2c}$—CH$_2$— or =O;

R$_{2c}$ is hydrogen; or C$_{1-6}$alkyl substituted with one —NR$_{9a}$R$_{9b}$;

R$_3$ is hydrogen; C$_{1-6}$alkyl; C$_{1-6}$alkyl substituted with one or two hydroxyl groups;

C$_{1-6}$alkyl substituted with one or two hydroxyl groups and one C$_{1-6}$alkyloxy; or C$_{1-6}$alkyl substituted with one R$_{11}$;

R$_{4a}$ is hydrogen; C$_{1-6}$alkyl; C$_{1-6}$alkyl substituted with one hydroxyl group; or C$_{1-6}$alkyl substituted with one R$_{11}$;

R$_{4b}$ is hydrogen; or

R$_{4a}$ and R$_{4b}$ are taken together to form =O;

Y is —O— or —C(=O)—;

Z is —CHR$_6$— or —CH$_2$—C≡C—;

R$_6$ is hydrogen; C$_{1-4}$alkyl-O-carbonyl-; C$_{1-4}$alkyl; C$_{1-4}$alkyl substituted with one hydroxyl group; C$_{1-4}$alkyl substituted with one —NR$_{9a}$R$_{9b}$; or —C(=O)—NR$_{9a}$R$_{9b}$;

Ring A is phenyl or a 6-membered saturated, partially saturated or aromatic heterocyclyl, said heterocyclyl containing one or two nitrogen atoms; wherein the phenyl or the heterocyclyl is optionally substituted with one or two R$_8$ substituents; each R$_8$ is independently hydrogen; C$_{1-4}$alkyloxy; cyano; or halo;

R$_{9a}$ and R$_{9b}$ each independently represent hydrogen; C$_{1-4}$alkyl substituted with one hydroxyl group; or C$_{1-4}$alkyl;

$R_{10a}$ and $R_{10b}$ each independently represent hydrogen; $C_{1-4}$alkyl; $C_{1-6}$alkyl-O-carbonyl-; mono- or polyhalo$C_{1-4}$alkyl; or $C_{1-4}$alkyl substituted with one hydroxyl group;

$R_{11}$ is cyano; —$NR_{10a}R_{10b}$; $C_{1-6}$alkyloxy optionally substituted with one hydroxyl group; —$S(=O)_2$—$C_{1-6}$alkyl; $C_{1-6}$alkylcarbonyloxy-; —$C(=O)$—$NR_{10a}R_{10b}$; —COOH; or —$P(=O)(O$—$C_{1-4}$alkyl$)_2$;

$R_{12}$ is —$NR_{9a}R_{9b}$, $C_{1-6}$alkyloxy, or cyano;

$R_{14}$ is a 5 membered saturated heterocyclyl which is optionally substituted with one, two or three substituents selected from the group consisting of oxo and $C_{1-4}$alkyl;

$x_1$ is $CR_{5a}$ or N;
$x_2$ is $CR_{5b}$;
$x_3$ is $CR_{5c}$ or N;

each $R_{15}$ is independently selected from the group consisting of hydrogen, methyl, halo, and $C_{1-4}$alkyloxy;

$R_{5a}$ and $R_{5c}$ each independently are selected from the group consisting of hydrogen; hydroxyl; cyano; halo; $C_{1-6}$alkyl substituted with one or two hydroxyl groups; $C_{1-6}$alkyl substituted with one —$NR_{9a}R_{9b}$; $C_{1-6}$alkyloxy$C_{1-6}$alkyl; $C_{1-6}$alkyloxy; $C_{1-6}$alkyloxy substituted with one hydroxyl group; and $C_{1-6}$alkyloxy$C_{1-6}$alkyloxy;

$R_{5b}$ is hydrogen; $C_{1-6}$alkyl; $C_{3-6}$cycloalkyl optionally substituted with one cyano; cyano; mono- or polyhalo $C_{1-6}$alkyloxy; mono- or polyhalo$C_{1-6}$alkyl; $C_{1-4}$alkyl substituted with one hydroxyl group; $C_{2-6}$alkenyl; $C_{1-4}$alkyloxy; —$Si(CH_3)_3$; $C_{1-6}$alkyl substituted with one $R_{12}$; or $C_{1-6}$alkyl-O-carbonyl-;

and the N-oxides, the pharmaceutically acceptable addition salts, and the solvates thereof.

In an embodiment, the present invention concerns novel compounds of Formula (I), tautomers and stereoisomeric forms thereof, wherein $y_1$ is $CR_{7a}$ or N;
$y_2$ is CH;
$R_{7a}$ is hydrogen;
$R_7$ is hydrogen;
X is —$CR_1R_{1a}$— or a covalent bond;
$R_1$ is hydrogen;
$R_{1a}$ is hydrogen; $C_{1-6}$alkyl substituted with one hydroxyl group; $C_{1-6}$alkyl substituted with one —$NR_9aR_{9b}$; or —$C(=O)$—$NR_{9a}R_{9b}$;
$R_{2a}$ is hydrogen;
$R_{2b}$ is hydrogen;
$R_3$ is hydrogen; or $C_{1-6}$alkyl substituted with one hydroxyl group;
$R_{4a}$ is hydrogen; $C_{1-6}$alkyl; $C_{1-6}$alkyl substituted with one hydroxyl group; or $C_{1-6}$alkyl substituted with one $R_{11}$;
$R_{4b}$ is hydrogen; or
$R_{4a}$ and $R_{4b}$ are taken together to form =O;
Y is —O—;
Z is —$CHR_6$—;
$R_6$ is hydrogen;
Ring A is phenyl or a 6 membered aromatic heterocyclyl, said heterocyclyl containing one or two nitrogen atoms; wherein the phenyl or the heterocyclyl is optionally substituted with one or two $R_8$ substituents;
each $R_8$ is independently hydrogen; cyano; or halo;
$R_{9a}$ and $R_{9b}$ each independently represent hydrogen; or $C_{1-4}$alkyl;
$R_{10a}$ and $R_{10b}$ each represent hydrogen;
$R_{11}$ is —$NR_{10a}R_{10b}$;
$x_1$ is $CR_{5a}$; $x_2$ is $CR_{5b}$; $x_3$ is $CR_{5c}$;

each $R_{15}$ is independently selected from the group consisting of hydrogen and halo;

$R_{5a}$ and $R_{5c}$ each independently are selected from the group consisting of hydrogen; cyano; halo; and $C_{1-6}$alkyl substituted with one or two hydroxyl groups;

$R_{5b}$ is $C_{1-6}$alkyl or $C_{3-6}$cycloalkyl;

and the N-oxides, the pharmaceutically acceptable addition salts, and the solvates thereof.

In an embodiment, the present invention relates to those compounds of formula (I) and the N-oxides, the pharmaceutically acceptable addition salts, and the solvates thereof, or any subgroup thereof as mentioned in any of the other embodiments, wherein $C_{1-6}$alkyl is limited to $C_{1-4}$alkyl.

In an embodiment, the present invention concerns novel compounds of Formula (I), tautomers and stereoisomeric forms thereof, wherein $y_1$ is CH; $y_2$ is CH; $R_7$ is hydrogen; X is a covalent bond; $R_{2a}$ is hydrogen; $R_{2b}$ is hydrogen;
$R_3$ is hydrogen, or $C_{1-6}$alkyl substituted with one hydroxyl group;
$R_{4a}$ is hydrogen; $R_{4b}$ is hydrogen;
Y is —O—;
Z is —$CHR_6$—; $R_6$ is hydrogen;
Ring A is phenyl optionally substituted with one $R_8$ substituent;
each $R_8$ is independently hydrogen or halo;
$x_1$ is CH; $x_2$ is $CR_{5b}$; $x_3$ is CH;
each $R_{15}$ is hydrogen;
$R_{5b}$ is $C_{1-6}$alkyl or $C_{3-6}$cycloalkyl;
and the N-oxides, the pharmaceutically acceptable addition salts, and the solvates thereof.

Another embodiment of the present invention relates to those compounds of formula (I) and the N-oxides, the pharmaceutically acceptable addition salts, and the solvates thereof, or any subgroup thereof as mentioned in any of the other embodiments wherein one or more of the following restrictions apply:

(i) $y_1$ is $CR_{7a}$ or N;
(ii) $y_2$ is CH;
(iii) $R_{7a}$ is hydrogen;
(iv) $R_7$ is hydrogen;
(v) X is —$CR_1R_{1a}$— or a covalent bond;
(vi) $R_1$ is hydrogen;
(vii) $R_{1a}$ is hydrogen; $C_{1-6}$alkyl substituted with one hydroxyl group; $C_{1-6}$alkyl substituted with one —$NR_{9a}R_{9b}$; or —$C(=O)$—$NR_{9a}R_{9b}$;
(viii) $R_{2a}$ is hydrogen; $R_{2b}$ is hydrogen;
(ix) $R_3$ is hydrogen; or $C_{1-6}$alkyl substituted with one hydroxyl group;
(x) $R_{4a}$ is hydrogen; $C_{1-6}$alkyl; $C_{1-6}$alkyl substituted with one hydroxyl group; or $C_{1-6}$alkyl substituted with one $R_{11}$;
$R_{4b}$ is hydrogen; or
$R_{4a}$ and $R_{4b}$ are taken together to form =O;
(xi) Ring A is phenyl or a 6 membered aromatic heterocyclyl, said heterocyclyl containing one or two nitrogen atoms; wherein the phenyl or the heterocyclyl is optionally substituted with one or two $R_8$ substituents;
(xii) each $R_8$ is independently hydrogen; cyano; or halo;
(xiii) $R_{9a}$ and $R_{9b}$ each independently represent hydrogen; or $C_{1-4}$alkyl;
(xiv) $R_{10a}$ and $R_{10b}$ each represent hydrogen;
(xv) $R_{11}$ is —$NR_{10a}R_{10b}$;
(xvi) Y is —O—;
(xvii) Z is —$CHR_6$—;
(xviii) $R_6$ is hydrogen;
(xix) $x_1$ is $CR_{5a}$; $x_2$ is $CR_{5b}$; $x_3$ is $CR_{5c}$;

(xx) each $R_{15}$ is independently selected from the group consisting of hydrogen and halo;
(xxi) $R_{5a}$ and $R_{5c}$ each independently are selected from the group consisting of hydrogen; cyano; halo; and $C_{1-6}$alkyl substituted with one or two hydroxyl groups;
(xxii) $R_{5b}$ is $C_{1-6}$alkyl or $C_{3-6}$cycloalkyl.

Another embodiment of the present invention relates to those compounds of formula (I) and the N-oxides, the pharmaceutically acceptable addition salts, and the solvates thereof, or any subgroup thereof as mentioned in any of the other embodiments wherein one or more of the following restrictions apply:
(i) $y_1$ is CH;
(ii) $y_2$ is CH;
(iii) $R_7$ is hydrogen;
(iv) X is a covalent bond;
(v) $R_{2a}$ is hydrogen; $R_{2b}$ is hydrogen;
(vi) $R_3$ is hydrogen, or $C_{1-6}$alkyl substituted with one hydroxyl group;
(vii) $R_{4a}$ is hydrogen; $R_{4b}$ is hydrogen;
(viii) Ring A is phenyl optionally substituted with one $R_8$ substituent;
(ix) each $R_8$ is independently hydrogen or halo;
(x) Y is —O—;
(xi) Z is —$CHR_6$—;
(xii) $R_6$ is hydrogen;
(xiii) $x_1$ is CH; $x_2$ is $CR_{5b}$; $x_3$ is CH;
(xiv) each $R_{15}$ is hydrogen;
(xv) $R_{5b}$ is $C_{1-6}$alkyl or $C_{3-6}$cycloalkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ is hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ is hydrogen when $R_1$ and $R_{1a}$ are other than hydrogen; or $R_1$ and $R_{1a}$ are hydrogen when $R_{4a}$ is other than hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein Y is O.

In an embodiment, the present invention relates to those compounds of formula (I) and the N-oxides, the pharmaceutically acceptable addition salts, and the solvates thereof, or any subgroup thereof as mentioned in any of the other embodiments, wherein each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4).

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered saturated, partially saturated or aromatic heterocyclyl, in particular phenyl or a 6-membered aromatic heterocyclyl, said heterocyclyl containing one or two nitrogen atoms; wherein the phenyl or the heterocyclyl is optionally substituted with one or two $R_8$ substituents;
each $R_8$ is independently hydrogen; $C_{1-4}$alkyloxy; hydroxyl; cyano; $C_{1-4}$alkyl or halo.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered saturated, partially saturated or aromatic heterocyclyl, in particular phenyl or a 6-membered aromatic heterocyclyl, said heterocyclyl containing one or two nitrogen atoms; wherein the phenyl or the heterocyclyl is optionally substituted with one or two $R_8$ substituents;
each $R_8$ is independently hydrogen; $C_{1-4}$alkyloxy; hydroxyl; cyano; or halo.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is optionally substituted with one or two $R_8$ substituents.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl.

In an embodiment, the present invention relates to those compounds of formula (I) and the N-oxides, the pharmaceutically acceptable addition salts, and the solvates thereof, or any subgroup thereof as mentioned in any of the other embodiments, wherein each $R_8$ is independently hydrogen; $C_{1-4}$alkyloxy; hydroxyl; cyano; or halo.

In an embodiment, the present invention relates to those compounds of formula (I) and the N-oxides, the pharmaceutically acceptable addition salts, and the solvates thereof, or any subgroup thereof as mentioned in any of the other embodiments, wherein each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a) or (a-4b).

In an embodiment, the present invention relates to those compounds of formula (I) and the N-oxides, the pharmaceutically acceptable addition salts, and the solvates thereof, or any subgroup thereof as mentioned in any of the other embodiments, wherein Z is —$CHR_6$— and Y is O.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_8$ is other than $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4); and Y is —O—.

In an embodiment, the present invention relates to those compounds of formula (I) and the N-oxides, the pharmaceutically acceptable addition salts, and the solvates thereof, or any subgroup thereof as mentioned in any of the other embodiments, wherein when ring A together with Y—Z forms a bicycle, this bicycle is of formula (a-1), (a-2), (a-3) or (a-4); in particular (a-1a), (a-2a), (a-3a), (a-4a), (a-4b).

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{14}$ is a 5-membered saturated heterocycle which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$; in particular wherein $R_{14}$ is a 5-membered saturated heterocycle which is substituted with one or two substituents selected from the group consisting of oxo or $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{14}$ is a 5-membered saturated heterocycle selected from 1-pyrolidinyl, 1,3-dioxolan-4-yl, 5-oxazolidinyl, 3-oxetanyl and tetrahydro-2-furanyl, each optionally substituted with one, two or three substituents selected from the group consisting of oxo, halogen, cyano, hydroxyl, $C_{1-6}$alkyloxy and $NR_{9a}R_{9b}$; in particular wherein $R_{14}$ is a 5-membered saturated heterocycle selected from 1-pyrolidinyl, 1,3-dioxolan-4-yl, 5-oxazolidinyl, 3-oxetanyl and tetrahydro-2-furanyl, each substituted with one or two substituents selected from the group consisting of oxo and $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{1a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one —$NR_{9a}R_{9b}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;

$R_{2b}$ is hydrogen or $C_{1-6}$alkyl; or $R_{2a}$ and $R_{2b}$ are taken together to form —$CH_2$—$CH_2$—, —$CH_2$—$NR_2$—, —$CH_2$—, —$CH_2$—$CH_2$—$CH_2$—, —$CH_2$—O—$CH_2$—, —$CH_2$—$CH_2$—$CH_2$—$CH_2$—, —$CH_2$—$CH_2$—$NR_{2c}$—$CH_2$—.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —$Si(CH_3)_3$; $C_{1-6}$alkyl substituted with one $R_{12}$; or $C_{1-6}$alkyloxy substituted with one $R_{12}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is $C_{1-6}$alkyl; $C_{3-6}$cycloalkyl optionally substituted with one cyano; mono- or polyhalo $C_{1-6}$alkyloxy; mono- or polyhalo$C_{1-6}$alkyl; $C_{1-4}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is $C_{1-6}$alkyl; $C_{3-6}$cycloalkyl optionally substituted with one cyano; mono- or polyhalo $C_{1-6}$alkyloxy; mono- or polyhalo$C_{1-6}$alkyl; $C_{1-4}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-; and wherein $R_8$ is other than $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein X is —$CR_1R_{1a}$—; in particular $CH_2$.

In an embodiment, the present invention relates to those compounds of formula (I) and the N-oxides, the pharmaceutically acceptable addition salts, and the solvates thereof, or any subgroup thereof as mentioned in any of the other embodiments, wherein X is covalent bond.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_1$ and $R_{1a}$ are hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein —Y—Z— is —O—$CH_2$—.

In an embodiment, the present invention relates to those compounds of formula (I) and the N-oxides, the pharmaceutically acceptable addition salts, and the solvates thereof, or any subgroup thereof as mentioned in any of the other embodiments, wherein Z is $CHR_6$, in particular $CH_2$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_3$ is hydrogen or $C_{1-6}$alkyl substituted with one or two, in particular one, hydroxyl groups.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{2a}$ and $R_{2b}$ are hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ and $R_{4b}$ are hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ and $R_{4b}$ are taken together to form =O.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_1$ and $x_3$ are CH; and $x_2$ is $CR_{5b}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_2$ is $CR_{5b}$; $R_{5b}$ is $C_{1-6}$alkyl; $C_{3-6}$cycloalkyl optionally substituted with one cyano; hydroxyl; mono- or polyhalo$C_{1-6}$alkyloxy; mono- or polyhalo $C_{1-6}$alkyl; $C_{1-4}$alkyl substituted with one or two hydroxyl groups; $C_{2-6}$alkenyl; —Si(CH$_3$)$_3$; $C_{1-6}$alkyl substituted with one $R_{12}$; $C_{1-6}$alkyl-O-carbonyl-; or $C_{1-6}$alkyloxy substituted with one $R_{12}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is $C_{1-6}$alkyl; $C_{3-6}$cycloalkyl optionally substituted with one cyano; hydroxyl; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; —Si(CH$_3$)$_3$; $C_{1-6}$alkyl substituted with one $R_{12}$; $C_{1-6}$alkyl-O-carbonyl-; or $C_{1-6}$alkyloxy substituted with one $R_{12}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups; mono- or polyhalo$C_{1-6}$alkyl; mono- or polyhalo$C_{1-6}$alkyloxy; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyloxy; $C_{1-6}$alkyloxy substituted with one or two hydroxyl groups; and $C_{1-6}$alkyloxy$C_{1-6}$alkyloxy wherein each of the $C_{1-6}$alkyl groups are optionally substituted with one or two hydroxyl groups.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{15}$ is hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{15}$ is hydrogen or F, in particular F.

In an embodiment, the present invention relates to those compounds of formula (I) and the N-oxides, the pharmaceutically acceptable addition salts, and the solvates thereof, or any subgroup thereof as mentioned in any of the other embodiments, wherein
$R_{7a}$ is hydrogen, halo, trifluoromethyl or cyano;
$R_7$ is hydrogen, —NH$_2$, —NHCH$_3$, —NH(CH$_2$CH$_3$), methyl, —CH$_2$OH, halo or cyano.

In an embodiment, the present invention relates to those compounds of formula (I) and the N-oxides, the pharmaceutically acceptable addition salts, and the solvates thereof, or any subgroup thereof as mentioned in any of the other embodiments, wherein
$R_{7a}$ is hydrogen;
$R_7$ is hydrogen, —NH$_2$, —CH$_2$OH, halo or cyano; in particular $R_7$ is hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl optionally substituted with one or two $R_8$ substituents;
each $R_8$ is independently hydrogen; $C_{1-4}$alkyloxy; cyano; or halo;
Y is —O—; Z is —CH$_2$—; $R_{15}$ is H; $x_1$ and $x_3$ are CH; $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein
$y_1$ and $y_2$ are CH; $R_7$ is H; X is a covalent bond; $R_{2a}$ and $R_{2b}$ are H;
$R_{4a}$ and $R_{4b}$ are H;
ring A is phenyl optionally substituted with one or two $R_8$ substituents;
each $R_8$ is independently hydrogen; $C_{1-4}$alkyloxy; cyano; or halo;
Y is —O—; Z is —CH$_2$—; $R_{15}$ is H; $x_1$ and $x_3$ are CH; $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein
$y_1$ and $y_2$ are CH; $R_7$ is H; X is a covalent bond; $R_{2a}$ and $R_{2b}$ are H;
$R_{4a}$ and $R_{4b}$ are H; ring A is phenyl;
Y is —O—; Z is —CH$_2$—; $R_{15}$ is H; $x_1$ and $x_3$ are CH; $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_1$ and $x_3$ are CH; $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $y_1$ and $y_2$ are CH.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_8$ is hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_8$ is not taken together with the $R_6$ substituent of Z to form a bicycle.

In an embodiment, the present invention relates to a subgroup of formula (I) as defined in the general reaction schemes.

All possible combinations of the above-indicated embodiments are considered to be embraced within the scope of this invention.

Whenever possible, any interesting embodiment for the compounds of formula (I) as listed hereinabove, also holds for the compounds of formula (I').

In an embodiment, the present invention concerns novel compounds of Formula (I'), tautomers and stereoisomeric forms thereof, wherein $y_1$ is $CR_{7a}$ or N;
$y_2$ is CH or N;
$R_{7a}$ is hydrogen, halo, trifluoromethyl or cyano;
$R_7$ is hydrogen, —$NH_2$, —$NHCH_3$, —$NH(CH_2CH_3)$, methyl, —$CH_2OH$, halo or cyano;
or when $y_1$ represents $CR_{7a}$, this $R_{7a}$ can be taken together with a $R_7$ on an adjacent carbon atom to form —CH=CH—NH— or —N=CH—NH—;
X is —$CR_{1a}$—;
$R_{1a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one —$NR_{9a}R_{9b}$; —C(=O)—$NR_{9a}R_{9b}$; or $C_{1-6}$alkyl-O-carbonyl-;
$R_{2a}$ is hydrogen; $C_{1-6}$alkyl; mono- or polyhalo$C_{1-6}$alkyl; $C_{1-6}$alkyl substituted with one or two hydroxyl groups; $C_{1-6}$alkyloxycarbonyl; or $C_{1-6}$alkyl substituted with one substituent selected from the group consisting of —$NR_{9a}R_{9b}$, cyano and $C_{1-4}$alkyloxy;
$R_{4a}$ is hydrogen; halo; $C_{1-6}$alkyl; mono- or polyhalo $C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo$C_{1-6}$alkylcarbonyl-; $R_{10a}R_{10b}N$—$C_{1-6}$alkylcarbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one —$NR_{10a}R_{10b}$; $C_{2-6}$alkenyl; $C_{2-6}$alkynyl; hydroxy$C_{2-6}$alkenyl; hydroxy$C_{2-6}$alkynyl; $C_{1-6}$alkyloxy$C_{2-6}$alkenyl;
$C_{1-6}$alkyloxy$C_{2-6}$alkynyl; $C_{2-6}$alkenyl substituted with one —$NR_{10a}R_{10b}$; $C_{2-6}$alkynyl substituted with one —$NR_{10a}R_{10b}$; $C_{1-6}$alkyl substituted with one or two hydroxyl groups and one —$NR_{10}R_{10b}$; —$C_{1-6}$alkyl-C($R_{13}$)=N—O—$R_{13}$; —S(=O)$_2$—$C_{1-6}$alkyl; —S(=O)$_2$—$NR_{9a}R_{9b}$;
$C_{1-6}$alkyl substituted with one —(C=O)—$R_{14}$; $C_{1-6}$alkyl substituted with one or two hydroxyl groups and one $R_{14}$; $C_{1-6}$alkyl substituted with one $R_{14}$; $C_{2-6}$alkenyl substituted with one $R_{14}$; $C_{2-6}$alkynyl substituted with one $R_{14}$; or $R_{14}$;
$R_{4b}$ and $R_3$ are taken together to form a bond; or
$R_{4a}$ and $R_{4b}$ together form =O, in which case $R_3$ is hydrogen;
Y is —O— or —C(=O)—;
Z is —$CHR_6$— or —$CH_2$—C≡C—;

$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —$NR_{9a}R_{9b}$; or —C(=O)—$NR_{9a}R_{9b}$;
Ring A is phenyl or a 6 membered saturated, partially saturated or aromatic heterocyclyl, said heterocyclyl containing one or two nitrogen atoms; wherein the phenyl or the heterocyclyl is optionally substituted with one or two $R_8$ substituents; each $R_8$ is independently hydrogen; $C_{1-4}$alkyloxy; hydroxyl; cyano; or halo;
$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;
$R_{10a}$ and $R_{10b}$ each independently represent hydrogen; $C_{1-4}$alkyl; cyano$C_{1-6}$alkyl; $C_{1-6}$alkyl substituted with one $NR_{9a}R_{9b}$; $C_{1-6}$alkyl substituted with one —C(=O)—$NR_{9a}R_{9b}$; $C_{1-6}$alkyloxy optionally substituted with one or two hydroxyl groups;
$C_{1-6}$alkyloxy$C_{1-6}$alkyl wherein each $C_{1-6}$alkyl is optionally substituted with one or two hydroxyl groups; $R_{14}$; $C_{1-6}$alkyl substituted with one $R_{14}$; —(C=O)—$R_{14}$;
$C_{1-6}$alkylcarbonyl-; $C_{1-6}$alkyl-O-carbonyl-; mono- or polyhalo$C_{1-6}$alkylcarbonyl-substituted with one or two hydroxyl groups; mono- or polyhalo$C_{1-6}$alkyl substituted with one or two hydroxyl groups; mono- or polyhalo$C_{1-6}$alkylcarbonyl-; $C_{1-6}$alkyl substituted with one —Si(CH$_3$)$_3$; —S(=O)$_2$—$C_{1-6}$alkyl optionally substituted with one or more halo substituents; —S(=O)$_2$—$NR_{9a}R_{9b}$;
$C_{1-6}$alkyl substituted with one —S(=O)$_2$—$C_{1-6}$alkyl wherein —S(=O)$_2$—$C_{1-6}$alkyl is optionally substituted with one or more halo substituents;
$C_{1-6}$alkyl substituted with one —S(=O)$_2$—$NR_{9a}R_{9b}$;
$C_{1-6}$alkyl substituted with one —NH—S(=O)$_2$—$C_{1-6}$alkyl wherein NH—S(=O)$_2$—$C_{1-6}$alkyl is optionally substituted on a carbon atom with one or more halo substituents;
$C_{1-6}$alkyl substituted with one —NH—S(=O)$_2$—$NR_{9a}R_{9b}$;
mono- or polyhalo$C_{1-4}$alkyl; or $C_{1-4}$alkyl substituted with one or two hydroxyl groups;
$R_{11}$ is cyano, —$NR_{10a}R_{10b}$; $C_{1-6}$alkyloxy optionally substituted with one or two hydroxyl groups; —S(=O)$_2$—$C_{1-6}$alkyl; —S(=O)$_2$—$NR_{9a}R_{9b}$; —$NR_{13}$—S(=O)$_2$—$C_{1-6}$alkyl; —$NR_{13}$—S(=O)$_2$—$NR_{9a}R_{9b}$; $C_{1-6}$alkylcarbonyloxy-; —C(=O)—$NR_{10a}R_{10b}$; —O—C(=O)—$NR_{10a}R_{10b}$; —COOH, —P(=O)(OH)$_2$; or —P(=O)(O—$C_{1-4}$alkyl)$_2$;
$R_{12}$ is —$NR_{9a}R_{9b}$, $C_{1-6}$alkyloxy, or cyano;
$R_{13}$ is hydrogen or $C_{1-4}$alkyl;
$R_{14}$ is a $C_{3-8}$cycloalkyl; or a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$;
$x_1$ is $CR_{5a}$ or N;
$x_2$ is $CR_{5b}$ or N;
$x_3$ is $CR_{5c}$ or N;
each $R_{15}$ is independently selected from the group consisting of hydrogen, methyl, halo, $C_{1-4}$alkyloxy and hydroxyl;
$R_{5a}$ and $R_{5c}$ each independently are selected from the group consisting of hydrogen; hydroxyl; cyano; halo;

$C_{1-6}$alkyl; $C_{1-6}$alkyl substituted with one or two hydroxyl groups; mono- or polyhalo$C_{1-6}$alkyl; mono- or polyhalo$C_{1-6}$alkyloxy; $C_{1-6}$alkyl substituted with one —$NR_{9a}R_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —$NR_{9a}R_{9b}$;

$R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —$Si(CH_3)_3$; $C_{1-6}$alkyl substituted with one $R_{12}$; $C_{1-6}$alkyl-O-carbonyl-; or $C_{1-6}$alkyloxy substituted with one $R_{12}$;

and the N-oxides, the pharmaceutically acceptable addition salts, and the solvates thereof.

In an embodiment, the present invention concerns novel compounds of Formula (I'), tautomers and stereoisomeric forms thereof, wherein $y_1$ is CH; $y_2$ is CH;
$R_7$ is hydrogen;
X is —$CR_{1a}$—;
$R_{1a}$ is hydrogen; —C(=O)—$NR_{9a}R_{9b}$; or $C_{1-6}$alkyl-O-carbonyl-;
$R_{2a}$ is hydrogen;
$R_{4a}$ is hydrogen; halo; $C_{1-6}$alkyl; or $C_{1-6}$alkyl-O-carbonyl-;
$R_{4b}$ and $R_3$ are taken together to form a bond; or
$R_{4a}$ and $R_{4b}$ together form =O, in which case $R_3$ is hydrogen;
Y is —O—; Z is —$CHR_6$—; $R_6$ is hydrogen;
Ring A is phenyl optionally substituted with one or two $R_8$ substituents;
each $R_8$ is independently hydrogen; or halo;
$R_{9a}$ and $R_{9b}$ each independently represent hydrogen; or $C_{1-4}$alkyl;
$x_1$ is $CR_{5a}$; $x_2$ is $CR_{5b}$; $x_3$ is $CR_{5c}$;
each $R_{15}$ is hydrogen;
$R_{5a}$ and $R_{5c}$ are hydrogen; $R_{5b}$ is $C_{1-6}$alkyl;
and the N-oxides, the pharmaceutically acceptable addition salts, and the solvates thereof.

Another embodiment of the present invention relates to those compounds of formula (I') and the N-oxides, the pharmaceutically acceptable addition salts, and the solvates thereof, or any subgroup thereof as mentioned in any of the other embodiments wherein one or more of the following restrictions apply:

(i) $y_1$ is CH;
(ii) $y_2$ is CH;
(iii) $R_7$ is hydrogen;
(iv) X is —$CR_{1a}$—;
(v) $R_{1a}$ is hydrogen; —C(=O)—$NR_{9a}R_{9b}$; or $C_{1-6}$alkyl-O-carbonyl-;
(vi) $R_{2a}$ is hydrogen;
(vii) $R_{4a}$ is hydrogen; halo; $C_{1-6}$alkyl; $C_{1-6}$alkyl-O-carbonyl-;
$R_{4b}$ and $R_3$ are taken together to form a bond; or
$R_{4a}$ and $R_{4b}$ together form =O, in which case $R_3$ is hydrogen;
(viii) Ring A is phenyl optionally substituted with one or two $R_8$ substituents;
(ix) each $R_8$ is independently hydrogen; or halo;
(x) $R_{9a}$ and $R_{9b}$ each independently represent hydrogen; or $C_{1-4}$alkyl;
(xi) Y is —O—;
(xii) Z is —$CHR_6$—;
(xiii) $R_6$ is hydrogen;
(xiv) $x_1$ is $CR_{5a}$; $x_2$ is $CR_{5b}$; $x_3$ is $CR_{5c}$;
(xv) each $R_{15}$ is hydrogen;
(xvi) $R_{5a}$ and $R_{5c}$ are hydrogen;
(xvii) $R_{5b}$ is $C_{1-6}$alkyl.

In an embodiment, the present invention relates to those compounds of formula (I') and the N-oxides, the pharmaceutically acceptable addition salts, and the solvates thereof, or any subgroup thereof as mentioned in any of the other embodiments, wherein $R_{4b}$ and $R_3$ are taken together to form a bond; or $R_{4a}$ and $R_{4b}$ together form =O, in which case $R_3$ is hydrogen.

In an embodiment, the present invention relates to those compounds of formula (I') and the N-oxides, the pharmaceutically acceptable addition salts, and the solvates thereof, or any subgroup thereof as mentioned in any of the other embodiments, wherein $R_{4b}$ and $R_3$ are taken together to form a bond.

In an embodiment, the present invention relates to those compounds of formula (I') and the N-oxides, the pharmaceutically acceptable addition salts, and the solvates thereof, or any subgroup thereof as mentioned in any of the other embodiments, wherein $R_{4a}$ and $R_{4b}$ together form =O, and $R_3$ is H.

In an embodiment, the present invention relates to those compounds of formula (I') and the N-oxides, the pharmaceutically acceptable addition salts, and the solvates thereof, or any subgroup thereof as mentioned in any of the other embodiments, wherein $R_{2a}$ is hydrogen;
$R_{4a}$ is hydrogen; halo; $C_{1-6}$alkyl;
$R_{4b}$ and $R_3$ are taken together to form a bond; or
$R_{4a}$ and $R_{4b}$ together form =O, in which case $R_3$ is hydrogen.

In an embodiment, the present invention relates to a subgroup of formula (I') as defined in the general reaction schemes.

All possible combinations of the above-indicated embodiments are considered to be embraced within the scope of this invention.

Methods for the Preparation of Compounds of Formula (I) and Formula (I')

In this section, as in all other sections unless the context indicates otherwise, references to formula (I) and (I') also include all other sub-groups and examples thereof as defined herein.

The general preparation of some typical examples of the compounds of Formula (I) and (I') is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice.

The skilled person will realize that in the reactions described in the Schemes, it may be advisable or necessary to perform the reaction under an inert atmosphere, such as for example under N₂-gas atmosphere, for example when NaH is used in the reaction.

It will be apparent for the skilled person that it may be necessary to cool the reaction mixture before reaction workup (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that intermediates and final compounds shown in the schemes below may be further functionalized according to methods well-known by the person skilled in the art.

All variables are defined as mentioned hereabove unless otherwise is indicated or is clear from the context.

1) Scheme 1:

In general, compounds of formula (Ia-Ie) can be prepared according to reaction Scheme 1. In scheme 1 the following definitions apply:

Ring A1' is optionally substituted phenyl or an optionally substituted 6-membered aromatic heterocycle containing one or two nitrogen atoms, but $R_8$ is not taken together with the $R_6$ substituent of Z (does not form a bicyclic ring);

R' and R'' are functional groups within the limits of the scope;

Et means ethyl and Ph means phenyl;

and all other variables in Scheme 1 are defined according to the scope of the present invention.

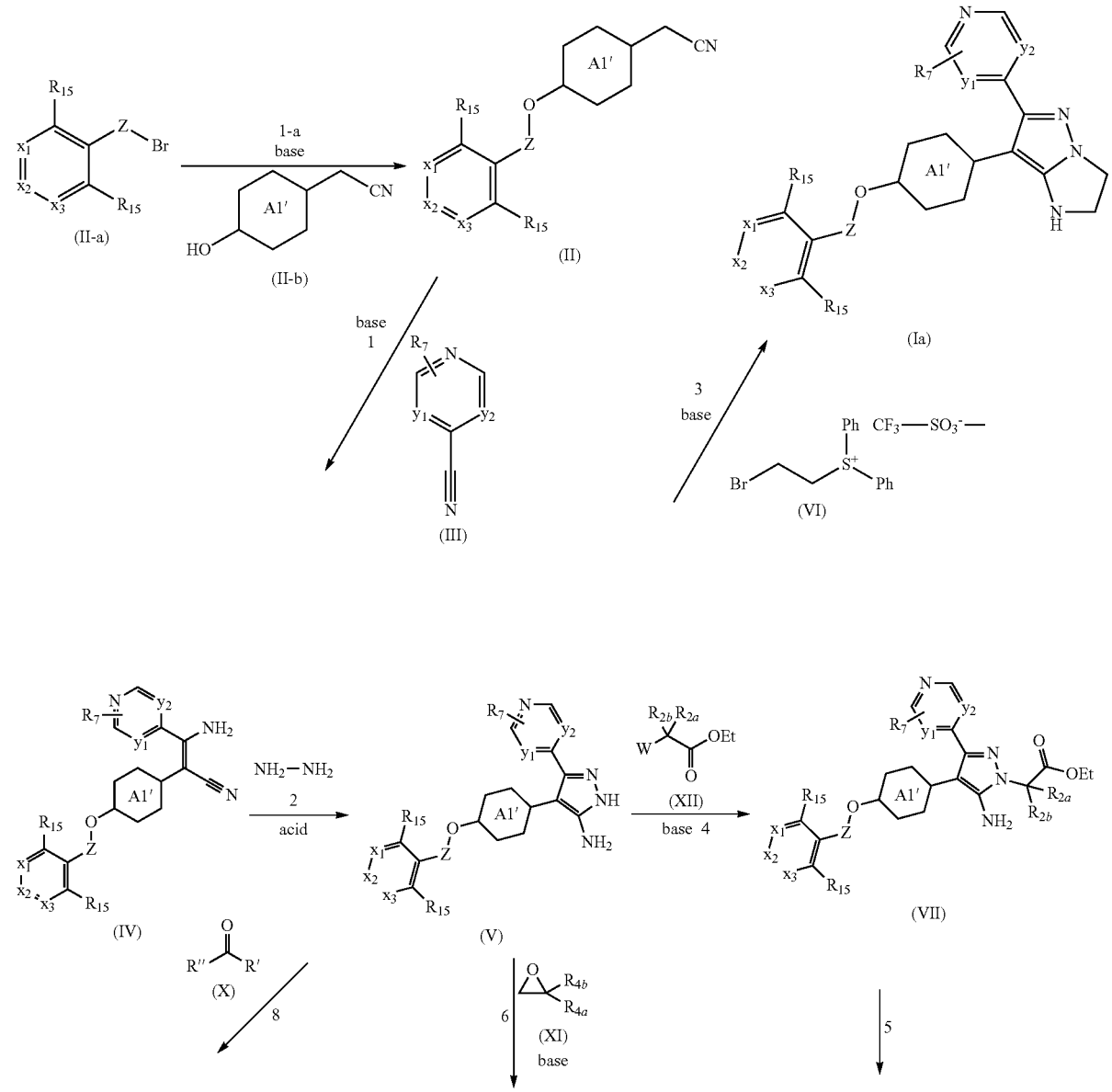

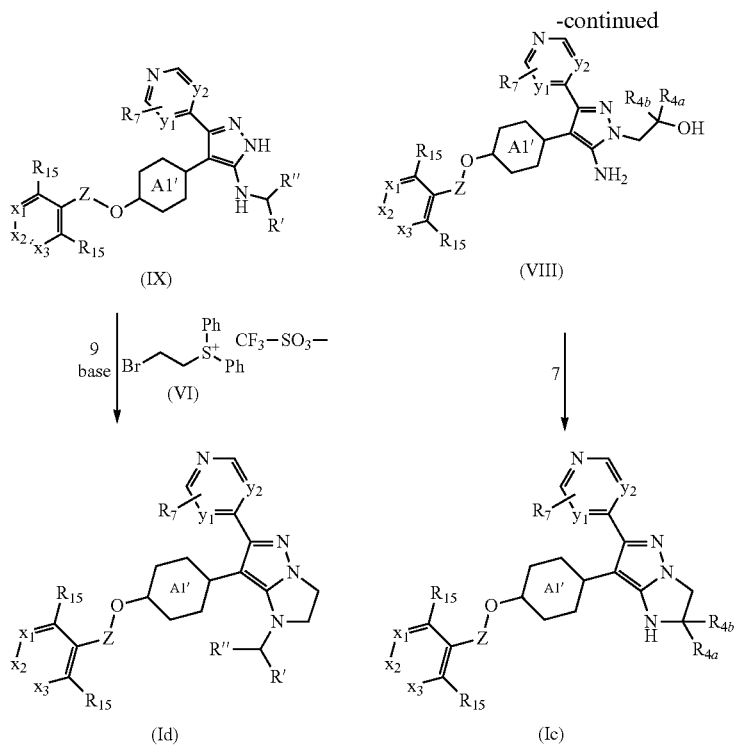
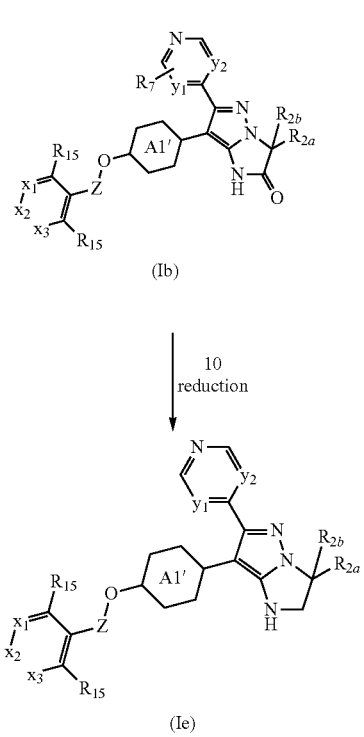

1a: In the presence of a suitable base, such as for example $K_2CO_3$, and a suitable solvent, such as for example $CH_3CN$.
1: an intermediate of formula (II) can be reacted with an intermediate of formula (III) in the presence of a suitable base, such as for example potassium 2-methyl-2-butoxide, and a suitable solvent, such as for example tetrahydrofuran (THF), resulting in an intermediate of formula (IV).
2: an intermediate of formula (IV) can be reacted with hydrazine monohydrate in the presence of a suitable acid, such as for example acetic acid (AcOH), and a suitable solvent, such as for example ethanol (EtOH), resulting in an intermediate of formula (V).
3: an intermediate of formula (V) can be reacted with a reagent of formula (VI) in the presence of a suitable base, such as for example diisopropylethylamine (DIPEA), and a suitable solvent, such as for example N,N-dimethylformamide (DMF), resulting in a compound of formula (Ia).
4: an intermediate of formula (V) can be reacted with an intermediate of formula (XII), wherein W represents a suitable leaving group, such as for example iodide, bromide, chloride or tosylate, in the presence of a suitable base, such as for example NaH, and a suitable solvent, such as for example DMF, resulting in an intermediate of formula (VII).
5: an intermediate of formula (VII) can be reacted with a suitable base, such as for example KOH, in the presence of a suitable solvent or solvent mixture, such as for example EtOH and water. The resulting intermediate can be converted into a compound of formula (Ib) by reaction with suitable peptide coupling reagents, such as for example 1-hydroxy-benzotriazole (HOBt) and 1-(3-dimethylaminopropyl)-3-ethylcarbodiimide HCl (EDCI), a suitable base, such as for example triethylamine ($Et_3N$), and a suitable solvent, such as for example N,N-dimethylformamide (DMF).
6: an intermediate of formula (V) can be reacted with an intermediate of formula (XI), in the presence of a suitable base, such as for example $K_2CO_3$, and a suitable solvent, such as for example DMF, resulting in an intermediate of formula (VIII).
7: an intermediate of formula (VIII) can be converted into a compound of formula (Ic) by reaction with methanesulfonylchloride in the presence of a suitable base, such as for example $Et_3N$, and a suitable solvent, such as for example $CH_3CN$.
8: an intermediate of formula (V) can be reacted with an intermediate of formula (X), in the presence of a suitable reducing agent, such as for example Sodium Triacetoxyborohydride ($NaBH(OAc)_3$), and a suitable solvent, such as for example 1,2-dichloroethane (DCE), resulting in an intermediate of formula (IX).
9: an intermediate of formula (IX), can be converted into a compound of formula (Id) by reaction with a reagent of formula (VI) in the presence of a suitable base, such as for example DIPEA, and a suitable solvent, such as for example DMF.
10: a compound of formula (Ib) can be converted into a compound of formula (Ie) by reaction with $LiAlH_4$ in the presence of a suitable solvent, such as for example THF.

2) Scheme 2: Second Way Final Compounds (I):
Compounds of formula (Ia-a), (Ic-a) and (Ib-a) can be prepared according to the following reaction scheme 2.
In scheme 2 the following definitions apply:
$Y_x$ is defined as O, and ring A1 is phenyl or a 6-membered aromatic heterocycle containing one or two nitrogen atoms; wherein the phenyl or the heterocycle is optionally substituted with one or two $R_8$ substituents;

each $R_8$ is independently hydrogen; $C_{1-4}$alkyloxy; hydroxyl; cyano; $C_{1-4}$alkyl or halo; or a $R_8$ substituent of ring A1 on an atom adjacent to the atom carrying the $Y_x$—Z substituent is taken together with the $R_6$ substituent of Z to form a bicyclic ring;
and all other variables in Scheme 2 are defined as mentioned before.

example potassium 2-methyl-2-butoxide, and a suitable solvent, such as for example THF, resulting in an intermediate of formula (XIV).

2: an intermediate of formula (XIV) can be reacted with an intermediate of formula (XV) in the presence of a suitable acid, such as for example HCl, and a suitable

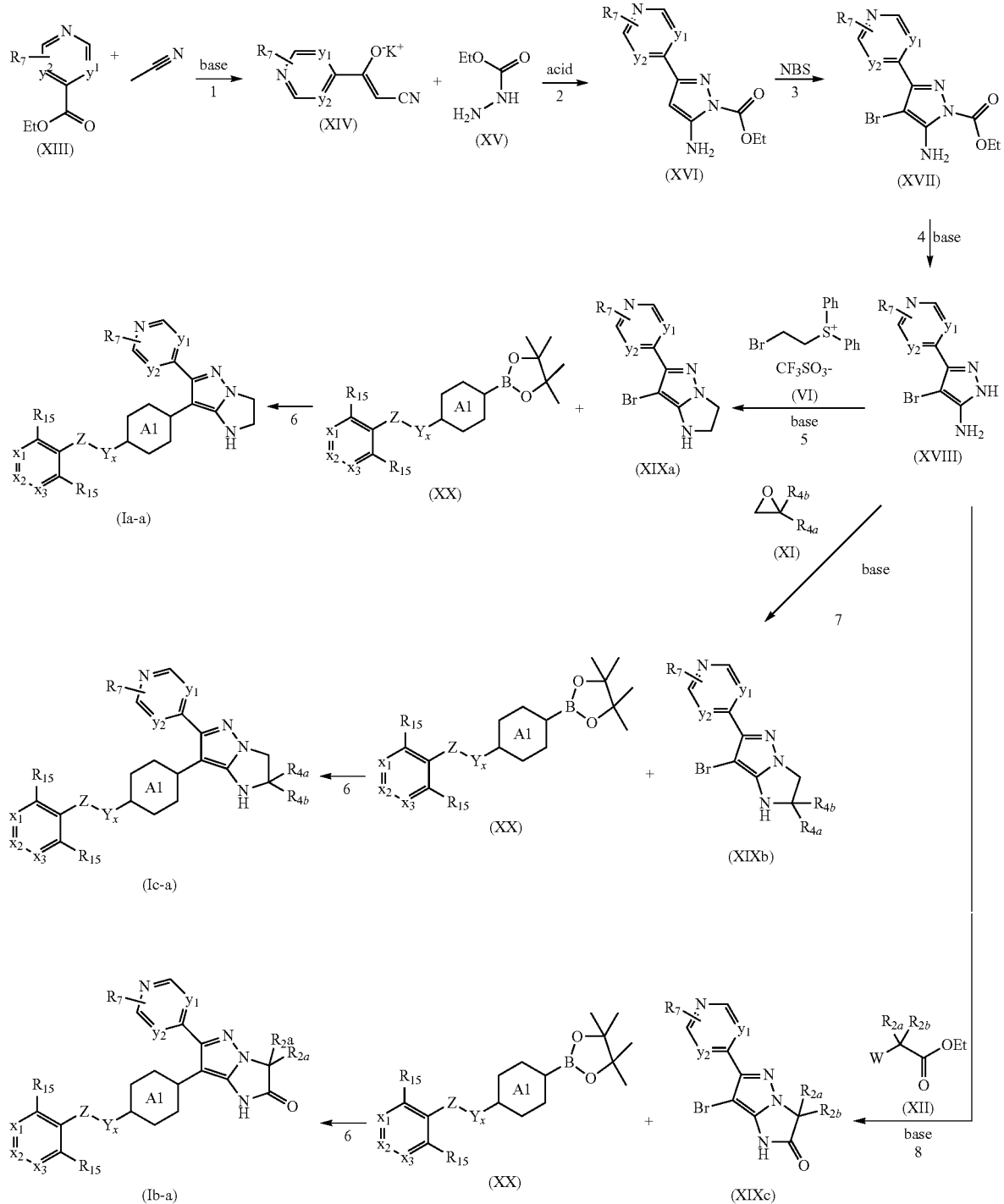

1: an intermediate of formula (XIII) can be reacted with $CH_3CN$ in the presence of a suitable base, such as for solvent, such as for example EtOH, resulting in an intermediate of formula (XVI).

3: an intermediate of formula (XVI) can be converted into an intermediate of formula (XVII) by reaction with N-bromosuccinimide (NBS) in the presence of a suitable solvent, such as for example DCM.
4: an intermediate of formula (XVII) can be converted into an intermediate of formula (XVIII) by reaction with a suitable base, such as for example Et$_3$N, in the presence of a suitable solvent, such as for example methanol (MeOH).
5: an intermediate of formula (XVIII) can be reacted with an intermediate of formula (VI) in the presence of a suitable base, such as for example DIPEA, and a suitable solvent, such as for example DMF, resulting in an intermediate of formula (XIXa).
6: an intermediate of formula (XIXa), (XIXb) or (XIXc) can be reacted with an intermediate of formula (XX)) in the presence of suitable catalyst, such as for example Pd$_2$dba$_3$, a suitable ligand, such as for example tris(1,1-dimethylethyl)-phosphine, tetrafluoroborate(1-) (1:1) (also tri-tert-butylphosphonium tetrafluoroborate) (P(tBu)$_3$.HBF$_4$), a suitable base, such as potassium phosphate (K$_3$PO$_4$), and a suitable solvent or solvent mixture, such as for example dioxane and water, resulting in a compound of formula (Ia-a), (Ic-a) or (Ib-a) respectively.
7: an intermediate of formula (XVIII) can be reacted with an intermediate of formula (XI), in the presence of a suitable base, such as for example K$_2$CO$_3$, and a suitable solvent, such as for example DMF. The resulting intermediate can be converted into an intermediate of formula (XIXb) by reaction with methanesulfonylchloride in the presence of a suitable base, such as for example Et$_3$N, and a suitable solvent, such as for example CH$_3$CN.
8: an intermediate of formula (XVIII) can be reacted with an intermediate of formula (XII), wherein W represents a suitable leaving group, such as for example iodide, bromide, chloride or tosylate, in the presence of a suitable base, such as for example NaH, and a suitable solvent, such as for example DMF.

The resulting intermediate can be reacted with a suitable base, such as for example KOH, in the presence of a suitable solvent or solvent mixture, such as for example ethanol (EtOH) and water. The resulting intermediate can be converted into a compound of formula (XIXc) by reaction with suitable peptide coupling reagents, such as for example 1-hydroxy-benzotriazole (HOBt) and 1-(3-dimethylaminopropyl)-3-ethylcarbodiimide HCl (EDCI), a suitable base, such as for example Et$_3$N, and a suitable solvent, such as for example DMF.

3) Scheme 2a: Intermediate (Y$_x$=O)

Intermediates of formula (XX) wherein Y$_x$ is O and ring A1 is limited to A1' (no bicycles formed), hereby named an intermediate of formula (XXa) can be prepared according to the following reaction scheme 2a, wherein all variables are as defined before.

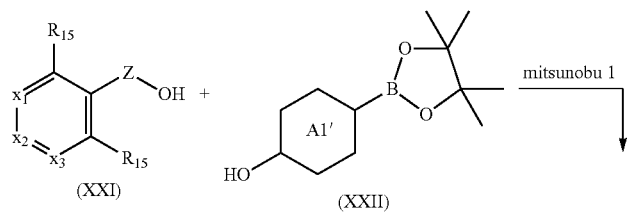

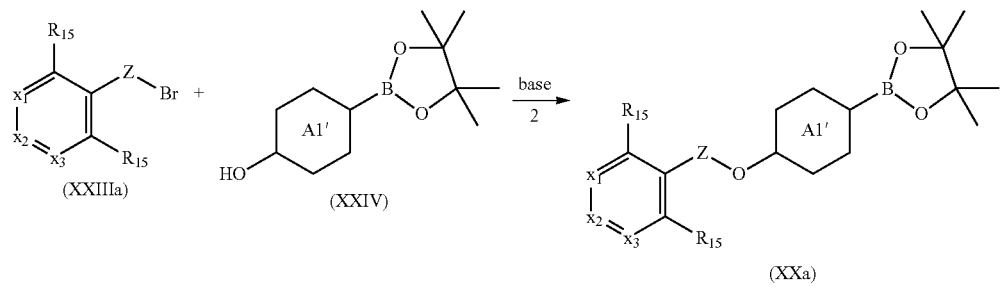

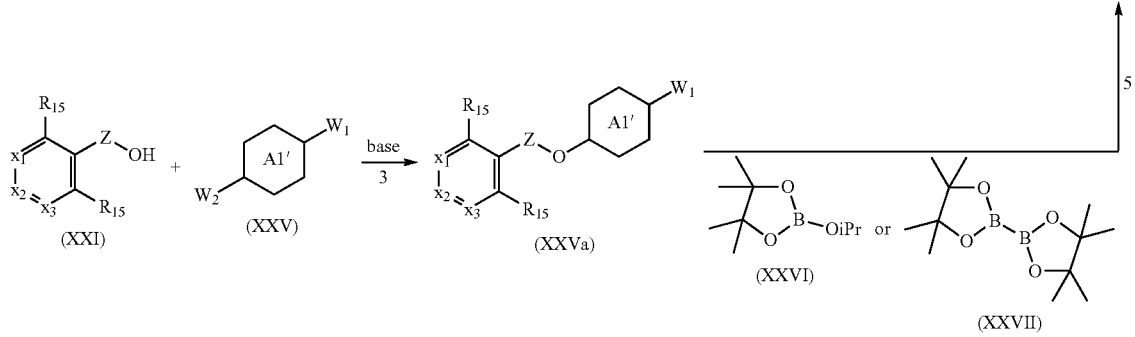

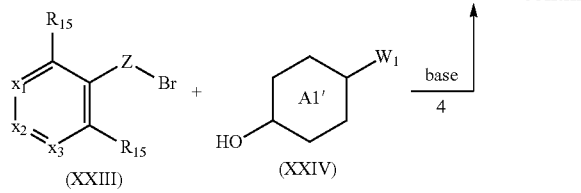

1: an intermediate of formula (XXI) can be reacted with an intermediate of formula (XXII) in the presence of Triphenylphosphine (PPh₃), a suitable Mitsunobu reagent, such as for example DBAD and a suitable solvent, such as for example Dichloromethane (DCM) or THF, resulting in an intermediate of formula (XXa).
2: an intermediate of formula (XXIIIa) can be reacted with an intermediate of formula (XXIV) in the presence of a suitable base, such as for example $K_2CO_3$ or $Ag_2CO_3$, and a suitable solvent, such as for example $CH_3CN$ or DMF, resulting in an intermediate of formula (XXa)
3: an intermediate of formula (XXI) can be reacted with an intermediate of formula (XXV), wherein $W_1$ represents a suitable halogen, such as for example iodide or bromide, and wherein $W_2$ represents a suitable leaving group, such as for example chloride, fluoride or bromide, in the presence of a suitable base, such as for example Sodium hydride (NaH) and a suitable solvent, such as for example DMF, resulting in an intermediate of formula (XXVa).

4: an intermediate of formula (XXIII) can be reacted with an intermediate of formula (XXIV), wherein W1 represents a suitable halogen, such as for example iodide or bromide, in the presence of a suitable base, such as for example $K_2CO_3$ or $Ag_2CO_3$, and a suitable solvent, such as for example $CH_3CN$ or DMF, resulting in an intermediate of formula (XXVa).
5: an intermediate of formula (XXVa) can be reacted with intermediates of formula (XXVI) or (XXVII) in the presence of a suitable base, such as for example nBuLi or Potassium acetate (AcOK), and a suitable solvent, such as for example THF or dioxane resulting in an intermediate of formula (XXa).

4) Scheme 2b: Intermediate (Bicycle)

Intermediates of formula (XX) wherein $Y_x$—Z forms a bicycle with ring A1 as shown in intermediates of formula (XXb), (XXc), (XXd) can be prepared according to the following reaction scheme 2b-1. In scheme 2b-1, all variables are as defined before:

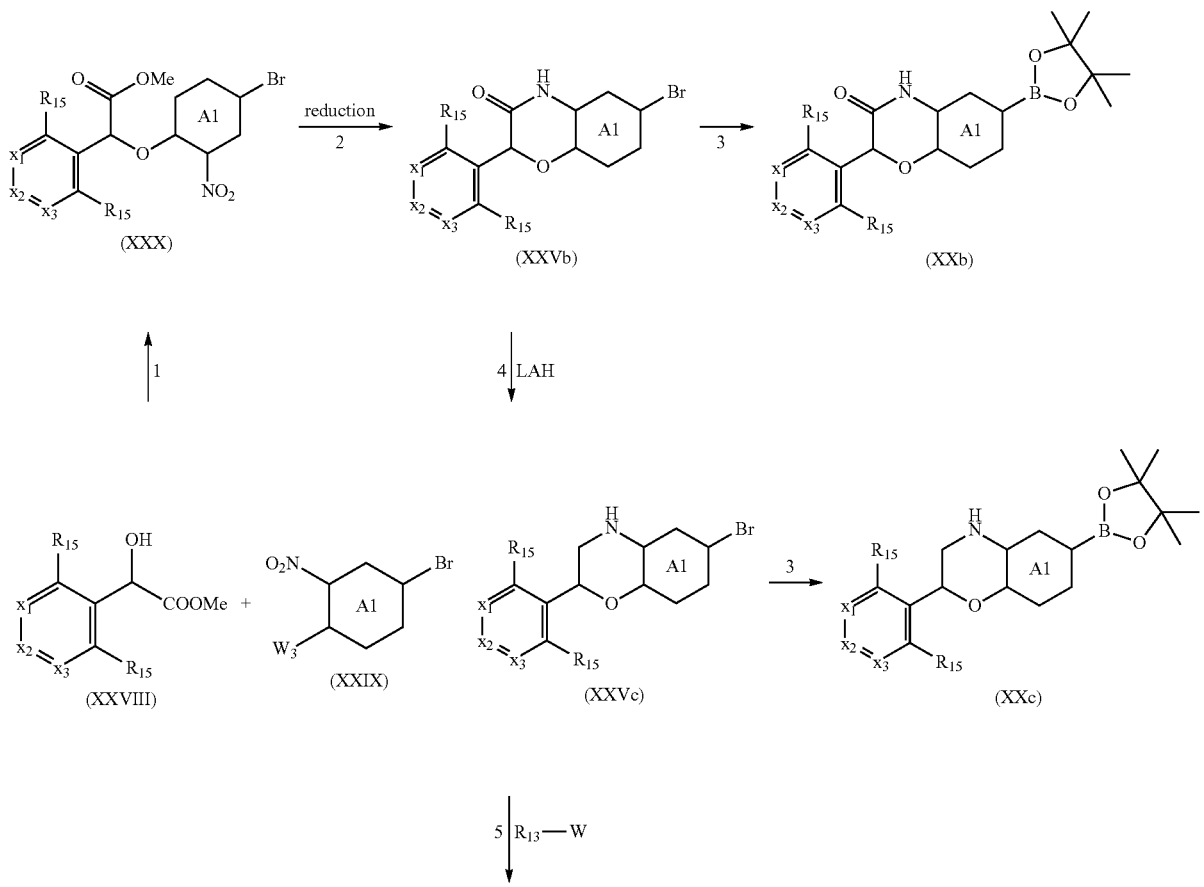

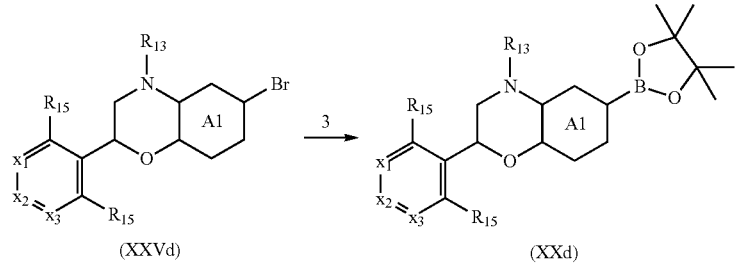

1: an intermediate of formula (XXVIII) can be reacted with an intermediate of formula (XXIX), wherein $W_3$ represents an hydroxyl, in the presence of triphenylphosphine ($PPh_3$), a suitable Mitsunobu reagent, such as for example di-tut-butyl azodicarboxylate (DBAD) and a suitable solvent, such as for example THF resulting in an intermediate of formula (XXX).

An intermediate of formula (XXVIII) can also be reacted with an intermediate of formula (XXIX), wherein $W_3$ represents a bromide, in the presence of a suitable base, such as for example Sodium hydride (NaH) and a suitable solvent, such as for example THF resulting in an intermediate of formula (XXX).

2: an intermediate of formula (XXX) can be converted into an intermediate of formula (XXVb) by reaction with Fe in the presence of a suitable solvent, such as for example acetic acid (AcOH).

3: An intermediate of formula (XXVb), (XXVc) or (XXVd) can be reacted with Bis(pinacolato)diboron in the presence of a suitable base, such as for example AcOK, a suitable catalyst, such as for example [1,1'-bis(diphenylphosphino-kP)ferrocene]dichloropalladium ($PdCl_2(dppf)$) and a suitable solvent, such as for example 1,2-dimethoxyethane (DME) resulting in an intermediate of formula (XXb), (XXc) or (XXd) respectively.

4: an intermediate of formula (XXVb) can be reduced in an intermediate of formula (XXVc) by reaction with LAH in the presence of a suitable solvent, such as for example THF.

5: an intermediate of formula (XXVc) can reacted with an intermediate of formula $R_{13}$—W, wherein W represents a suitable leaving group, such as for example iodide, in the presence of a suitable base, such as for example $K_2CO_3$ and a suitable solvent, such as for example DMF, resulting in an intermediate of formula (XXVd).

Intermediates of formula (XX) wherein $Y_x$—Z forms a bicycle with ring A1 as shown in an intermediate of formula (XXf) can be prepared according to the following reaction scheme 2b-2. In scheme 2b-2, all variables are as defined before:

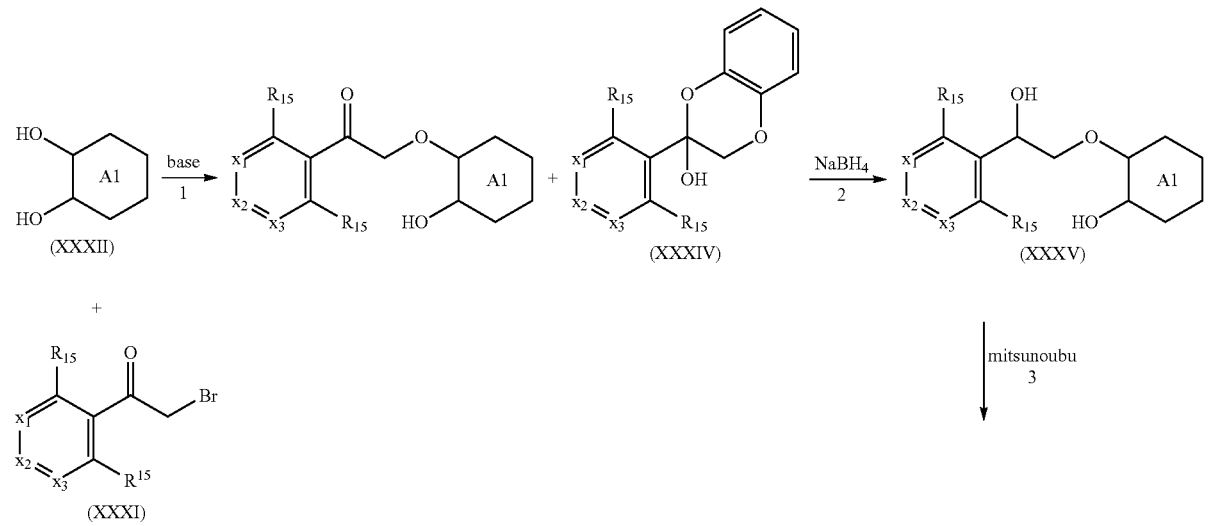

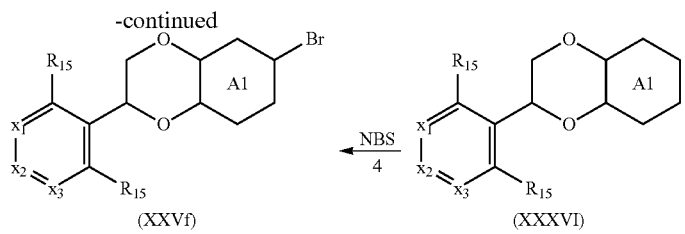

(XXVf) ← NBS, 4 — (XXXVI)

↓ 5

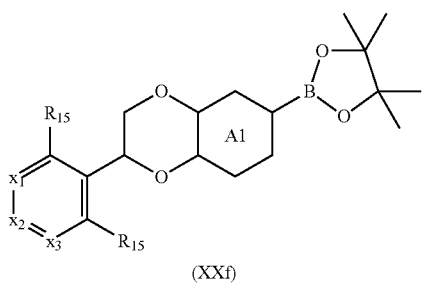

(XXf)

1: an intermediate of formula (XXXI) can reacted with an intermediate of formula (XXXII) in the presence of a suitable base, such as for example Et₃N, and a suitable solvent, such as for example iPrOH, resulting in a mixture of intermediate of formula (XXXIII) and an intermediate of formula (XXXIV).
2: a mixture of intermediate of formula (XXXIII) and intermediate of formula (XXXIV) can be converted into an intermediate of formula (XXXV) by reaction with NaBH₄ in the presence of a suitable solvent or solvent mixture, such as for example THF and MeOH.
3: an intermediate of formula (XXXV) can be converted into an intermediate of formula (XXXVI) by reaction with PPh₃, a suitable Mitsunobu reagent, such as for example DBAD and a suitable solvent, such as for example DCM.
4: an intermediate of formula (XXXVI) can reacted with NBS in the presence of a suitable solvent, such as for example AcOH, resulting in an intermediate of formula (XXVf).
5: An intermediate of formula (XXVf) can be reacted with Bis(pinacolato)diboron in the presence of a suitable base, such as for example AcOK, a suitable catalyst, such as for example PdCl₂(dppf) and a suitable solvent, such as for example 1,2-dimethoxyethane resulting in an intermediate of formula (XXf) respectively.

Intermediates of formula (XX) wherein $Y_x$—Z forms a bicycle with ring A1 as shown in an intermediate of formula (XXg) can be prepared according to the following reaction scheme 2b-3. In scheme 2b-3, all variables are as defined before:

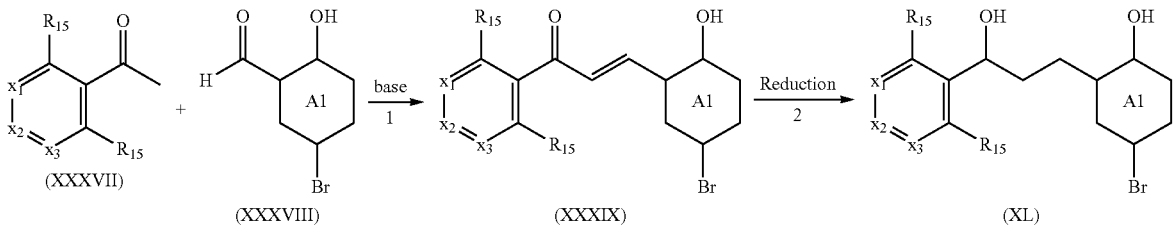

↓ mitsunobu 3

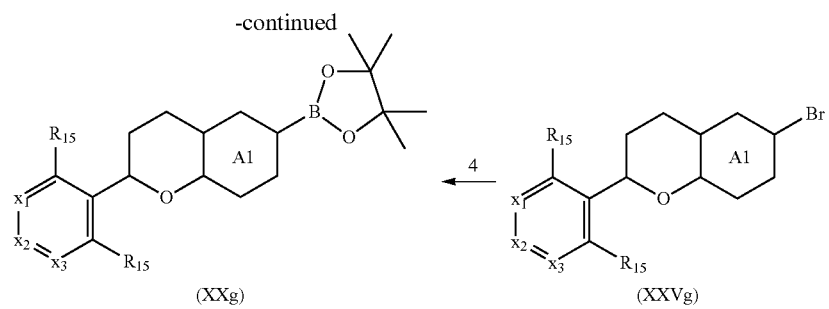

1: an intermediate of formula (XXXVII) can be reacted with an intermediate of formula (XXXVIII) in the presence of a suitable base, such as for example KOH, and a suitable solvent, such as for example EtOH, resulting in an intermediate of formula (XXXIX).
2: an intermediate of formula (XXXIX) can be converted into an intermediate of formula (XL) by reaction with NaBH$_4$ in the presence of Indium Chloride and a suitable solvent, such as for example Acetonitrile.
3: an intermediate of formula (XL) can be converted into an intermediate of formula (XXVg) by reaction with PPh$_3$, a suitable Mitsunobu reagent, such as for example DBAD and a suitable solvent, such as for example DCM.
4: An intermediate of formula (XXVg) can be reacted with Bis(pinacolato)diboron in the presence of a suitable base, such as for example AcOK, a suitable catalyst, such as for example PdCl$_2$(dppf) and a suitable solvent, such as for example 1,2-Dimethoxyethane resulting in an intermediate of formula (XXg).

5) Scheme 2c: Intermediates of Formula (XXh) (Y is Carbonyl)

By preparing derivatives of intermediates of formula (XX) wherein the general Y definition is carbonyl, hereby named an intermediate of formula (XXh), more compounds of formula (I) can be prepared by using analogous reaction protocols as described above or below and/or reaction protocols known by the skilled person. Such an intermediate of formula (XXh) can be prepared according to the following reaction scheme 2c, wherein ring A1' is optionally substituted phenyl or an optionally substituted 6-membered aromatic heterocycle containing one or two nitrogen atoms, wherein Z$_1$ is —CHR$_6$—; wherein Me is methyl, and wherein all other variables are as defined before:

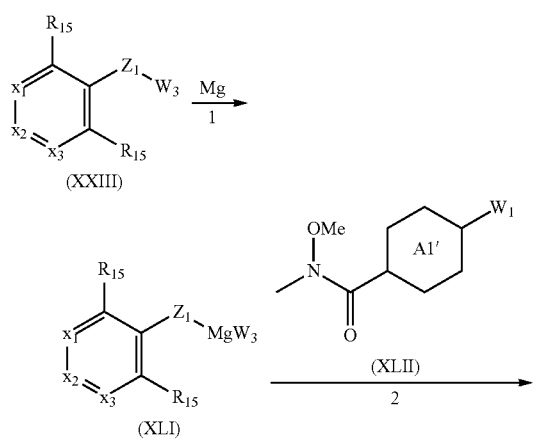

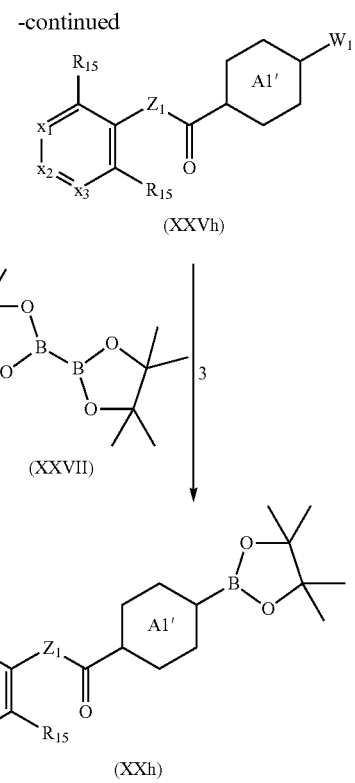

1: an intermediate of formula (XXIII) can be converted into an intermediate of formula (XLI) by reaction with magnesium and a suitable solvent, such as for example THF or diethyl ether (Et$_2$O). This type of reaction can also be performed in the presence of a suitable reagent, such as for example 1,2-dibromoethane.
2: an intermediate of formula (XLI) can be reacted with an intermediate of formula (XLII) in the presence of a suitable solvent, such as for example methyltetrahydrofuran (Methyl-THF) or THF, resulting in an intermediate of formula (XXVh)
3: an intermediate of formula (XXVh) can be reacted with an intermediate of formula (XXVII) in the presence of a suitable base, such as for example Potassium acetate (AcOK), and a suitable solvent, such as for example dioxane resulting in an intermediate of formula (XXh).

6) Scheme 3:

Compounds of formula (Ii-Im) wherein ring A1 is limited to A1' (no bicycles formed), can be prepared according to the following reaction scheme 3, wherein all variables are as defined before.

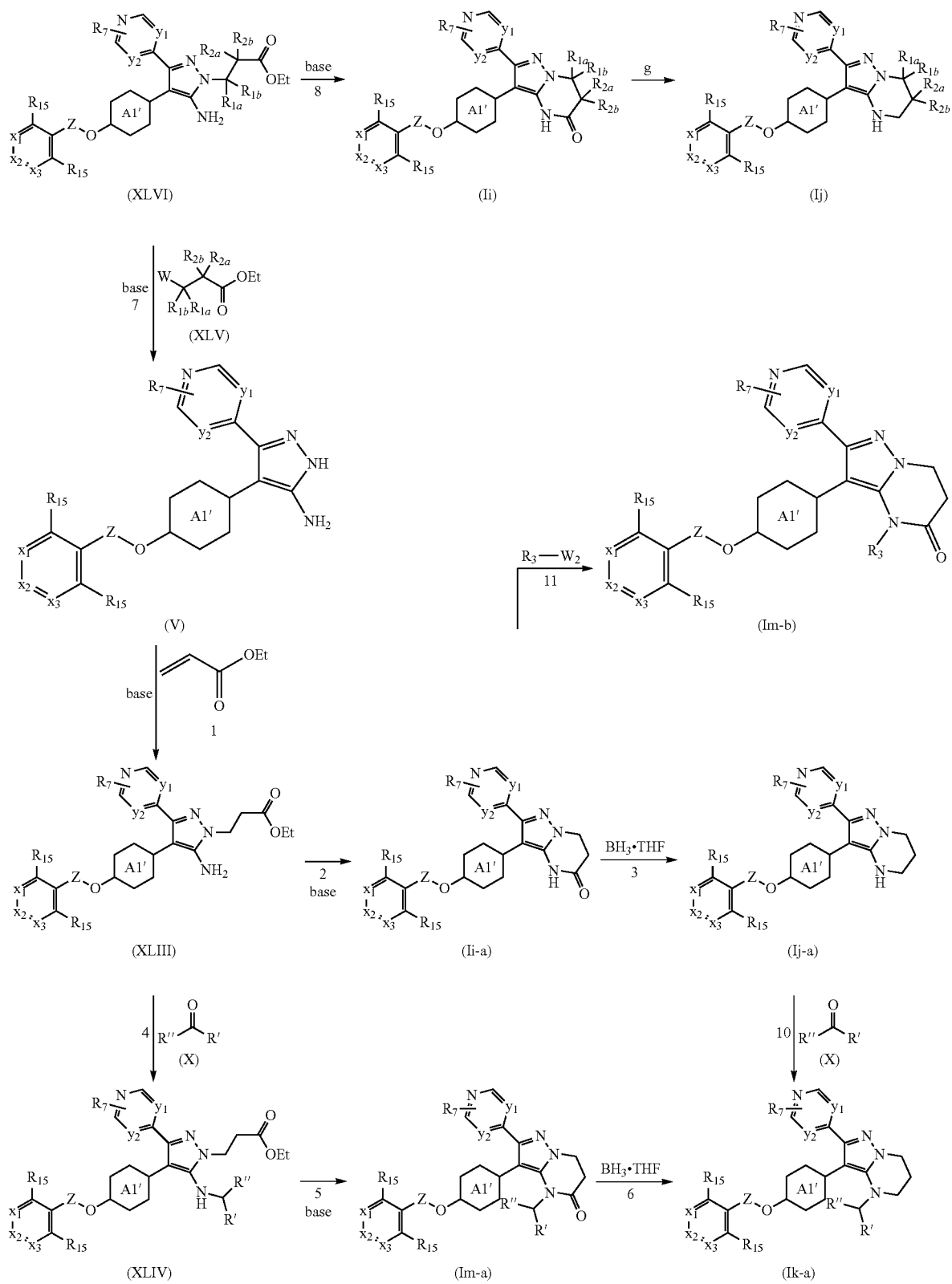

1: an intermediate of formula (V) can be reacted with ethyl acrylate in the presence of a suitable base, such as for example pyridine, resulting in an intermediate of formula (XLIII).

2: an intermediate of formula (XLIII) can be converted into a compound of formula (Ii-a) in the presence of a suitable base, such as for example $Cs_2CO_3$, and a suitable solvent, such as for example MeOH.

3: a compound of formula (Ii-a) can be converted into a compound of formula (Ij-a) by reaction with Borane tetrahydrofuran complex (BH₃.THF) in the presence of a suitable solvent, such as for example THF.
4: an intermediate of formula (XLIII) can be reacted with an intermediate of formula (X), in the presence of a suitable reducing agent, such as for example Sodium Triacetoxyborohydride (NaBH(OAc)₃), and a suitable solvent, such as for example DCE, resulting in an intermediate of formula (XLIV).
5: an intermediate of formula (XLIV) can be converted into a compound of formula (Im-a) in the presence of a suitable base, such as for example Cs₂CO₃, and a suitable solvent, such as for example MeOH.
6: a compound of formula (Im-a) can be converted into a compound of formula (Ik-a) by reaction with Borane tetrahydrofuran complex (BH₃.THF) in the presence of a suitable solvent, such as for example THF.
7: an intermediate of formula (V) can be reacted with an intermediate of formula (XLV), wherein W represents a suitable leaving group, such as for example iodide, bromide, chloride or tosylate, in the presence of a suitable base, such as for example NaH, and a suitable solvent, such as for example DMF, resulting in an intermediate of formula (XLVI).
8: an intermediate of formula (XLVI) can be converted into a compound of formula (Ii) in the presence of a suitable base, such as for example Cs₂CO₃, and a suitable solvent, such as for example MeOH.
9: a compound of formula (Ii) can be converted into a compound of formula (Ij) by reaction with Borane tetrahydrofuran complex (BH₃.THF) in the presence of a suitable solvent, such as for example THF.
10: a compound of formula (Ij-a) can be reacted with an intermediate of formula (X), in the presence of a suitable reducing agent, such as for example sodium triacetoxyborohydride (NaBH(OAc)₃), and a suitable solvent, such as for example DCE, resulting in a compound of formula (Ik-a).
11: a compound of formula (Ii-a) can be reacted with an intermediate R₃—W₂, wherein W₂ represents a suitable leaving group, such as for example chloride, bromide or iodide, in the presence of a suitable base, such as for example Ag₂OH₂, and a suitable solvent, such as for example DMF, resulting in a compound of formula (Im-b).

7) Scheme 3a:

Compounds of formula (Ij-b), (Ik-b) and (I'a)) wherein ring A1 is limited to A1' and wherein all variables are as defined before, can be prepared according to the following reaction scheme 3a.

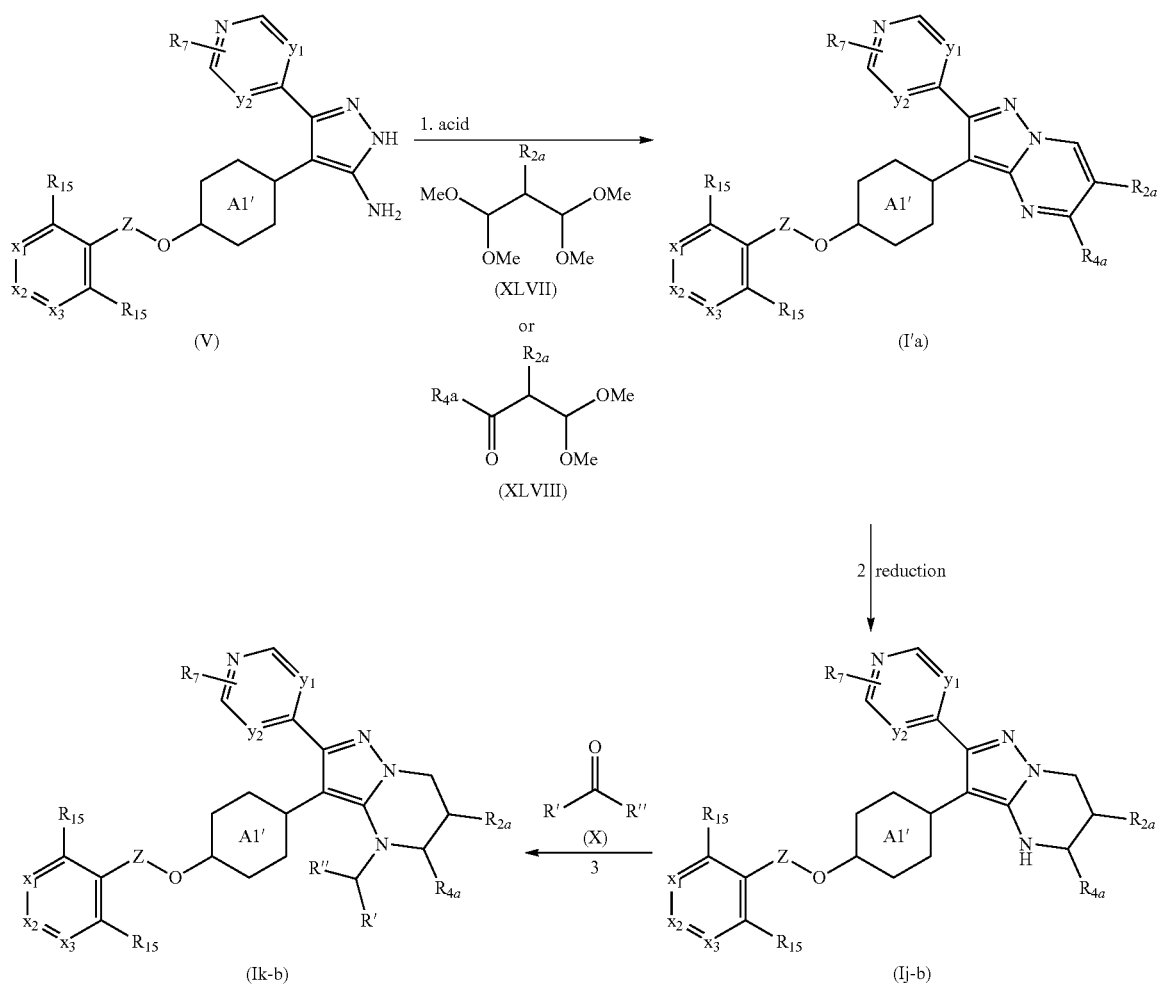

1: an intermediate of formula (V) can be reacted with an intermediate of formula (XLVII) (Me is methyl) in the presence of a suitable acid, such as for example AcOH, resulting in a compound of formula (I'a) wherein $R_{4a}$ is an hydrogen.
An intermediate of formula (V) can also be reacted with an intermediate of formula (XLVIII) in the presence of a suitable acid, such as for example AcOH, and a suitable solvent, such as for example EtOH, resulting in a compound of formula (I'a).
2: a compound of formula (I'a) can be converted into a compound of formula (Ij-b) by reaction with a suitable reducing agent, such as for example NaBH$_4$, in the presence of a suitable solvent, such as for example EtOH.
3: a compound of formula (Ij-b) can be reacted with an intermediate of formula (X), in the presence of a suitable reducing agent, such as for example Sodium Triacetoxyborohydride (NaBH(OAc)$_3$), and a suitable solvent, such as for example DCE or DCM, resulting in a compound of formula (Ik-b).

8) Scheme 3b: Synthesis of Compounds (I'):
Compounds of formula (I'a-x) can be prepared according to the following reaction scheme 3b.
In scheme 3b the following definitions apply:
$Y_x$ is defined as O, and ring A1 is phenyl or a 6-membered aromatic heterocycle containing one or two nitrogen atoms; wherein the phenyl or the heterocycle is optionally substituted with one or two $R_8$ substituents;
or a $R_8$ substituent of ring A1 on an atom adjacent to the atom carrying the $Y_x$—Z substituent is taken together with the $R_6$ substituent of Z to form a bicyclic ring; and all other variables in Scheme 3b are as defined before.

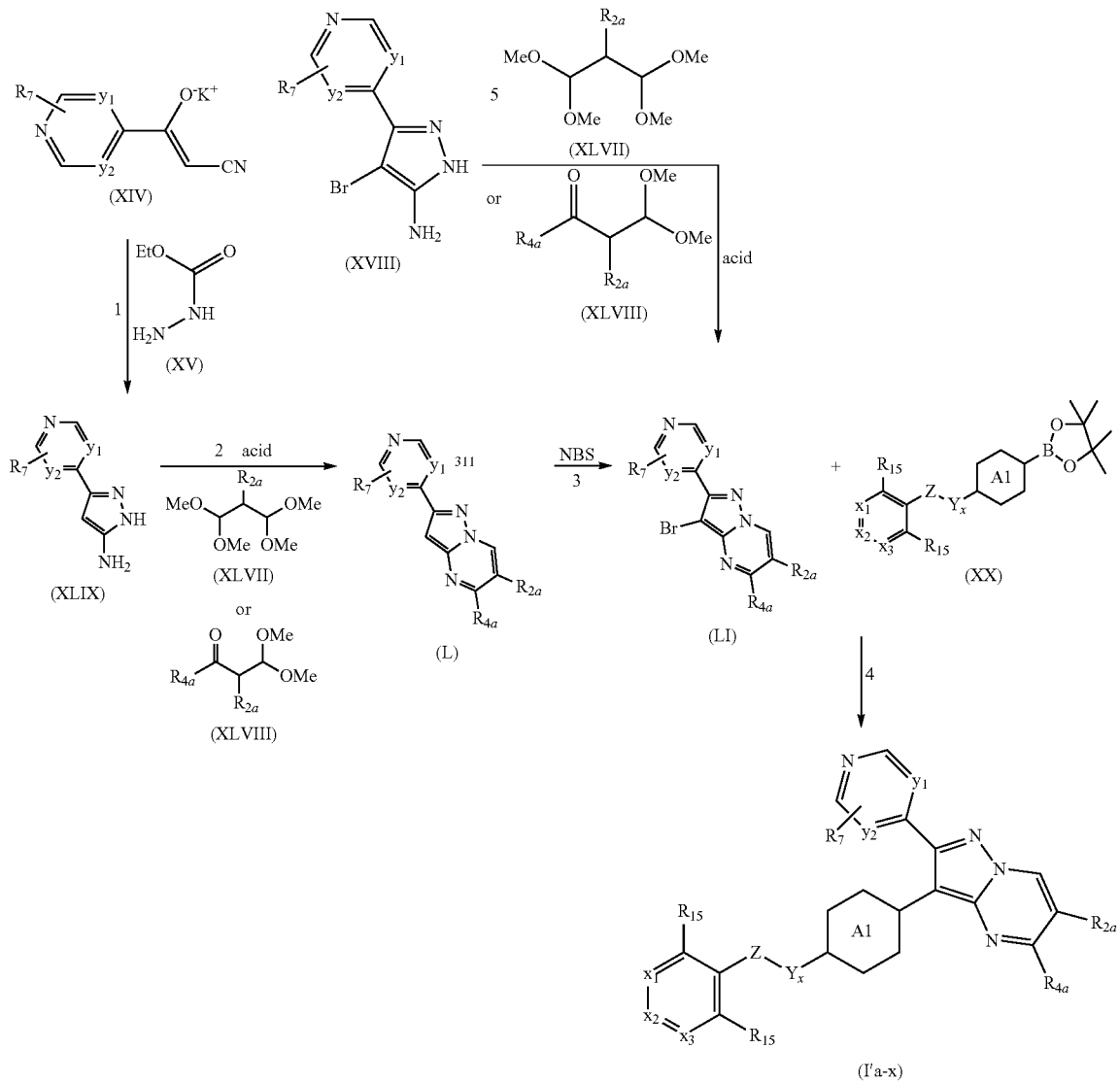

1: an intermediate of formula (XIV) can be reacted with an intermediate of formula (XV) in the presence of a suitable acid, such as for example HCl, and a suitable solvent, such as for example EtOH. The resulting intermediate can then reacted with a suitable base, such as for example K$_2$CO$_3$, resulting in an intermediate of formula (XLIX).
2: an intermediate of formula (XLIX) can be reacted with an intermediate of formula (XLVII) in the presence of a suitable acid, such as for example AcOH, resulting in an intermediate of formula (L) wherein R_4a is an hydrogen.

An intermediate of formula (XLIX) can also reacted with an intermediate of formula (XLVIII) in the presence of a suitable acid, such as for example AcOH, and a suitable solvent, such as for example EtOH, resulting in an intermediate of formula (L).

3: an intermediate of formula (L) can be converted into an intermediate of formula (LI) by reaction with NBS in the presence of a suitable solvent, such as for example $CH_3CN$.

4: an intermediate of formula (LI) can be reacted with an intermediate of formula (XX) in the presence of a suitable catalyst, such as for example [1,1'-bis(diphenylphosphino-kP)ferrocene]dichloropalladium ($PdCl_2dppf$), a suitable base, such as for example potassium phosphate ($K_3PO_4$), and a suitable solvent or solvent mixture, such as for example dioxane and water, resulting in a compound of formula (I'a-x).

5: an intermediate of formula (XVIII) can be reacted with an intermediate of formula (XLVII) in the presence of a suitable acid, such as for example AcOH, resulting in an intermediate of formula (LI) wherein R_4a is an hydrogen.

An intermediate of formula (XVIII) can also reacted with an intermediate of formula (XLVIII) in the presence of a suitable acid, such as for example AcOH, and a suitable solvent, such as for example EtOH, resulting in an intermediate of formula (LI).

9) Scheme 3c: Synthesis of Compounds (I'):

Compounds of formula (I'b-a), (I'a-a) and (I'a-a1), wherein $R_{4a'}$ is $C_{1-6}$alkyl-O-carbonyl-, and ring A1' and the other variables are as defined before, can also be prepared according to the following reaction scheme 3c.

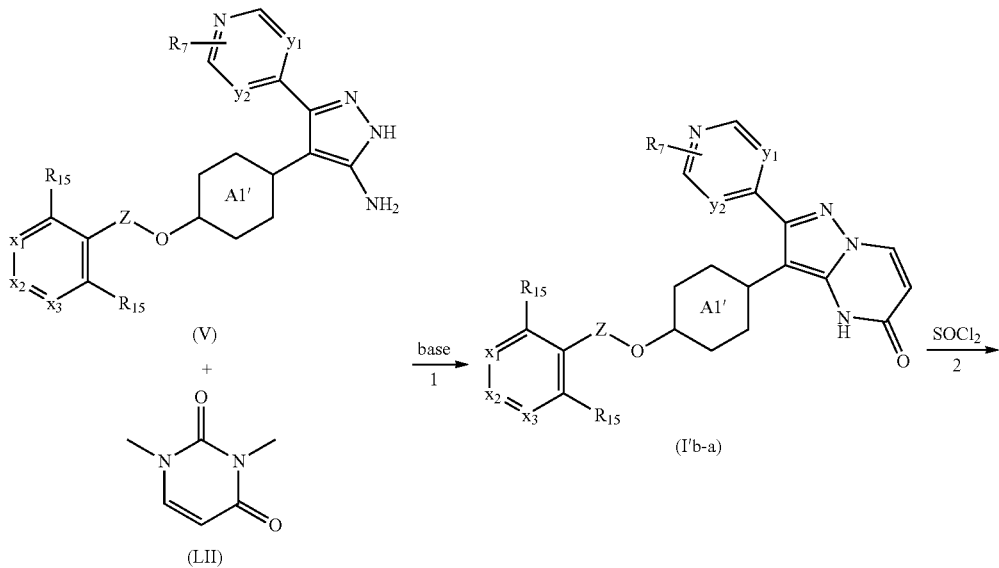

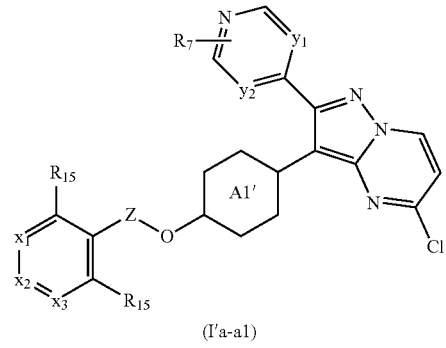

(I'a-a1)

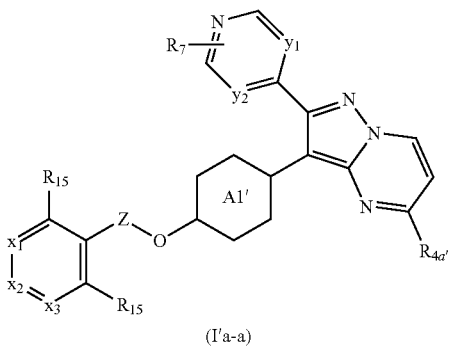

(I'a-a)

1: an intermediate of formula (V) can be reacted with an intermediate of formula (LII) in the presence of a suitable base, such as for example sodium ethoxide (NaOEt), and a suitable solvent, such as for example 2-methyl-2-butanol, resulting in a compound of formula (I'b-a).

2: a compound of formula (I'b-a) can be converted into a compound of formula (I'a-a1) by reaction with Thionyl chloride in the presence of a suitable catalyst, such as for example DMF, and a suitable solvent, such as for example DCE.

3: a compound of formula (I'a-a1), wherein $R_{4a}$ is a chloride, can be converted into a compound of formula (I'a-a) by reaction with carbon monoxide in the presence a suitable catalyst, such as for example Pd(OAc)$_2$, a suitable ligand, such as for example 1,2-bis(diphenylphosphino)ethane, a suitable base, such as for example Et$_3$N, and a suitable solvent, such as for example MeOH, resulting in a compound of formula (I'a-a) wherein is $C_{1-6}$alkyl-O-carbonyl- (e.g. COOMe).

10) Scheme 4:

Compounds of formula (I'a-a2) and (I'a-a3), and compounds of formula (Ij-c), wherein all variables are as defined before, can also be prepared according to the following reaction scheme 4. Ring A1 is as defined before.

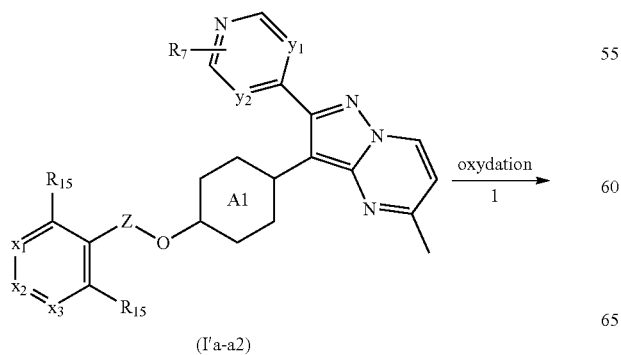

(I'a-a2)

(I'a-a3)

(Ij-c)

1: a compound of formula (I'a-a2), wherein $R_4a$ is a methyl, can be oxidized by reaction with a suitable oxidizing agent, such as for example SeO$_2$, in the presence of a suitable solvent, such as for example dioxane. The resulting intermediate can be converted into a compound of formula (I'a-a3) by reaction with a suitable acid, such as for example H$_2$SO$_4$, in the presence of a suitable solvent, such as for example MeOH.

2: a compound of formula (I'a-a3) can be reduced into a compound of formula (Ij-c) in the presence of a suitable reducing agent, such as for example NaBH$_4$, a suitable solvent or solvent mixture, such as for example THF and methanol (MeOH) optionally in the presence of CaCl$_2$.

11) Scheme 5:

Compounds of formula (I'b-b1), (I'b-b2), and compounds of formula (In-a), (In-b) and (In-c) can be prepared according to the following reaction scheme 5 wherein all variables are as defined before.

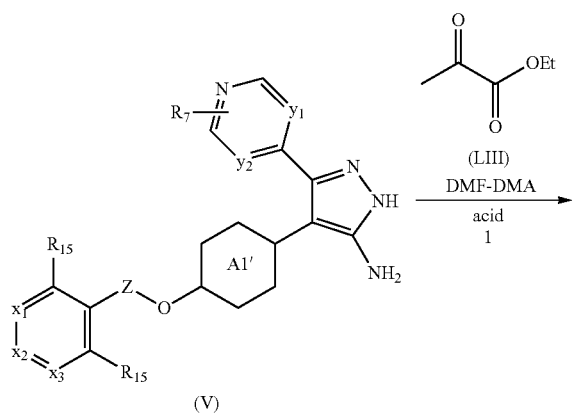
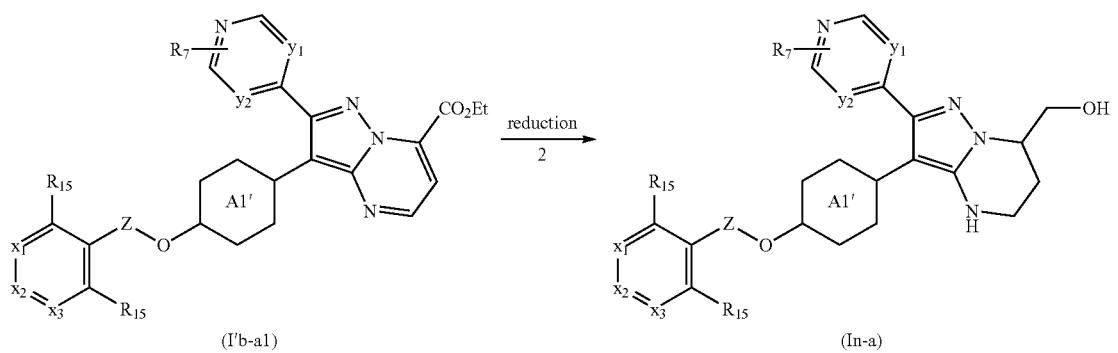
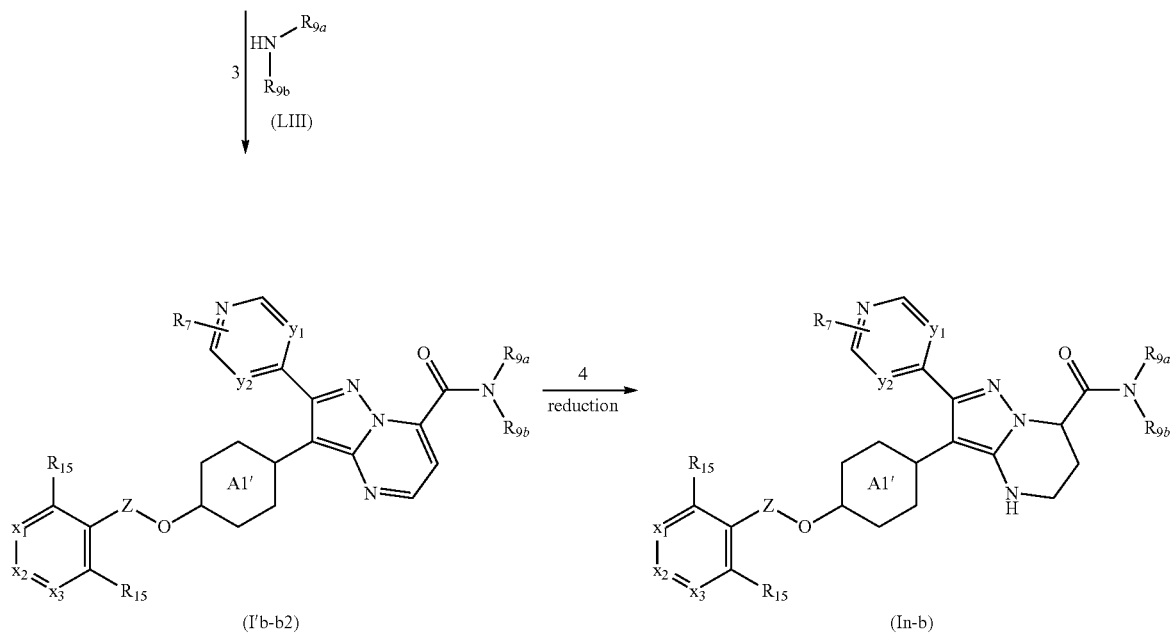

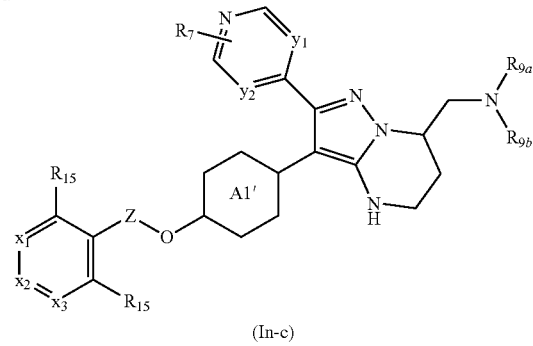

(In-c)

1: an intermediate of formula (V) can be converted into a compound of formula (I'b-b1) by reaction with ethyl pyruvate and N,N-dimethylformamide dimethyl acetate (DMF-DMA), in the presence of a suitable solvent, such as for example AcOH.
2: a compound of formula (I' b-b1) can be converted into a compound of formula (In-a) by reaction with a suitable reducing agent, such as for example NaBH$_4$, and a suitable solvent, such as for example EtOH.
3: a compound of formula (I' b-b1) can be reacted with an intermediate of formula (LIII) in the presence of a suitable solvent, such as for example THF, resulting in a compound of formula (I'b-b2).
4: a compound of formula (I'b-b2) can be converted into a compound of formula (In-b) in the presence of a suitable reducing agent, such as for example NaBH$_4$, and a suitable solvent, such as for example EtOH.
5: a compound of formula (In-b) can be converted into a compound of formula (In-c) by reaction with Borane tetrahydrofuran complex (BH$_3$.THF) in the presence of a suitable solvent, such as for example THF.

12) Scheme 6: Synthesis of Final Compounds when Ring A is Partially Saturated, X is a Covalent Bond and Y=(C=O):

Compounds of formula (Io), can be prepared according to the following reaction scheme 6, wherein all variables are as defined before (tBu is tert-butyl).

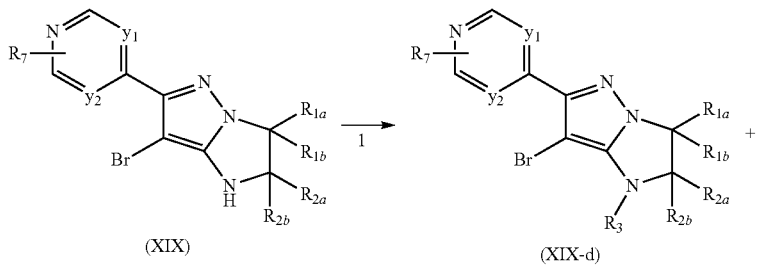

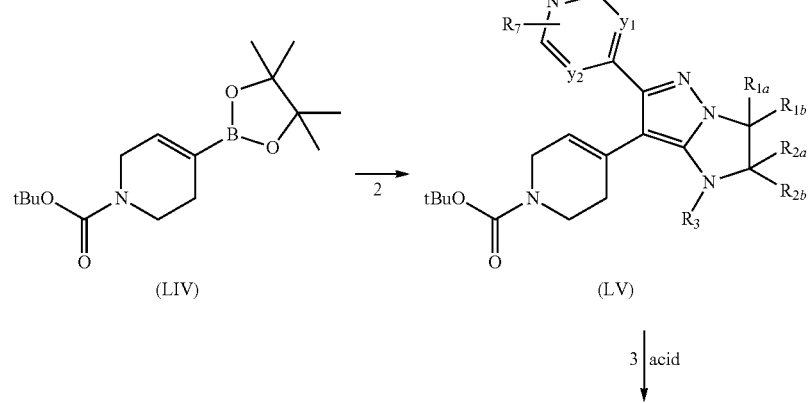

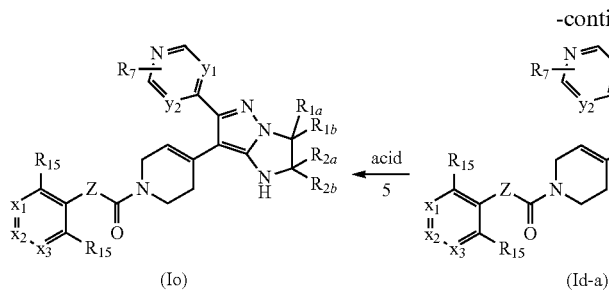

(Io)

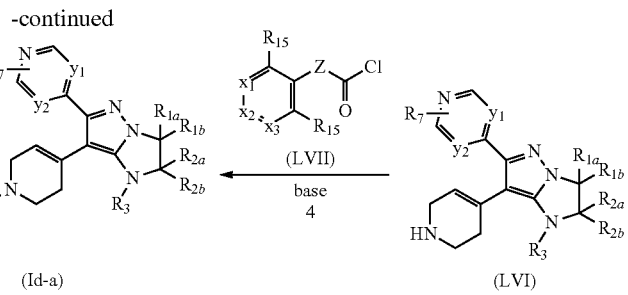

(Id-a)          (LVI)

1: an intermediate of formula (XIX) can be protected by a suitable protected group R3, such as for example a SEM group, by reaction with 2-(trimethylsilyl) ethoxymethyl (SEM) chloride, in the presence of a suitable base, such as for example NaH, and a suitable solvent, such as for example THF or DMF, resulting in an intermediate of formula (XIX-d).

2: an intermediate of formula (XIX-d) can be reacted with an intermediate of formula (LIV) in the presence of suitable catalyst, such as for example Palladium acetate or (PdCl$_2$dppf), a suitable base, such as Na$_2$CO$_3$, and a suitable solvent, such as for example dioxane, resulting in an intermediate of formula (LV).

3: an intermediate of formula (LV) can be deprotected to an intermediate of formula (LVI) by reaction with a suitable acid, such as for example HCl, and a suitable solvent, such as for example ACN.

4: an intermediate of formula(LVI) can be reacted with an intermediate of formula (LVII) in the presence of a suitable base, such as for example Et$_3$N, and a suitable solvent, such as for example DCM, resulting in a compound of formula (Id-a).

5: a compound of formula (Id-a) can be deprotected to a compound of formula (Io) with a suitable acid, such as for example tetrabutylammonium fluoride, and a suitable solvent, such as for example THF.

13) Scheme 7: Synthesis of Final Compounds when Ring A is Partially Saturated and Y=(C=O):

Compounds of formula (I'd) and (Ip), can be prepared according to the following reaction scheme 7.

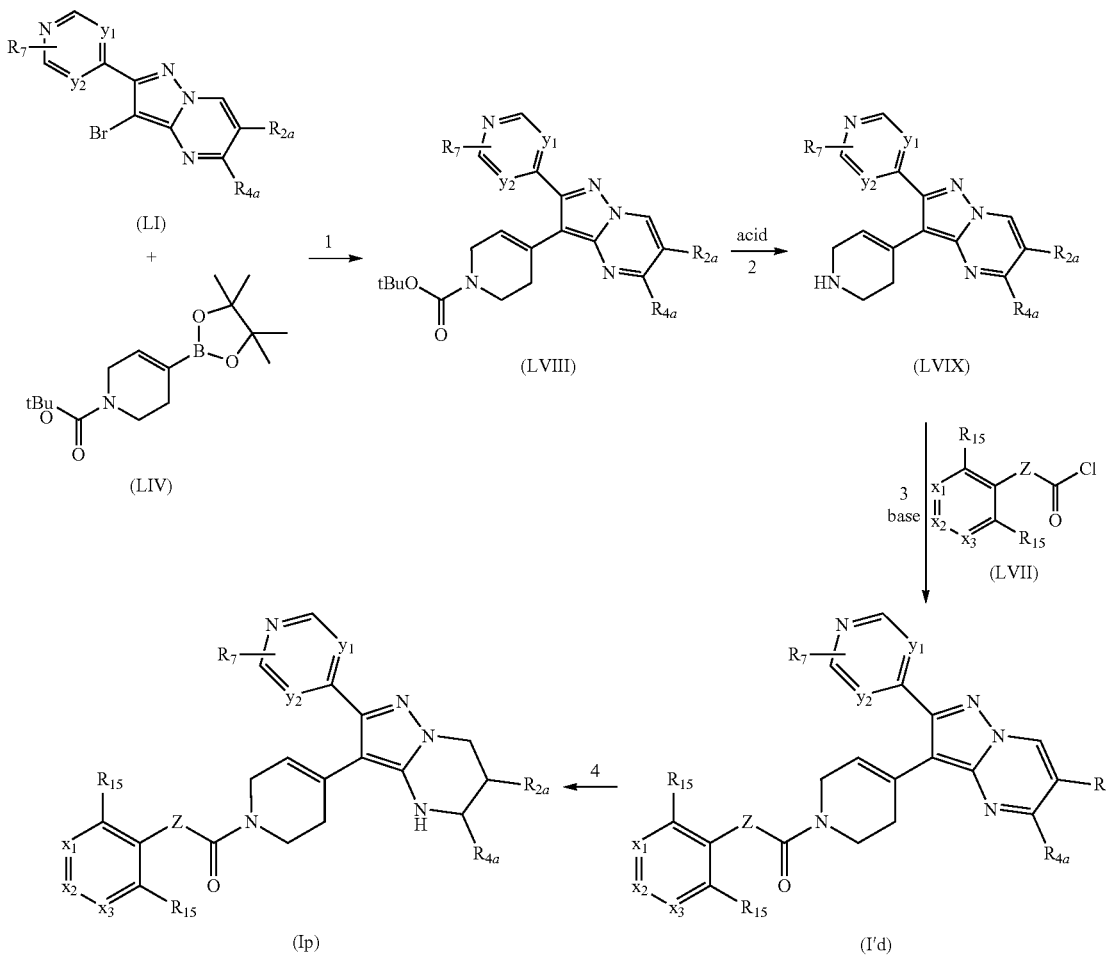

1: an intermediate of formula (LI) can be reacted with an intermediate of formula (LIV) in the presence of suitable catalyst, such as for example Palladium acetate or (PdCl₂dppf), a suitable base, such as Na₂CO₃, and a suitable solvent, such as for example dioxane, resulting in an intermediate of formula (LVIII).
2: an intermediate of formula (LVIII) can be deprotected to an intermediate of formula (LVIX) by reaction with a suitable acid, such as for example HCl, and a suitable solvent, such as for example ACN.
3: an intermediate of formula(LVIX) can be reacted with an intermediate of formula (LVII) in the presence of a suitable base, such as for example Et₃N, and a suitable solvent, such as for example DCM, resulting in a compound of formula (I'd).
4: a compound of formula (I'd) can be converted into a compound of formula (Ip) in the presence of a suitable reducing agent, such as for example NaBH₄, and a suitable solvent, such as for example EtOH.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically by Supercritical fluid chromatography using polysaccharide-based chiral stationary.

The chirally pure forms of the compounds of Formula (I) form a preferred group of compounds. It is therefore that the chirally pure forms of the intermediates and their salt forms are particularly useful in the preparation of chirally pure compounds of Formula (I) and (I'). Also enantiomeric mixtures of the intermediates are useful in the preparation of compounds of Formula (I) and (I') with the corresponding configuration.

Pharmacology

It has been found that the compounds of the present invention inhibit ROS1 kinase activity. In particular, the compounds of the present invention are potent and selective Ros1 inhibitors.

As a consequence of their activity in inhibiting ROS kinases, the compounds and compositions thereof will be useful in providing a means of preventing the growth or inducing apoptosis of neoplasias. It is therefore anticipated that the compounds or compositions thereof will prove useful in treating or preventing, in particular treating, proliferative disorders such as cancers. In addition, the compounds of the invention could be useful in the treatment of diseases in which there is a disorder of proliferation, apoptosis or differentiation.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

In particular examples of cancers which may be treated (or inhibited) include non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia.

In an embodiment, the compounds of the invention and compositions thereof may be useful for use in the treatment or prevention, in particular in the treatment, of non-small-cell lung cancer, cholangiocarcinoma, and glioblastoma multiforme.

In an embodiment, all or some of the compounds of the invention and compositions thereof may be useful for use in reducing tumors or prolonging survival in patients with a G2032R mutation in the Ros1 kinase domain.

In an embodiment, all or some the compounds of the invention and compositions thereof may be useful for use in reducing tumors or prolonging survival in patients with a L2026M mutation in the Ros1 kinase domain.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

Thus, in the pharmaceutical compositions, uses or methods of this invention for treating a disease or condition comprising abnormal cell growth, the disease or condition comprising abnormal cell growth in one embodiment is a cancer.

The compounds of the invention and compositions thereof may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

ROS is also known to play a role in apoptosis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease;

cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

The compounds of the present invention and compositions thereof may also have utility in male contraception.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I), (I'), and N-oxides, pharmaceutically acceptable addition salts, and solvates thereof, for use as a medicament.

The invention also relates to compounds of Formula (I), (I'), and N-oxides, pharmaceutically acceptable addition salts, and solvates thereof, for use in the inhibition of ROS, in particular ROS1, kinase activity.

The compounds of the present invention can be "anti-cancer agents", which term also encompasses "anti-tumor cell growth agents" and "anti-neoplastic agents".

The invention also relates to compounds of Formula (I), (I'), and N-oxides, pharmaceutically acceptable addition salts, and solvates thereof, for use in the treatment of diseases mentioned above.

The invention also relates to compounds of Formula (I), (I'), and N-oxides, pharmaceutically acceptable addition salts, and solvates thereof, for the treatment or prevention, in particular for the treatment, of said diseases.

The invention also relates to compounds of Formula (I), (I'), and N-oxides, pharmaceutically acceptable addition salts, and solvates thereof, for the treatment or prevention, in particular in the treatment, of ROS, in particular ROS1, mediated diseases or conditions.

The invention also relates to the use of compounds of Formula (I), (I'), and N-oxides, pharmaceutically acceptable addition salts, and solvates thereof, for the manufacture of a medicament.

The invention also relates to the use of compounds of Formula (I), (I'), and N-oxides, pharmaceutically acceptable addition salts, and solvates thereof, for the manufacture of a medicament for the inhibition of ROS, in particular ROS1.

The invention also relates to the use of compounds of Formula (I), (I'), and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I), (I'), and N-oxides, pharmaceutically acceptable addition salts, and solvates thereof, for the manufacture of a medicament for the treatment of any one of the disease conditions mentioned hereinbefore.

The compounds of Formula (I), (I'), and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I), (I'), and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), (I'), or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I) or (I'), a N-oxide, a pharmaceutically acceptable addition salt, or a solvate thereof, and one or more additional therapeutic agents, as well as administration of the compound of Formula (I) or (I'), a N-oxide, a pharmaceutically acceptable addition salt, or a solvate thereof, and each additional therapeutic agents in its own separate pharmaceutical dosage formulation. For example, a compound of Formula (I) or (I'), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I) or (I'), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I), (I'), and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing a compound of Formula (I) or (I'), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) or (I'), due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I), (I'), and N-oxides, pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I) or (I'), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoïds for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat;
- Recombinant interleukins for example aldesleukin, denileukin diftitox, interferon alfa 2a, interferon alfa 2b, peginterferon alfa 2b;
- MAPK inhibitors;
- Retinoids for example alitretinoin, bexarotene, tretinoin;
- Arsenic trioxide;
- Asparaginase;
- Steroids for example dromostanolone propionate, megestrol acetate, nandrolone (decanoate, phenpropionate), dexamethasone;
- Gonadotropin releasing hormone agonists or antagonists for example abarelix, goserelin acetate, histrelin acetate, leuprolide acetate;

Thalidomide, lenalidomide;
Mercaptopurine, mitotane, pamidronate, pegademase, pegaspargase, rasburicase;
BH3 mimetics for example ABT-737;
MEK inhibitors for example PD98059, AZD6244, CI-1040;
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;
a steroidal cytochrome P450 17alpha-hydroxylase-17,20-lyase inhibitor (CYP17), e.g. abiraterone, abiraterone acetate;
Glycolysis inhibitors, such as 2-deoxyglucose;
mTOR inhibitors such as rapamycins and rapalogs, and mTOR kinase inhibitors
PI3K inhibitors and dual mTOR/PI3K inhibitors;
autophagy inhibitors, such as chloroquine and hydroxychloroquine;
androgen receptor antagonist drugs, e.g. enzalutamide or ARN-509;
antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) or (I') and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day.

Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment. These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that the compound was obtained as a mixture of the R and the S enantiomers.

For a number of compounds, melting points (m.p.) were determined with a DSC 1 STAR$^e$ System from Mettler Toledo. Melting points were measured with a temperature gradient of 10° C./minute up to 350° C. Melting points are given by peak values.

EXAMPLES

Hereinafter, the term "NaH" means sodium hydride (60% in mineral oil); "DCM" means dichloromethane; "NaBH(OAc)₃" means sodium triacetoxyborohydride; "TBAF" means tetrabutylammonium fluoride; "Pd(tBu₃P)₂" means bis[tris(1,1-dimethylethyl)phosphine]-palladium; "P(tBu)₃.HBF₄" means tris(1,1-dimethylethyl)-phosphine, tetrafluoroborate(1-) (1:1); "Ac" means acetyl; "MeI" means iodomethane; "LAH" means lithium aluminium hydride; "NBS" means N-bromosuccinimide; "Int." Means Intermediate; "Co." means compound; "r.t." means room temperature; "r.m." means reaction mixture; "KOAc" means potassium acetate; "BisPin" means bis(pinacolato)diboron; "DCE" means 1,2-dichloroethane; "Boc" means tert-butoxy carbonyl; "ACN" means acetonitrile; "EDCI" means N'-(ethylcarbonimidoyl)-N,N-dimethyl-1,3-propanediamine monohydrochloride; "HOBT" means 1-hydroxy-1H-benzotriazole; "MeOH" means methanol; "LC" means liquid chromatography; "LCMS" means Liquid Chromatography/Mass spectrometry; "HPLC" means high-performance liquid chromatography; "TFA" means trifluoroacetic acid; "m.p." means melting point; "N₂" means nitrogen; "TBDMS" means tert-butyldimethylsilyl; "TBDMSO" or "OTBDMS" means tert-butyldimethylsilyloxy; "DBAD" means di-tert-butyl azodicarboxylate; "RP" means reversed phase; "min" means minute(s); "EtOAc" means ethyl acetate; "Et₃N" means triethylamine; "EtOH" means ethanol; "THF" means tetrahydrofuran; "Celite®" means diatomaceous earth; "DMF" means N,N-dimethyl formamide; "DMSO" means dimethyl sulfoxide; 'iPrOH" means 2-propanol; "iPrNH₂" means isopropylamine; "SFC" means Supercritical Fluid Chromatography; "DIPEA" means N,N-diisopropylethylamine; "Pd(PPh₃)₄" means tetrakis(triphenylphosphine)palladium; "w/v" means weight/volume; "PPh₃" means triphenylphosphine; "PdCl₂(PPh₃)₂" means bis(triphenylphosphine)palladium(II) dichloride; "supported PPh₃" means triphenylphosphine supported (polymer bound); "Et₂O" means diethyl ether; "Pd/C" means palladium on carbon; "Pt/C" means platinum on carbon; "Pd(OAc)₂" means palladium(II) acetate; "Et" means ethyl; "Me" means methyl; "h" means hours; and "PdCl₂(dppf)" means [1,1'-bis(diphenylphosphino-κP)ferrocene]dichloropalladium.

Hereinafter, "Int. 1 or 1" is '4-[[4-(1-methylethyl)phenyl]methoxy]-benzeneacetonitrile'; "Int. 2 or 2" is '4-pyridinecarbonitrile'; "Int. 5 or 5" is '(2-Bromoethyl)diphenylsulfonium trifluoromethane-sulfonate'.

Preparation of the Intermediates and the Final Compounds

Example A1: Preparation of Co. 1 a—Synthesis of Intermediate 3:

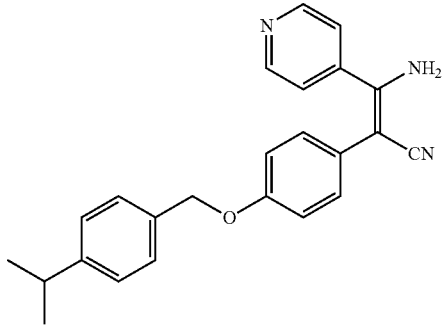 [SMILES: CC(C)c1ccc(COc2ccc(/C(C#N)=C(/N)c3ccncc3)cc2)cc1]

To a solution of 1 (=Int. 1=4-[[4-(1-methylethyl)phenyl]methoxy]-benzeneacetonitrile) (30.5 g, 115 mmol) and 2 (=Int. 2) (35.9 g, 345 mmol) in dry THF (400 mL) was added dropwise potassium 2-methyl-2-butoxide (64.5 mL, 115 mmol). The solution turned red immediately and was stirred for one hour. The mixture was quenched with water and concentrated in vacuo. The remaining aqueous layer was diluted with water and extracted with DCM (3 times). The combined organic layers were dried over MgSO₄ and evaporated in vacuo to give a yellow solid. The residue was triturated in Et₂O and filtered off on a glass frit to give 25.8 g of the intermediate 3 as a pale yellow solid (61%).

b—Synthesis of Intermediate 4:

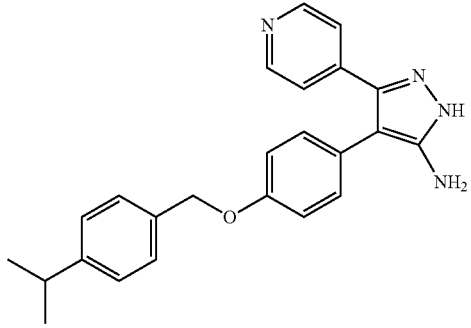 [SMILES: CC(C)c1ccc(COc2ccc(-c3c(-c4ccncc4)n[nH]c3N)cc2)cc1]

To a mixture of 3 (10 g, 27 mmol) in ethanol (47 mL) and acetic acid (47 mL) was added hydrazine monohydrate (16.5 ml, 270 mmol). The mixture was refluxed overnight and cooled down to r.t. Water and DCM were added, then K₂CO₃ solid. The mixture was extracted with DCM, the organic layer was separated, dried over MgSO₄, filtered and evaporated until dryness. The residue was taken up in Et₂O. The precipitate was filtered off and dried in vacuo to give 7.2 g of the intermediate 4. The filtrate was evaporated to give 3 g which was purified by preparative LC (Stationary phase: irregular SiOH 15-40 μm 300 g MERCK, Mobile phase: 95% NH₄OH, 5% DCM, 0.5% MeOH). The pure fractions were collected and the solvent evaporated until dryness to give 1 g of the intermediate 4. Global yield: 8.2 g of the intermediate 4 (79%).

c—Synthesis of Compound 1:

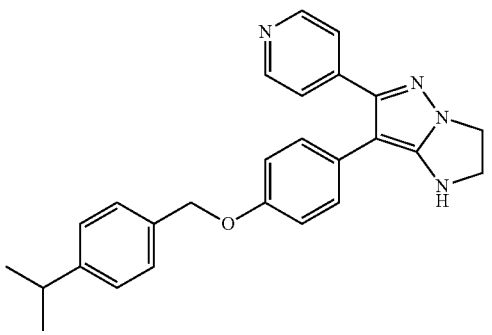 [SMILES: CC(C)c1ccc(COc2ccc(-c3c(-c4ccncc4)nn4c3NCC4)cc2)cc1]

To a solution of 4 (6.3 g, 16.4 mmol) in DMF (106 mL) was added diisopropylethylamine (6.9 mL, 40. mmol) and 5 (8.9 g, 20.1 mmol) at r.t. The solution was heated at 90° C. for 1 h 30, then cooled down to r.t. The crude mixture was diluted with EtOAc and washed twice with a saturated aqueous solution of NaCl. The organic layer was separated, dried over MgSO$_4$, filtered off and evaporated in vacuo. The residue was purified by preparative LC (Stationary phase: Irregular SiOH 20-45 μm 120 g, GRACE, Mobile phase gradient: from 97% DCM, 3% MeOH, 0.1% NH$_4$OH to 95% DCM, 5% MeOH, 0.1% NH$_4$OH). The pure fractions were collected and solvent evaporated until dryness. The residue was crystallized from ACN and the precipitate was filtered off and dried in vacuo to give 2.6 g of Compound 1 (39%).

Example A2: Preparation of Co. 2 a—Synthesis of Intermediate 6:

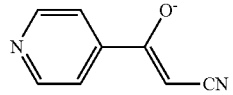 [SMILES: N#C/C=C(\[O-])c1ccncc1]

To a solution of ACN (6 mL, 115 mmol) and ethyl isonicotinate (51.6 mL, 345 mmol) in dry THF (500 mL) was slowly added potassium 2-methyl-2-butoxide (48.3 mL, 345 mmol). The reaction was stirred at r.t. for 18 h, quenched with water and evaporated in vacuo. The solid was triturated with Et$_2$O, filtered on a glass frit and washed with Et$_2$O (3 times) to give 17.3 g of intermediate 6, yellow solid (quantitative yield).

b—Synthesis of Intermediate 7:

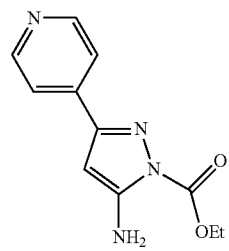 [SMILES: CCOC(=O)n1nc(-c2ccncc2)cc1N]

To a suspension of 6 (11.9 g, 81.9 mmol) in EtOH (140 mL) were added ethyl carbazate (10.2 g, 98.2 mmol) and HCl 37% (7.54 mL, 90.3 mmol). The mixture was stirred at r.t. for 2 h and at 50° C. for 1 h. The mixture was cooled down to r.t. and the precipitate was filtered off. The filtrate was evaporated to dryness and taken-up in DCM. The organic layer was washed with a saturated solution of NaHCO$_3$ and dried over MgSO$_4$ and evaporated in vacuo to give 11.98 g of intermediate 7, pale beige solid (63%). The crude product was used in the next step without purification.

c—Synthesis of Intermediate 8:

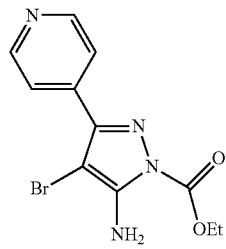 [SMILES: CCOC(=O)n1nc(-c2ccncc2)c(Br)c1N]

To a solution of 7 (2.90 g, 12.5 mmol) in DCM (110 mL) at 0° C. was added NBS (2.44 g, 13.7 mmol) portion wise. The mixture was stirred at r.t. for 1 h then water was added. The organic layer was separated, dried over MgSO$_4$, filtered off and evaporated in vacuo to give brown oil which was triturated in Et$_2$O. The solid was filtered on a glass frit, washed with Et$_2$O and dried in vacuo to give 3.72 g of intermediate 8, clear brown solid (96%).

d—Synthesis of Intermediate 9:

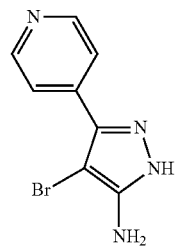 [SMILES: Nc1[nH]nc(-c2ccncc2)c1Br]

8 (2.4 g, 7.7 mmol) and Et$_3$N (10.7 mL, 77.1 mmol) in MeOH (50 mL) were stirred at r.t. overnight. The mixture was evaporated in vacuo to afford sticky dark brown oil. The crude mixture was taken-up in a mixture of DCM/MeOH (95:5) and was washed with a saturated solution of K$_2$CO$_3$. The organic layer was dried over MgSO$_4$, filtered off and evaporated in vacuo to give 1.5 g. The residue was purified by preparative LC (Stationary phase: Irregular SiOH 20-45 μm 40 g GRACE, Mobile phase: 40% Heptane, 10% MeOH, 50% EtOAc). The pure fractions were collected and the solvent was evaporated till dryness to give 0.65 g of intermediate 9 (35%).

e—Synthesis of Intermediate 10:

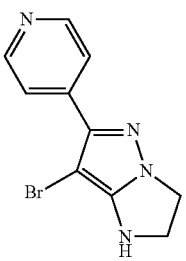 [SMILES: Brc1c(-c2ccncc2)nn2c1NCC2]

To a solution of 9 (0.65 g, 2.7 nmol) in DMF (10 mL) was added DIPEA (1.2 mL, 6.8 mmol) and 5 (0.96 g, 3.3 mmol). The solution was heated at 90° C. for 3 h then cooled down to r.t. EtOAc and a 10% aqueous solution of NH₄Cl were added. The organic layer was separated, washed with water and a saturated aqueous solution of NaCl, dried over MgSO₄, filtered and evaporated. The residue was purified by preparative LC (Irregular SiOH 15-40 µm, 40 g Grace, mobile phase: 95/5 DCM/MeOH). The pure fractions were collected and solvent evaporated until dryness to give 280 mg of intermediate 10, beige solid (39%).

f—Synthesis of Intermediate 11:

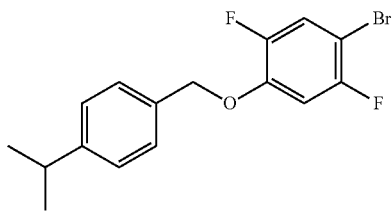 [SMILES: CC(C)c1ccc(COc2cc(F)c(Br)cc2F)cc1]

Under N₂, a solution of 4-bromo-2,5-difluorophenol (12 g, 58 mmol) in ACN (150 mL) was treated with K₂CO₃ (16 g, 117 mmol) and 4-isopropylbenzyl bromide (9.7 mL, 58 mmol) and the reaction mixture was stirred under reflux for 2 hours. The solution was filtered and concentrated to give 20 g of intermediate 11, colorless oil (100%). The product was used like this in the next reaction step.

g—Synthesis of Intermediate 12:

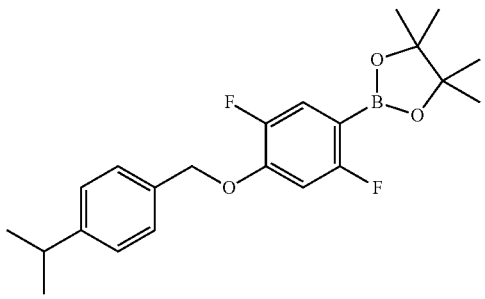 [SMILES: CC(C)c1ccc(COc2cc(F)c(B3OC(C)(C)C(C)(C)O3)cc2F)cc1]

In a Schlenk tube, a mixture of 11 (10.0 g, 29 mmol), KOAc (8.6 g, 88 mmol), BisPin (11 g, 44 mmol) in dry DME (150 mL) was carefully purged with N₂. PdCl₂(dppf)₂ (2.4 g, 2.9 mmol) was added and the reaction mixture was purged once again with N₂. The reaction mixture was stirred overnight at 100° C. The reaction mixture was diluted with EtOAc and washed with water (once) and with brine (twice). The organic phase was dried over MgSO₄ and evaporated in vacuo to give brown oil. The oil was purified by preparative LC (irregular SiOH 15-40 µm, 330 g, GraceResolv, Mobile phase: Heptane 90%, EtOAc 10%). The pure fractions were collected and solvent was evaporated until dryness to give 10.9 g of intermediate 12, yellow oil (96%).

h—Synthesis of Compound 2:

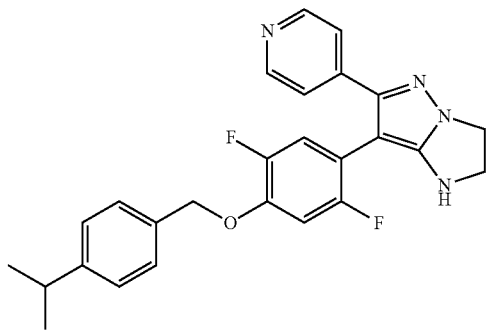 [SMILES: CC(C)c1ccc(COc2cc(F)c(-c3c(-c4ccncc4)nn4c3NCC4)cc2F)cc1]

A mixture of 10 (400 mg, 1.5 mmol), 12 (878 mg, 2.3 mmol) and K₃PO₄ (1.3 g, 6.0 mmol) in 1,4-dioxane (10 mL) and H₂O (3.5 mL) in a sealed tube was purged with N₂. Pd₂(dba)₃ (81 mg, 75 µmol) and P(tBu)₃.HBF₄ (44 mg, 0.15 mmol) were added, the mixture was purged again with N₂ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over MgSO₄, filtered off and evaporated. The residue was purified by preparative LC (Stationary phase: Interchim 40 g, Mobile phase: 96% DCM, 4% MeOH). The desired fractions were collected and solvent evaporated until dryness to give 550 mg of colorless oil which was triturated in Et₂O and the white solid formed was filtered and dried to give 358 mg, white solid (not pure enough). The solid was added to the filtrate and concentrated to give 570 mg, pale yellow oil which was purified by preparative LC (Stationary phase: Spherical bare silica 5 µm 150×30.0 mm, Mobile phase Gradient: from 70% Heptane, 2% MeOH (+10% NH₄OH), 28% EtOAC to 0% Heptane, 20% MeOH (+10% NH₄OH), 80% EtOAc). The pure fractions were collected and solvent evaporated until dryness to give 370 mg which was triturated in Et₂O. The white solid formed was filtered and dried to give 245 mg of Compound 2, white solid (36%). m.p.=153° C. (DSC).

Example A3: Preparation of Co. 3 a—Synthesis of Intermediate 13:

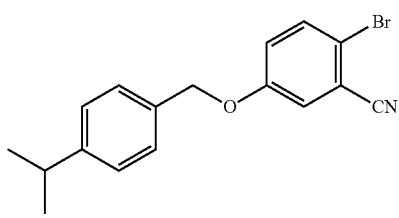 [SMILES: CC(C)c1ccc(COc2ccc(Br)c(C#N)c2)cc1]

A solution of 2-bromo-5-hydroxybenzonitrile (6.29 g, 31.8 mmol) in ACN (90 mL) and DMF (10 mL) was treated with K₂CO₃ (4.83 g, 34.9 mmol) and 4-isopropylbenzyl bromide (7.11 g, 33.4 mmol) at r.t. The reaction mixture was stirred for 18 hours at r.t. Then, water and EtOAc were added, and the organic layer was washed with brine, separated, dried over MgSO₄, filtered and concentrated in vacuo to afford 11.4 g of intermediate 13, white solid (quantitative).

b—Synthesis of Intermediate 14:

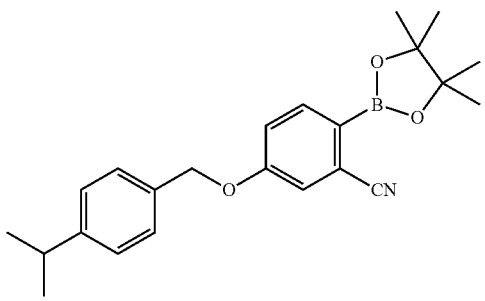 [SMILES: CC(C)c1ccc(COc2ccc(B3OC(C)(C)C(C)(C)O3)c(C#N)c2)cc1]

A mixture of 13 (4.72 g, 14.3 mmol), BisPin (5.45 g, 21.4 mmol) and KOAc (4.21 g, 42.9 mmol) in DME (90 mL) was carefully purged with $N_2$. $PdCl_2(dppf)_2$ (1.17 g, 1.43 mmol) was added and the reaction mixture was purged once again with $N_2$. The reaction mixture was stirred at 100° C. for 18 h. The reaction mixture was diluted with EtOAc and water. The organic layer was washed with brine and a saturated $NaHCO_3$ solution, dried over $MgSO_4$, filtered and evaporated in vacuo to give 9.09 g of black solid. The solid was purified by preparative LC (irregular SiOH 15-40 μm, 220 g, Grace, mobile phase gradient: EtOAc 0%, Heptane 100% to EtOAc 30%, Heptane 70%). The pure fractions were collected and solvent was evaporated until dryness to give 3.26 g of intermediate 14, white solid (60%).

c—Synthesis of Compound 3:

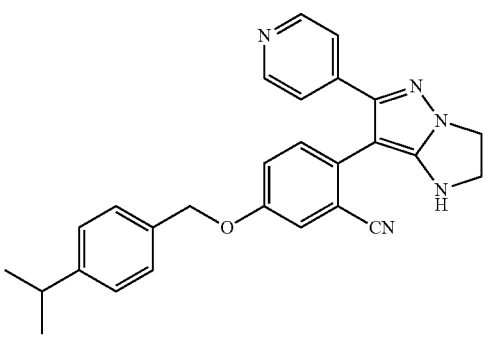 [SMILES: CC(C)c1ccc(COc2ccc(-c3c(-c4ccncc4)nn4c3NCC4)c(C#N)c2)cc1]

A mixture of 10 (15 0 mg, 566 μmol), 14 (320 mg, 849 μmol) and $K_3PO_4$ (430 mg, 2.26 mmol) in 1,4-dioxane (8.00 mL) and $H_2O$ (1.80 mL) in a sealed tube was purged with $N_2$. $Pd_2(dba)_3$ (30.2 mg, 28.3 μmol) and $P(tBu)_3 \cdot HBF_4$ (16.4 mg, 56.6 μmol) were added, the mixture was purged again with $N_2$ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over $MgSO_4$, filtered off and evaporated in vacuo to give 422 mg, black oil. The residue was purified by preparative LC (Stationary phase: Sunfire Silica 5 μm 150×30.0 mm, Mobile phase Gradient: from 0.2% $NH_4OH$, 98% DCM, 2% MeOH to 1% $NH_4OH$, 90% DCM, 10% MeOH). The pure fractions were collected and solvent evaporated until dryness to give 160 mg of white foam (65%). The product was crystallized from ACN. The precipitate was filtered on a glass frit and the solid was washed with $Et_2O$ (twice) and dried under high vacuum at 50° C. for 2 h to give 86 mg of Compound 3, white solid (35%). m.p.=191° C. (DSC).

Example A4: Preparation of Co. 4 a—Synthesis of Intermediate 15:

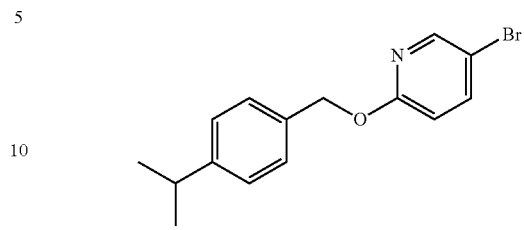

A solution of 4-isopropylbenzyl alcohol (3.1 g, 20 mmol) in dry DMF (50 mL) was treated at 0° C. with NaH 60% (818 mg, 20 mmol). After stirring for 1 hour at r.t., 5-bromo-2-fluoropyridine (3.0 g, 17 mmol) was added and the reaction mixture was stirred at r.t. for 3 days. The reaction mixture was quenched with water 200 mL and the white solid formed was filtrated. This solid was solubilized in EtOAc and dried on $MgSO_4$, filtrated and concentrated to give 5.9 g of intermediate 15, white solid (100%).

b—Synthesis of Intermediate 16:

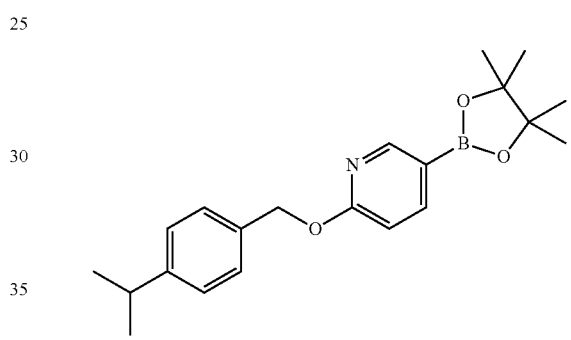

BisPin (5.2 g, 20 mmol) and KOAc (3.3 g, 34 mmol) were added to a solution of 15 (5.2 g, 17 mmol) in 1,4-dioxane (57 mL). The solution was purged with $N_2$ and charged with $PdCl_2(PPh_3)_2$ (0.60 g, 0.85 mmol). The resulting solution was purged again with $N_2$ and stirred at 80° C. for 17 hours. After dilution in EtOAc, the crude material was washed with water and brine. The organic layer was dried over $MgSO_4$ and evaporated to afford 12 g of brown oil. This oil was purified by preparative LC (irregular SiOH 15-40 μm, 120 g GraceResolv, mobile phase: heptane/EtOAc 80/20). The pure fractions were collected and solvent was evaporated to give 5.6 g of intermediate 16, brown solid (93%).

c—Synthesis of Compound 4:

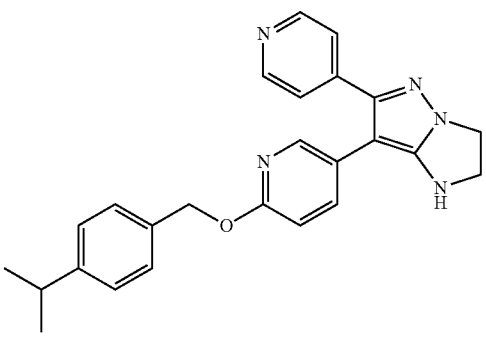 [SMILES: CC(C)c1ccc(COc2ccc(-c3c(-c4ccncc4)nn4c3NCC4)cn2)cc1]

A mixture of 10 (150 mg, 566 µmol), 16 (300 mg, 0.849 mmol) and K₃PO₄ (480 mg, 2.26 mmol) in 1,4-dioxane (8 mL) and H₂O (1.8 mL) in a sealed tube was purged with N₂. Pd₂(dba)₃ (30.2 mg; 28.3 µmol) and P(tBu)₃.HBF₄ (16.4 mg, 56.6 µmol) were added, the mixture was purged again with N₂ and heated at 120° C. using one single mode microwave (Biotage Initiator EXP 60) with a power output ranging from 0 to 400 W for 30 min [fixed hold time]. The mixture was put into DCM and washed with water. The organic layer was separated, dried over MgSO₄, filtered off and evaporated in vacuo to give 475 mg of black oil. The residue was purified by preparative LC (Stationary phase: Stability Silica 5 µm 150×30.0 mm, Mobile phase Gradient: from 0.5% NH₄OH, 95% DCM, 5% MeOH to 1.3% NH₄OH, 86% DCM, 13% MeOH). The pure fractions were collected and solvent evaporated until dryness to give 200 mg of colorless oil. This oil was triturated in Et₂O to give 167 mg of Compound 4, off-white foam (63%). m.p.=159° C. (DSC).

Example A5: Preparation of Co. 5 a—Synthesis of Intermediate 17:

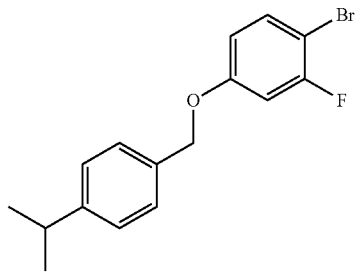 [SMILES: CC(C)c1ccc(COc2ccc(Br)c(F)c2)cc1]

Under N₂, a solution of 4-bromo-3-fluorophenol (11 g, 58 mmol) in ACN (150 mL) was treated with K₂CO₃ (16 g, 117 mmol) and 4-isopropylbenzyl bromide (9.7 mL, 58 mmol) and the reaction mixture was stirred under reflux for 2 h. The solution was filtrated and concentrated to give 18.9 g of intermediate 17, colorless oil (100%) which was used like this in the next reaction step.

b—Synthesis of Intermediate 18:

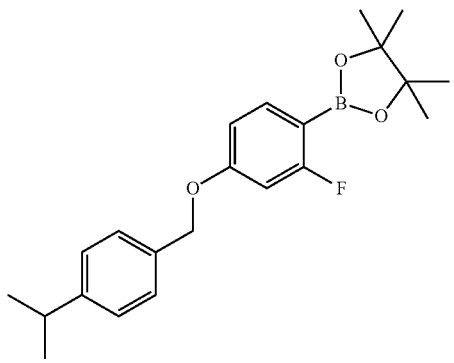 [SMILES: CC(C)c1ccc(COc2ccc(B3OC(C)(C)C(C)(C)O3)c(F)c2)cc1]

First Method:
In a sealed tube, a mixture of 17 (1.00 g, 3.09 mmol), KOAc (0.911 g, 9.28 mmol), BisPin (0.94 3 g, 3.71 mmol) in DME (9 mL) was carefully purged with N₂. PdCl₂(dppf)₂ (0.253 g, 0.309 mmol) was added and the reaction mixture was purged once again with N₂, then stirred for 17 h at 100° C. The reaction mixture was diluted with EtOAc and washed with water (once) and with brine (3 times). The organic phase was dried over MgSO₄, filtered and evaporated in vacuo to give 2.00 g of brown oil. The residue was purified by preparative LC (irregular SiOH 15-40 µm, 50 g, MERCK, Mobile phase gradient from 100% Heptane, 0% EtOAc to 80% Heptane, 20% EtOAc). The pure fractions were collected and solvent evaporated until dryness to give 903 mg of intermediate 18, colorless oil (79%).

Second Method:
To a solution of 4-hydroxy-2-fluorophenylboronic acid pinacol ester (1.10 g, 4.62 mmol) in ACN (45 mL) were added 4-isopropylbenzyl bromide (0.985 g, 4.62 mmol) and K₂CO₃ (1.28 g, 9.24 mmol). The reaction was heated at 80° C. for 2 h and cooled down to r.t. The mixture was filtered on a glass frit and evaporated in vacuo to give 1.78 g of intermediate 18, colorless oil which crystallized as a white solid (100%). Intermediate 18 was used without purification in the next reaction step.

c—Synthesis of Compound 5:

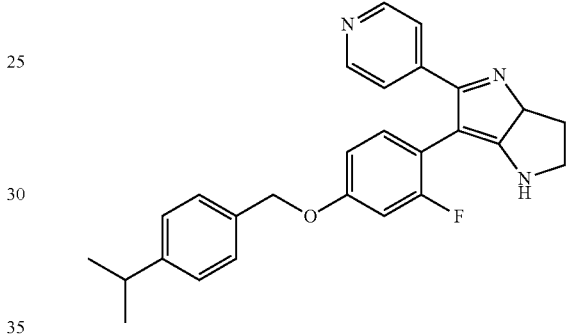

A mixture of 10 (280 mg, 1.05 mmol), 18 (586 mg, 1.6 mmol) and K₃PO₄ (896 mg, 4.2 mmol) in 1,4-dioxane (15 mL) and H₂O (5 mL) in a sealed tube was purged with N₂. Pd₂(dba)₃ (56 mg, 0.05 mmol) and P(tBu)₃.HBF₄ (30.6 mg, 0.1 mmol) were added, the mixture was purged again with N₂ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over MgSO₄, filtered off and evaporated in vacuo. The residue was purified by preparative LC (Stationary phase: GRACE 40 g, Mobile phase Gradient: from 0.2% NH₄OH, 98% DCM, 2% MeOH to 1% NH₄OH, 89% DCM, 10% MeOH). The desired fractions were collected and solvent evaporated until dryness to give 280 mg of residue. This residue was crystallized from Et₂O. The solid was filtered off and dried to give 140 mg of Compound 5 (31%). m.p.=141° C. (DSC).

Example A6: Preparation of Co. 6 a—Synthesis of Intermediate 19:

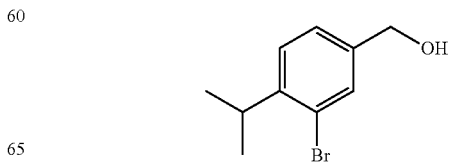

LAH (5.52 g, 145 mmol) was added to a stirred solution of methyl-3-bromo-4-isopropylbenzoate (34.0 g, 132 mmol) in THF (600 mL) at −20° C. The r.m. was stirred at −20° C. for 2 h. Then, the r.m. was quenched with 5.3 mL of water, 5.5 mL of NaOH 3N and 16 mL of water. The cake was filtered and washed with DCM. The filtrate was evaporated in vacuo to give 20.0 g of intermediate 19, yellow oil (66%).

b—Synthesis of Intermediate 20:

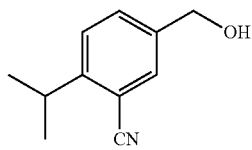

Pd(PPh$_3$)$_4$ (1.6 g, 1.4 mmol) was added to a mixture of 19 (3.2 g, 14 mmol) and zinc cyanide (1.7 g, 14 mmol) in DMF (10 mL) in a sealed tube. The mixture was heated at 120° C. for 60 min using one single mode microwave (Biotage) with a power output ranging from 0 to 400 W. The r.m. was cooled to r.t., poured into ice water and extracted with DCM. The organic layer was separated, dried over MgSO$_4$, filtered and the solvent was evaporated until dryness to give 2.6 g of residue. The residue was purified by preparative LC on (Irregular SiOH 15-40 μm 50 g Merck, mobile phase: 70/30 heptane/EtOAc). The pure fractions were collected and evaporated until dryness to give 1.4 g of intermediate 20 (57%).

c—Synthesis of Intermediate 21:

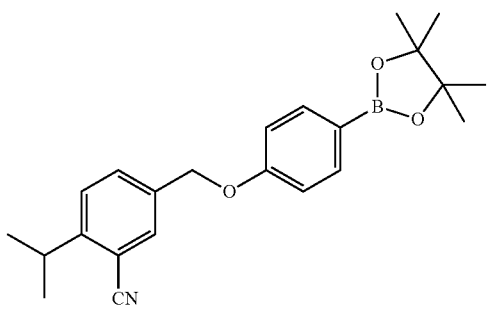 [SMILES: CC(C)c1ccc(COc2ccc(B3OC(C)(C)C(C)(C)O3)cc2)cc1C#N]

DBAD (1.3 g, 5.5 mmol) was added portionwise to a solution of 20 (0.8 g, 4.6 minol), 4-hydroxyphenylboronic acid pinacol ester (1.2 g, 5.5 mmol), supported PPh$_3$ (1.7 g, 5.5 mmol) in dry THF (30 mL). The mixture was stirred at r.t. overnight. The mixture was filtered and the filtrate was evaporated to give 3.7 g, yellow oil. The crude residue was purified by preparative LC (irregular SiOH 30 μm 80 g Interchim, mobile phase: heptane/EtOAc 90/10). The pure fractions were collected and solvent was evaporated until dryness to give 1.0 g of intermediate 21, colorless oil which quickly crystallized in a white solid (58%).

d—Synthesis of Compound 6:

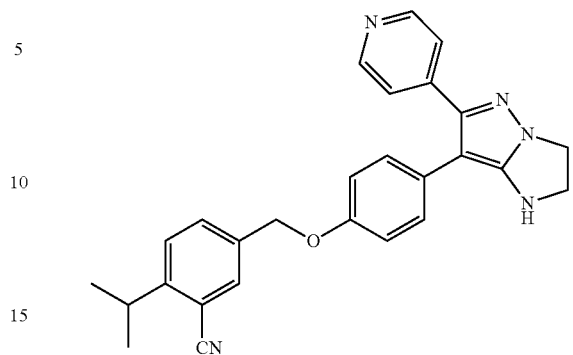

A mixture of 10 (150 mg, 566 μmol), 21 (320 mg, 849 μmol) and K$_3$PO$_4$ (430 mg, 2.26 mmol) in 1,4-dioxane (8.00 mL) and H$_2$O (1.80 mL) in a sealed tube was purged with N$_2$. Pd$_2$(dba)$_3$ (30.2 mg, 28.3 μmol) and P(tBu)$_3$.HBF$_4$ (16.4 mg, 56.6 μmol) were added, the mixture was purged again with N$_2$ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over MgSO$_4$, filtered off and evaporated in vacuo to give 517 mg of black oil. The residue was purified by preparative LC (Stationary phase: Sunfire Silica 5 μm 150×30.0 mm, Mobile phase Gradient: from 0.2% NH$_4$OH, 98% DCM, 2% MeOH to 1% NH$_4$OH, 89% DCM, 10% MeOH). The pure fractions were collected and solvent evaporated until dryness to give 177 mg of white foam which was triturated in Et$_2$O. The precipitate was filtered on a glass frit and the solid was dried under high vacuum at 50° C. for 2 h to give 139 mg of Compound 6, off-white solid (56%). m.p.=158° C. (DSC).

Example A7: Preparation of Co. 7 a—Synthesis of Intermediate 22:

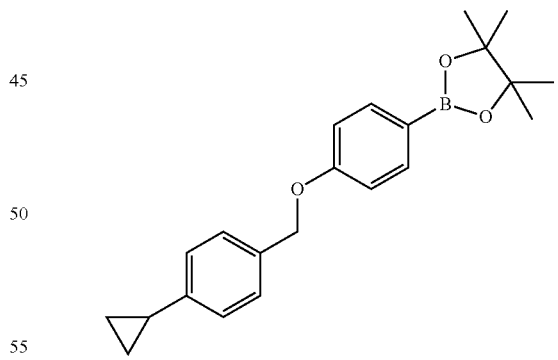

Under nitrogen, DBAD (15.5 g, 67 mmol) was added portion wise to a solution of (4-cyclopropylphenyl)methanol (10 g, 67 mmol), 4-hydroxyphenylboronic acid pinacol ester (14.8 g, 67 mmol), and PPh$_3$ (17.7 g, 67 mmol) in dry THF (500 mL). The mixture was stirred at r.t. overnight. THF was evaporated to give 64 g of a residue (yellow oil). The crude residue was purified by preparative LC (irregular SiOH 30 μm 220+330 g GraceResolv™, mobile phase: 90% Heptane, 10% EtOAc). The pure fractions were collected and solvent evaporated to give 19.7 g of intermediate 22, white solid (83%).

b—Synthesis of Compound 7:

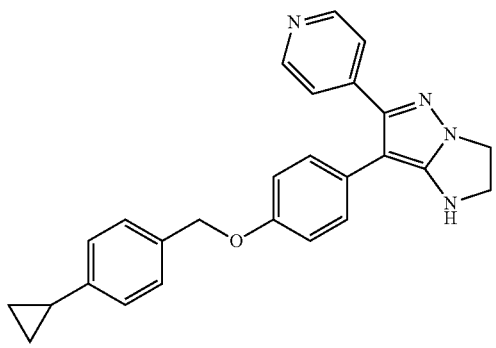 [SMILES: c1cc(-c2nn3c(c2-c2ccc(OCc4ccc(C5CC5)cc4)cc2)NCC3)ccn1]

A mixture of 10 (400 mg, 1.5 mmol), 22 (793 mg, 2.3 mmol) and K₃PO₄ (1.3 g, 6.0 mmol) in 1,4-dioxane (10 mL) and H₂O (3.5 mL) in a sealed tube was purged with N₂. Pd₂(dba)₃ (81 mg, 75 μmol) and P(tBu)₃.HBF₄ (44 mg, 0.15 mmol) were added, the mixture was purged again with N₂ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over MgSO₄, filtered off and evaporated in vacuo to give 1.37 g. The residue was purified by preparative LC (Stationary phase: graceResolv™ 40 g, Mobile phase: 96% DCM, 4% MeOH). The pure fractions were collected and solvent evaporated until dryness to give 260 mg of colorless oil which was triturated in Et₂O. The white solid formed was filtrated and dried to give 175 mg of Compound 7, white solid (28%). m.p.=159° C. (DSC).

Example A8: Preparation of Co. 8 a—Synthesis of Intermediate 23:

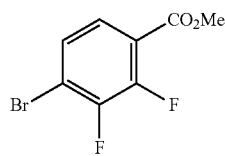 [SMILES: COC(=O)c1ccc(Br)c(F)c1F]

H₂SO₄ (1.1 mL, 21 mmol) was slowly added to a solution of 4-bromo-2,3-difluorobenzoic acid (2.5 g, 10.5 mmol) in MeOH (40 mL). The mixture was heated at 50° C. for 3 days. The mixture was concentrated in vacuo and the residue was partitioned between EtOAc and water and basified with K₂CO₃. The combined organic layers were washed with brine, dried over MgSO₄, filtered and concentrated in vacuo to give 2.6 g of intermediate 23, colorless oil which crystallized in a white solid (98%).

b—Synthesis of Intermediate 24:

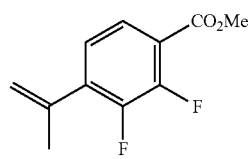

In a Schlenk tube, a mixture of 23 (2.5 g, 10 mmol), cesium fluoride (3.3 g, 22 mmol) and 2-isopropenyl-4,4,5,5-tetramethyl-1,3,2-dioxaborolane (2.0 mL, 11 mmol) in dry THF (60 mL) was purged with N₂. Pd(tBu₃P)₂ (254 mg, 0.50 mmol) was added and the mixture was purged again with N₂ and heated at 80° C. overnight. Water and EtOAc were added, the organic layer was separated, washed with brine, dried on MgSO₄, filtered over Celite® and evaporated. The residue was purified by preparative LC (Regular SiOH, 30 μm, 80 g GraceResolv™, mobile phase: Heptane/EtOAc 95/5). The pure fractions were collected and solvent evaporated until dryness to give 1.8 g of intermediate 24, yellow oil (85%).

c—Synthesis of Intermediate 25:

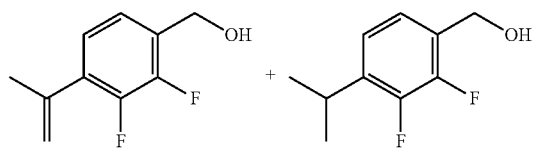

24 (1.8 g, 8.5 mmol) in dry THF (14 mL) was added dropwise to a suspension of LAH (0.39 g, 10 mmol) in dry THF (14 mL) at 0° C. under N₂. The mixture was stirred for 30 min. Water (1.4 mL) then DCM (75 mL) were added very slowly and stirred overnight. MgSO₄ was added and the insoluble was filtered on a pad of Celite® and evaporated until dryness to give 1.5 g of intermediate mixture 25, brown oil. The mixture was used like this in the next step.

d—Synthesis of Intermediate 26:

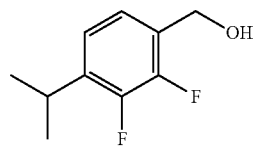

25 (1.5 g, 8.1 mmol), ammonium formate (3.0 g, 49 mmol), palladium on carbone 10% (433 mg, 0.41 mmol), THF (14 mL) and MeOH (44 mL) were refluxed for 30 min. The mixture was filtered through Celite®, washed with EtOAc, and the filtrate was concentrated. The residue was partitioned between brine and EtOAc. The organic layer was separated, dried on MgSO₄, filtered and evaporated until dryness to give 1.47 g of intermediate 26, colorless oil (97%).

e—Synthesis of Intermediate 27:

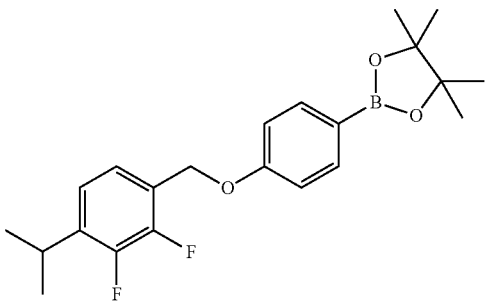 [SMILES: CC(C)c1ccc(COc2ccc(B3OC(C)(C)C(C)(C)O3)cc2)c(F)c1F]

Under N$_2$, DBAD (2.2 g, 9.5 mmol) was added portionwise to a solution of 26 (1.47 g, 7.9 mmol), 4-hydroxyphenylboronic acid pinacol ester (2.1 g, 9.5 mmol), and supported PPh$_3$ (3.0 g, 9.5 mmol) in dry THF (60 mL). The mixture was stirred at r.t. for 3 days. Supported PPh$_3$ was filtered and the filtrate was evaporated to give 8 g, yellow oil. The crude residue was purified by preparative LC (irregular SiOH 30 μm 120 g GraceResolv™, mobile phase: heptane/EtOAc 90/10). The pure fractions were collected and solvent evaporated until dryness to give 2.36 g of intermediate 27, pale yellow oil which crystallized in beige solid (77%).

f—Synthesis of Compound 8:

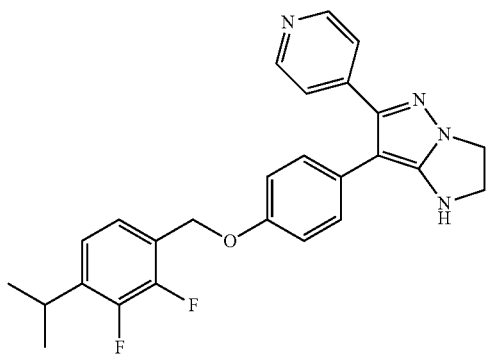 [SMILES: CC(C)c1ccc(COc2ccc(-c3c(-c4ccncc4)nn4c3NCC4)cc2)c(F)c1F]

A mixture of 10 (400 mg, 1.5 mmol), 27 (878 mg, 2.3 mmol) and K$_3$PO$_4$ (1.3 g, 6.0 mmol) in 1,4-dioxane (10 mL) and H$_2$O (3.5 mL) in a sealed tube was purged with N$_2$. Pd$_2$(dba)$_3$ (81 mg, 75 μmol) and P(tBu)$_3$.HBF$_4$ (44 mg, 0.15 mmol) were added, the mixture was purged again with N$_2$ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over MgSO$_4$, filtered off and evaporated in vacuo. The residue was purified by preparative LC (Stationary phase: GraceResolv™ 40 g, Mobile phase: 96% DCM, 4% MeOH). The pure fractions were collected and solvent evaporated until dryness to give 330 mg of colorless oil which was crystallized from Et$_2$O. The white solid formed was filtrated and dried to give 98 mg of Compound 8, white solid (15%). m.p.=149° C. (DSC).

Example A9: Preparation of Co. 28 and Co. 9 a—Synthesis of Intermediate 28:

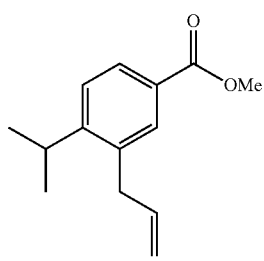 [SMILES: C=CCc1cc(C(=O)OC)ccc1C(C)C]

To a solution of methyl 3-bromo-4-isopropylbenzoate (1.2 g, 4.7 mmol) in dry DMF (36 mL) degazed under N$_2$ were added Pd(PPh$_3$)$_4$ (270 mg, 0.23 mmol) and allyltri-N-butyltin (1.85 g, 5.6 mmol). The mixture was flushed again with N$_2$ for 5 min and heated at 80° C. overnight. After cooling, the mixture was partitioned between EtOAc and brine, and the organic layer was washed twice with brine, dried and concentrated to give 3.5 g of yellow oil. This oil was purified by preparative LC (irregular SiOH 15-40 μm, 80 g, GraceResolv™, Mobile phase gradient: from 95% heptane, 5% EtOAc to 90% heptane, 10% EtOAc). The pure fractions were collected and solvent was evaporated to give 900 mg of intermediate 28, colorless oil (88%).

b—Synthesis of Intermediate 29:

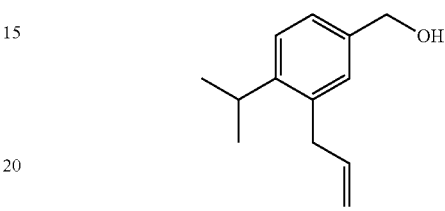

28 (900 mg, 4.1 mmol) in dry THF (6.5 mL) was added dropwise to a suspension of LAH (188 mg, 4.9 mmol) in dry THF (6.5 mL) at 0° C. under N$_2$. The mixture was stirred for 30 min. H$_2$O (1 mL) then DCM were added very slowly and stirred for 20 min. The insoluble was filtered on a pad of Celite® and the filtrate was dried over MgSO$_4$, filtered and evaporated until dryness to give 845 mg of intermediate 29, colorless oil (100%).

c—Synthesis of Intermediate 30:

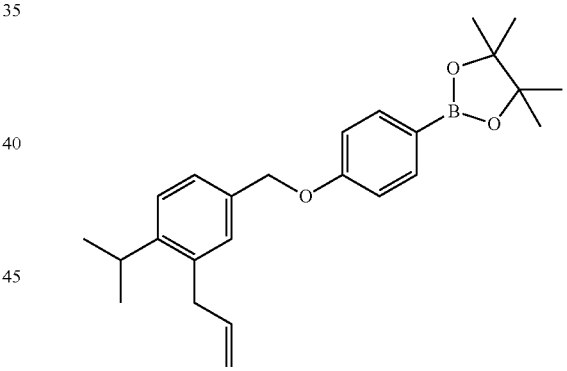

To a mixture of 29 (800 mg, 4.2 mmol), 4-hydroxyphenylboronic acid pinacol ester (1.85 g, 8.41 mmol) and diphenylphosphinopolystyrene (6.47 g, 8.41 mmol) in dry THF (56 mL) was added DBAD (1.94 g, 8.41 mmol). The mixture was stirred at r.t. for 96 h, then filtered on a glass frit and the solid was washed with EtOAc. The filtrate was evaporated in vacuo to give 5 g of pale brown residue. The residue was purified by preparative LC (Irregular SiOH 15-40 μm, 50 g Merck, liquid deposit with DCM, mobile phase: heptane 80%, EtOAc 20%). The desired fractions were collected and solvent evaporated until dryness to give 1.14 g of intermediate 30, pale brown oil (mixture with impurity, product without allyl chain). The mixture was used as a mixture in the next reaction step.

d—Synthesis of Compound 28:

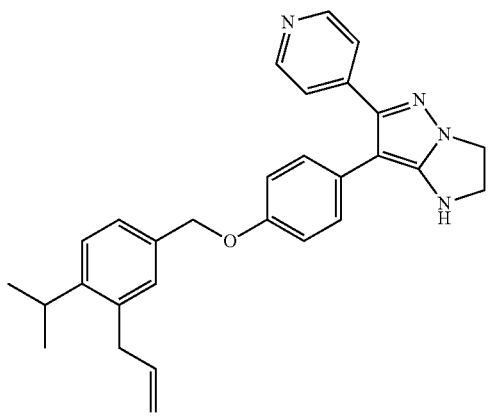 [SMILES: C=CCc1cc(COc2ccc(-c3c(-c4ccncc4)nn4c3NCC4)cc2)ccc1C(C)C]

A mixture of 10 (100 mg, 0.377 mmol), 30 (163 mg) and K₃PO₄ (320 mg, 1.51 mmol) in 1,4-dioxane (3.60 mL) and H₂O (0.80 mL) in a sealed tube was purged with N₂. Pd₂(dba)₃ (20.1 mg, 18.9 μmol) and P(tBu)₃·HBF₄ (10.9 mg, 37.7 μmol) were added, the mixture was purged again with N₂ and heated at 120° C. using one single mode microwave (Biotage Initiator EXP 60) with a power output ranging from 0 to 400 W for 30 min [fixed hold time]. The mixture was diluted with DCM and water, the organic layer was separated, dried over MgSO₄, filtered off and evaporated in vacuo to give 320 mg of intermediate 31, orange oil (mixture with impurity, product without allyl chain). The mixture was used as such in the next reaction step without purification.

e—Synthesis of Compound 9

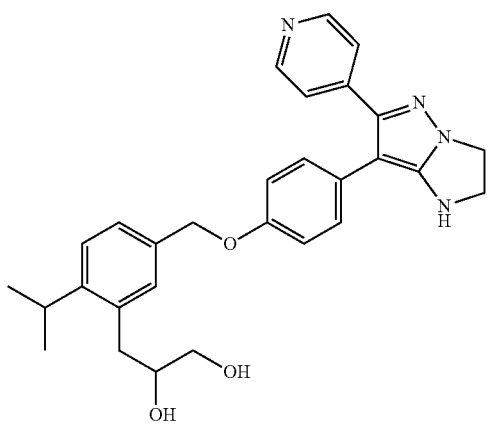 [SMILES: CC(C)c1ccc(COc2ccc(-c3c(-c4ccncc4)nn4c3NCC4)cc2)cc1CC(O)CO]

To a solution of Compound 28 (320 mg) in acetone (6.5 mL) and H₂O (790 μL) under N₂ were successively added 4-methylmorpholine-4-oxide (123 mg, 1.05 mmol) and osmium tetroxide 2.5% in butanol (590 μL, 43.8 μmol). The mixture was heated at 60° C. for 2 h. After cooling down to r.t., a 10% aqueous solution of Na₂SO₃ (4 mL) was added and the mixture was stirred for 30 min at r.t. The solvent was evaporated in vacuo and the residue was diluted with EtOAc and washed with a saturated aqueous solution of NaCl (3 times). The organic layer was dried over MgSO₄, filtered off and evaporated in vacuo to give 235 mg of black oil. The residue was purified by preparative LC (Stationary phase: irregular bare silica 40 g, Mobile phase: 0.5% NH₄OH, 95% DCM, 5% MeOH). The pure fractions were collected and solvent evaporated until dryness to give 51 mg of pale yellow foam which was triturated in Et₂O. The solid was filtered and dried to give 51 mg of Compound 9, pale brown solid (12%).

Example A10: Preparation of Co. 10 a—Synthesis of Intermediate 32:

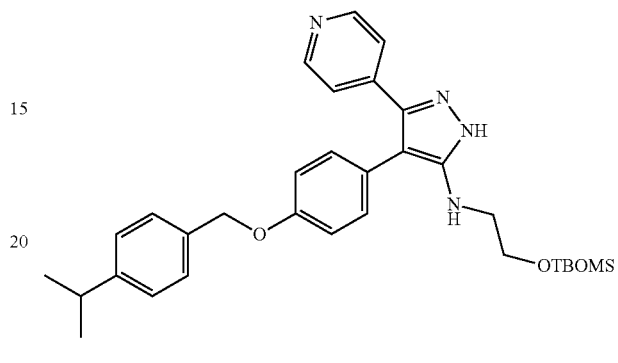

To a solution of 4 (1.5 g, 3.9 mmol) in DCE (20 mL) were added (tert-butyldimethylsilyloxy)acetate (1.1 mL, 5.8 mmol) and sodium triacetoxyborohydride (2.5 g, 11.7 mmol) and the mixture was heated at 50° C. for 3 h. The mixture was poured out into a mixture of water and a saturated aqueous solution of NaCl and DCM was added. The organic layer was separated, dried over MgSO₄, filtered off and evaporated in vacuo. The residue was purified by preparative LC (Irregular SiOH 15-40 μm, 50 g Merck, mobile phase gradient: from DCM 100% to DCM 95%, MeOH 5%). The pure fractions were collected and solvent evaporated until dryness to give 1.4 g of intermediate 32 (66%).

b—Synthesis of Intermediate 33:

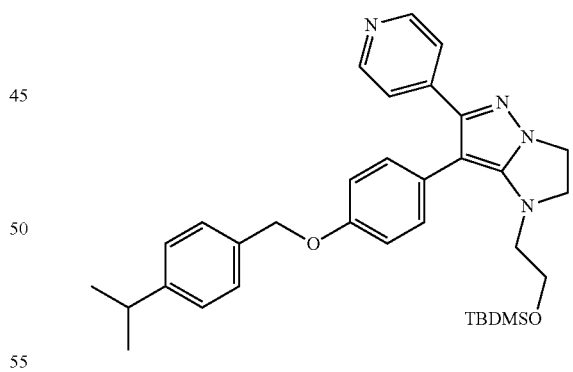

To a solution of 32 (1.4 g, 2.6 mmol) in DMF (20 mL) was added DIPEA (1.1 mL, 6.5 mmol) and 5 (1.4 g, 3.2 mmol). The solution was heated at 90° C. overnight then cooled down to r.t. The crude mixture was diluted with EtOAc and washed with a saturated aqueous solution of NaCl (twice). The organic layer was separated, dried over MgSO₄, filtered off and evaporated to give 2.5 g. The residue was purified by preparative LC (Stationary phase: irregular SiOH 15-40 μm 300 g MERCK, Mobile phase: 60% Heptane, 5% MeOH, 35% EtOAc). The pure fractions were collected and evaporated till dryness to give 220 mg of intermediate 33 (15%).

c—Synthesis of Compound 10

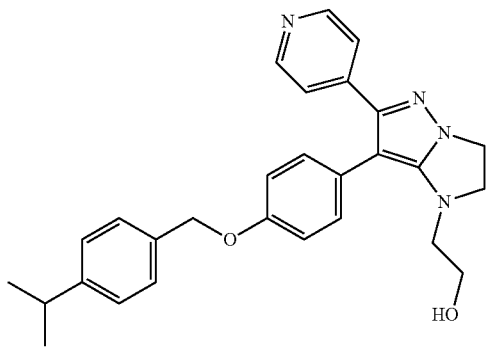 [SMILES: CC(C)c1ccc(COc2ccc(-c3c(-c4ccncc4)nn4c3N(CCO)CC4)cc2)cc1]

TBAF (0.5 mL, 0.5 mmol) was added to a solution of 33 (220 mg, 0.38 mmol) in THF (5 mL). The mixture was stirred at r.t. for 3 h. Water and EtOAc were added and the mixture was extracted. The organic layer was separated, dried over $MgSO_4$, filtered and evaporated until dryness to give 142 mg which was crystallized from $Et_2O$. The solid was filtered off and dried to give 95 mg of Compound 10 (54%). m.p.=151° C. (DSC).

Example A11: Preparation of Co. 11 a—Synthesis of Intermediate 34:

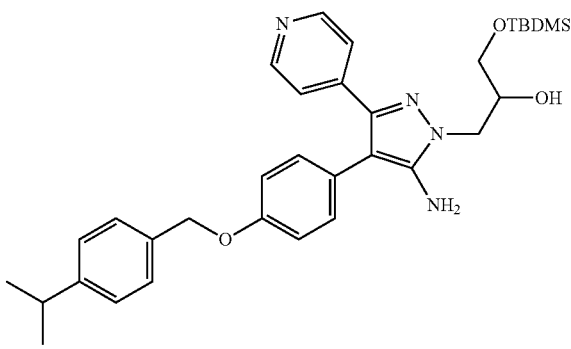 [SMILES: CC(C)c1ccc(COc2ccc(-c3c(-c4ccncc4)nn(CC(O)CO[Si](C)(C)C(C)(C)C)c3N)cc2)cc1]

4 (2.5 g, 6.5 mmol) was added to a suspension of tert-butyldimethylsilyl glycidyl ether (1.3 g, 7.1 mmol), and $K_2CO_3$ (4.5 g, 32.5 mmol) in DMF (40 mL). The mixture was heated for 48 h at 70° C. Water and EtOAc were added and the mixture was extracted. The organic layer was separated, dried over $MgSO_4$, filtered and evaporated. The residue was purified by preparative LC (Stationary phase: Irregular SiOH 20-45 µm 45 g MATREX, Mobile phase: 38% Heptane, 12% MeOH (+10% $NH_4OH$), 50% EtOAc). The pure fractions were collected and solvent evaporated until dryness to give 200 mg of intermediate 34 (5%).

b—Synthesis of Compound 11

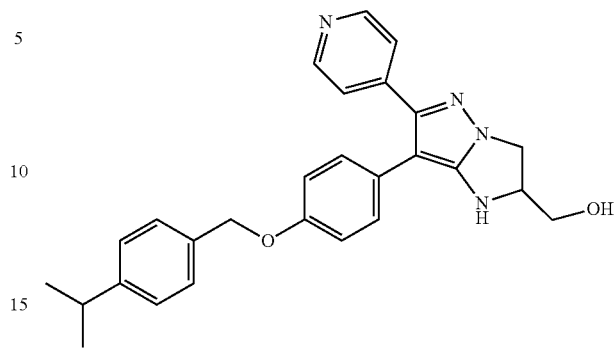

Methanesulfonyl chloride (46 µl, 0.6 mmol) was added dropwise to a solution of 34 (200 mg, 0.35 mmol), $Et_3N$ (0.27 mL, 2 mmol) in ACN (5 mL). The mixture was stirred at 100° C. for 6 h. Water and EtOAc were added and the mixture was extracted. The organic layer was separated, dried over $MgSO_4$, filtered and evaporated to give 220 mg. The residue was purified by preparative LC on (Stationary phase: Irregular SiOH 20-45 µm 12 g, GRACE, Mobile phase: 95/5/0.1, DCM/MeOH/$NH_4OH$). The desired fractions were collected and the solvent was evaporated until dryness to give 23 mg of a residue which was purified by preparative LC (Stationary phase: irregular bare silica 40 g, Mobile phase: 0.5% $NH_4OH$, 94% DCM, 6% MeOH). The pure fractions were combined and the solvent was evaporated until dryness to give 13 mg of Compound 11 (8%).

Example A12: Preparation of Co. 12 a—Synthesis of Intermediate 35:

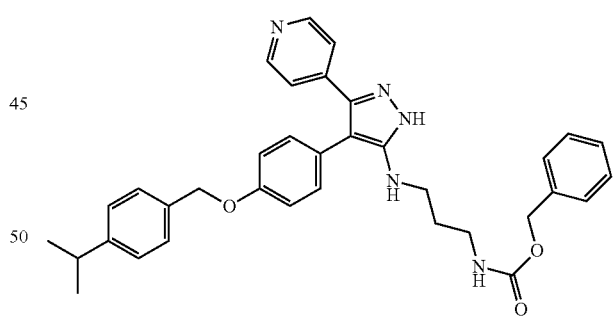

To a solution of 4 (1.48 g, 3.8 mmol) and 3-[(benzyloxycarbonyl)amino]propionaldehyde (1.2 g, 5.8 mmol) in DCE (20 mL) were added $NaBH(OAc)_3$ (2.5 g, 11.5 mmol) and the mixture was heated at 50° C. for 2.5 hours. The mixture was poured into a mixture of water and a saturated aqueous solution of NaCl and DCM was added. The organic layer was separated, dried over $MgSO_4$, filtered off and evaporated in vacuo. The residue was purified by preparative LC (irregular SiOH 15-40 µm, 40 g Interchim, mobile phase: DCM 94%, MeOH 6%, $NH_4OH$ 0.1%). The pure fractions were collected and solvent evaporated until dryness to give 1.1 g of intermediate 35, colorless oil (50%).

b—Synthesis of Intermediate 36:

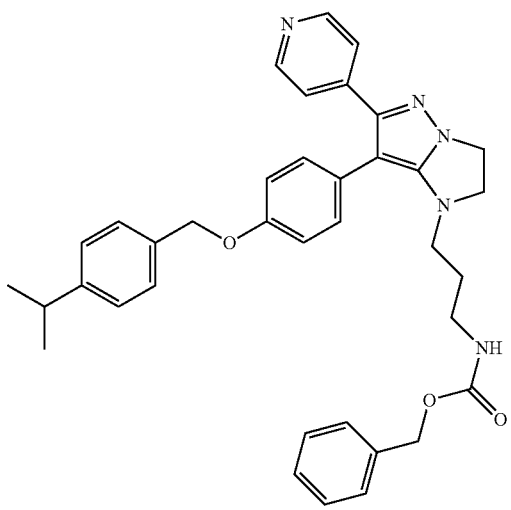 [SMILES: CC(C)c1ccc(COc2ccc(-c3c(-c4ccncc4)nn4c3N(CCCNC(=O)OCc3ccccc3)CC4)cc2)cc1]

To a solution of 35 (1.1 g, 1.9 mmol) in DMF (15 mL) was added DIPEA (0.82 mL, 4.8 mmol) and 5 (1.1 g, 2.4 mmol). The solution was heated at 90° C. overnight then cooled down to r.t. The crude mixture was diluted with EtOAc and washed with a saturated aqueous solution of NaCl (twice). The organic layer was separated, dried over MgSO$_4$, filtered off and evaporated. The residue was purified by preparative LC (Stationary phase: irregular SiOH 15-40 µm 40 g, GraceResolv, Mobile phase gradient: DCM/MeOH/NH$_4$OH, from 100/0/0 to 95/5/0.1). The desired fractions were collected and solvent evaporated until dryness to give 120 mg of intermediate 36, colorless oil (10%).

c—Synthesis of Compound 12

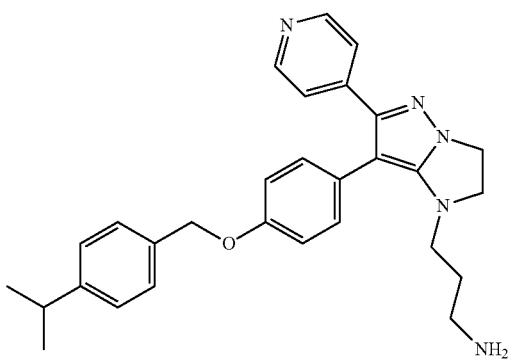 [SMILES: CC(C)c1ccc(COc2ccc(-c3c(-c4ccncc4)nn4c3N(CCCN)CC4)cc2)cc1]

TBAF (0.7 mL, 1.0 mmol) was added dropwise to a solution of 36 (0.12 g, 0.14 mmol) in THF (3.4 mL) at r.t. The mixture was stirred under reflux overnight. The mixture was concentrated to give 320 mg, purple oil. The residue was purified by preparative LC (Stationary phase: irregular bare silica 40 g, Mobile phase: 0.5% NH$_4$OH, 92% DCM, 8% MeOH). The desired fractions were collected and solvent evaporated to give 57 mg. The residue was purified by achiral SFC (Stationary phase: 2-ethylpyridine 6 µm 150× 21.2 mm, Mobile phase: 80% CO$_2$, 20% MeOH (0.3% iPrNH$_2$)). The pure fractions were collected and solvent evaporated until dryness to give 42 mg of residue which was taken up in ACN and water (1/5, 20 mL) and lyophilized to give 35 mg of Compound 12, beige powder (54%).

Example A13: Preparation of Co. 13 a—Synthesis of Intermediate 37:

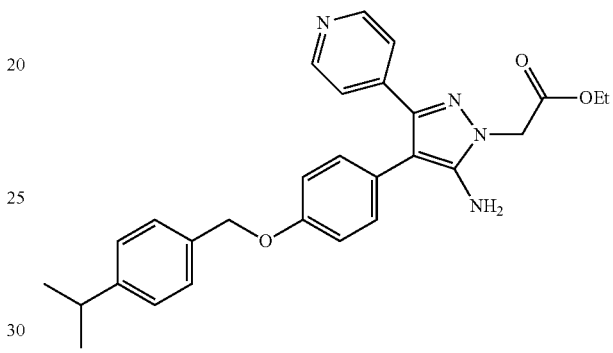

To a solution of 4 (100 mg, 0.26 mmol) in dry DMF (1.5 mL) was added NaH 60% (11.4 mg, 0.29 mmol). After 15 min, ethyl chloroacetate (30.8 µL, 0.29 mmol) was added. After 30 min, the reaction mixture was quenched with ice and diluted with water. The aqueous layer was extracted with DCM (3×25 mL) and the combined organic layers were dried over MgSO$_4$, evaporated in vacuo to afford 140 mg which was triturated in Et$_2$O and filtered off to afford 103 mg of intermediate 37, yellow solid (84%).

b—Synthesis of Intermediate 38:

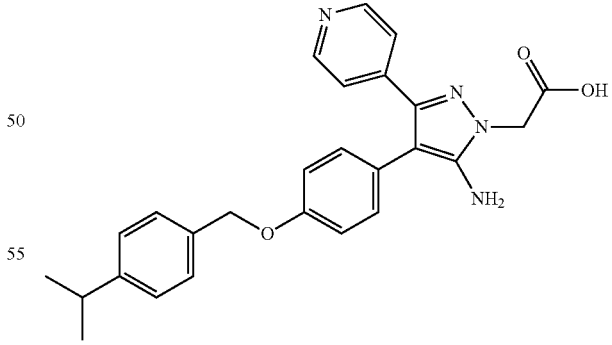

To a solution of 37 (337 mg, 0.72 mmol) in a mixture of EtOH (6.5 mL) and H$_2$O (6.5 mL) was added KOH (402 mg, 7.16 mmol). The reaction mixture was refluxed for 2 h and cooled down to r.t. After evaporation under reduced pressure, the crude was taken-up in 1N HCl and the yellow precipitate was filtered to afford 339 mg of intermediate 38, yellow powder (quantitative).

c—Synthesis of Compound 13

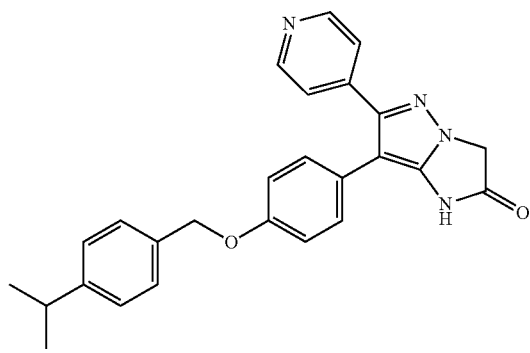 [SMILES: CC(C)c1ccc(COc2ccc(-c3c(-c4ccncc4)nn4c3NC(=O)C4)cc2)cc1]

To a mixture of 38 (297 mg, 0.62 mmol) in DMF (7 mL) was successively added EDCI (192 mg, 1.24 mmol), HOBT (92.1 mg, 0.68 mmol) and dropwise Et$_3$N (0.27 mL, 1.92 mmol). The reaction mixture was stirred at r.t. overnight and diluted with water. The organic layer was extracted with DCM (3×75 mL) and the combined organic layers were washed with a 10% solution of KHSO$_4$ (50 mL), a saturated solution of NaHCO$_3$ (50 mL), brine (50 mL), dried over MgSO$_4$ and filtered. The solvent was evaporated in vacuo and afforded 102 mg of yellow solid which was triturated in iPr$_2$O, filtered off and dried to afford 85 mg of Compound 13, yellow solid (32%). m.p.=157° C., 248° C. (polymorph, DSC).

Example A14: Preparation of Co. 14 a—Synthesis of Intermediate 39:

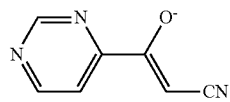 [SMILES: N#C/C=C(\[O-])c1ccncn1]

To a solution of methyl pyrimidine-4-carboxylate (10.0 g, 72.4 mmol) and ACN (1.89 mL, 36.2 mmol) in dry THF (100 mL) was added slowly potassium 2-methyl-2-butoxide in toluene (16.8 mL, 29.0 mmol). The reaction was stirred at r.t. for 18 h, quenched with water and evaporated in vacuo. The solid was taken up with a minimum of cold EtOH, filtered on a glass frit, washed with Et$_2$O (3 times) and dried to give 5.55 g of intermediate 39, brown solid (83%). Intermediate 39 was used without purification in the next reaction step.

b—Synthesis of Intermediate 40:

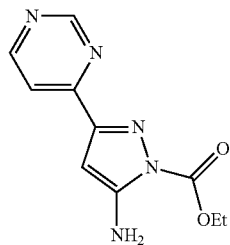 [SMILES: CCOC(=O)n1nc(-c2ccncn2)cc1N]

To a suspension of 39 (5.55 g, 30.0 mmol) in EtOH (64 mL) were added ethyl carbazate (4.78 g, 45.9 mmol) and HCl 37% in H$_2$O (3.52 mL, 42.2 mmol). The mixture was stirred at 50° C. for 1 h then cooled down to r.t. The precipitate was filtered on a glass frit and rinsed with EtOH. The filtrate was evaporated in vacuo and taken-up in DCM. The organic layer was washed with a saturated aqueous solution of NaHCO$_3$, dried over MgSO$_4$ and evaporated in vacuo to give 3.68 g of intermediate 40, yellow oil which crystallized (53%).

c—Synthesis of Intermediate 41:

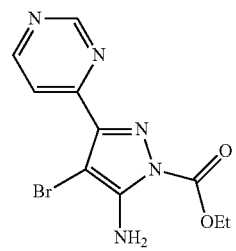 [SMILES: CCOC(=O)n1nc(-c2ccncn2)c(Br)c1N]

To a solution of 40 (3.68 g, 15.8 mmol) in DCM (140 mL) at 0° C. was added NBS (3.09 g, 17.4 mmol) portionwise. The mixture was stirred at 0° C. for 1 h then water was added. The organic layer was separated, dried over MgSO$_4$, filtered off and evaporated in vacuo to give brown oil which was triturated in Et$_2$O and dried in vacuo to give 4.24 g of intermediate 41, brown solid (86%).

d—Synthesis of Intermediate 42:

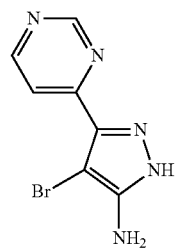 [SMILES: Nc1[nH]nc(-c2ccncn2)c1Br]

To a solution of 41 (4.24 g, 13.6 mmol) in MeOH (130 mL) was added Et$_3$N (18.9 mL, 136 mmol), the solution was stirred at r.t. for 18 h and the solvent was evaporated in vacuo to give a brown oil. The oil was diluted in a minimum of DCM and Et$_2$O was added. The precipitate formed was filtered on a glass frit to give a brown solid residue. The filtrate was evaporated in vacuo to give a brown residue which was purified by preparative LC (Irregular SiOH 15-40 µm, 80 g Grace, solid deposit, mobile phase gradient: from DCM 100% to DCM 90%, MeOH 10%). The pure fractions were collected and solvent evaporated until dryness to give 1.18 g of intermediate 42, white solid (36%).

e—Synthesis of Intermediate 43:

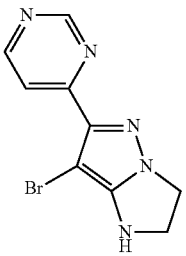

To a solution of 42 (1.15 g, 4.79 mmol) in DMF (18 mL) was added DIPEA (2.06 mL, 12.0 mmol) and 5 (1.69 g, 5.75 mmol). The solution was heated at 90° C. for 18 h then cooled down to r.t. and evaporated in vacuo to give 4.22 g of black oil. The residue was purified by preparative LC (Irregular SiOH 15-40 µm, 120 g Grace, solid deposit, mobile phase gradient: from DCM 100% to DCM 95%, MeOH 5%). The pure fractions were collected and solvent was evaporated until dryness to give 448 mg of intermediate 43, off-white solid (35%).

f—Synthesis of Intermediate 44:

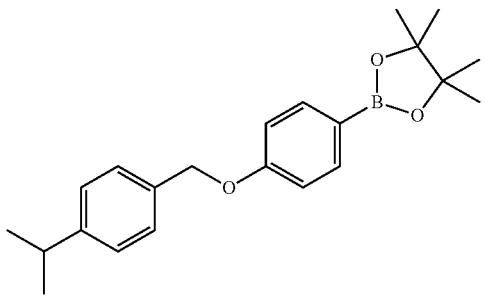 [SMILES: CC(C)c1ccc(COc2ccc(B3OC(C)(C)C(C)(C)O3)cc2)cc1]

First Method:

To a suspension of 4-hydroxybenzeneboronic acid pinacol ester (5.00 g, 22.7 mmol), 4-(1-methylethyl)-benzenemethanol (5.12 g, 34.1 mmol), and supported PPh₃ (8.94 g; 34.1 mmol) in dry DCM (150 mL) was added DBAD (7.85 g, 34.1 mmol) and the reaction mixture was stirred at r.t. for 18 h. The reaction mixture was then filtered through a glass frit and washed with EtOAc. The filtrate was evaporated in vacuo to give a residue (27 g), yellow oil. The residue was purified by chromatography over silica gel (irregular SiOH 15-40 µm, 150 g, mobile phase: 90% Heptane, 10% EtOAc). The pure fractions were collected and the solvent evaporated to give 8.00 g of intermediate 44, white gum (quantitative).

Second Method:

A solution of 4-isopropylbenzyl bromide (7.00 g, 31.8 mmol) in ACN (75 mL) was treated with $K_2CO_3$ (5.28 g, 38.2 mmol) and 4-hydroxybenzeneboronic acid pinacol ester (6.03 mL, 35.0 mmol) at r.t. The r.m. was stirred at r.t. overnight. Then, the reaction mixture was filtered on a pad of Celite® and rinsed with DCM. The solvents were evaporated to a volume of 100 mL and $Et_2O$ and heptane were added. The solvents were evaporated in vacuo to afford 12.36 g of yellow solid residue. This residue was purified by preparative LC (Regular SiOH 50 µm, 220 g Grace, mobile phase gradient: from Heptane 100% to Heptane 80%, EtOAc 20%). The pure fractions were collected and solvent evaporated until dryness to give 9.88 g of the intermediate 44, white sticky solid (88%).

g—Synthesis of Compound 14

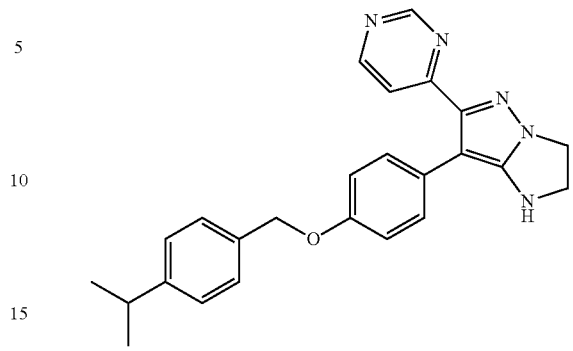

A mixture of 43 (150 mg, 564 µmol), 44 (200 mg, 564 µmol) and $K_3PO_4$ (479 mg, 2.26 mmol) in 1,4-dioxane (5.60 mL) and $H_2O$ (1.20 mL) in a sealed tube was purged with $N_2$. $Pd_2(dba)_3$ (30.1 mg, 28.2 µmol) and $P(tBu)_3.HBF_4$ (16.4 mg, 56.4 µmol) were added, the mixture was purged again with $N_2$ and heated at 60° C. for 18 h. The mixture was diluted with DCM and water, the organic layer was separated, dried over $MgSO_4$, filtered off and evaporated in vacuo to give 866 mg of brown residue. The residue was purified by preparative LC (Stationary phase: Spherical bare silica 5 µm 150×30.0 mm, Mobile phase Gradient: from 71% Heptane, 1% MeOH (+10% $NH_4OH$), 28% EtOAc to 0% Heptane, 20% MeOH (+10% $NH_4OH$), 80% EtOAc). The pure fractions were collected and solvent evaporated until dryness to give colorless oil which was triturated in $Et_2O$ and dried in vacuo to give 36 mg of Compound 14, pale yellow solid (16%). m.p.=109° C. (dsc).

Example A15: Preparation of Co. 15

A mixture of 43 (150 mg, 564 µmol), 18 (209 mg, 564 µmol) and $K_3PO_4$ (479 mg, 2.26 mmol) in 1,4-dioxane (5.60 mL) and $H_2O$ (1.20 mL) in a sealed tube was purged with $N_2$. $Pd_2(dba)_3$ (30.1 mg; 28.2 µmol) and $P(tBu)_3.HBF_4$ (16.4 mg, 56.4 µmol) were added, the mixture was purged again with $N_2$ and heated at 60° C. for 18 h. The mixture was diluted with DCM and water, the organic layer was separated, dried over $MgSO_4$, filtered off and evaporated in vacuo to give 350 mg. The residue was purified by preparative LC (Stationary phase: Spherical bare silica 5 µm 150× 30.0 mm, Mobile phase Gradient: from 71% Heptane, 1% MeOH (+10% $NH_4OH$), 28% EtOAc to 0% Heptane, 20% MeOH (+10% $NH_4OH$), 80% EtOAc). The pure fractions were collected and solvent evaporated until dryness to give colorless oil which was triturated in $Et_2O$ and dried in vacuo to give 11 mg of Compound 15, yellow foam (5%).

Example A16: Preparation of Co. 16 a—Synthesis of Intermediate 45:

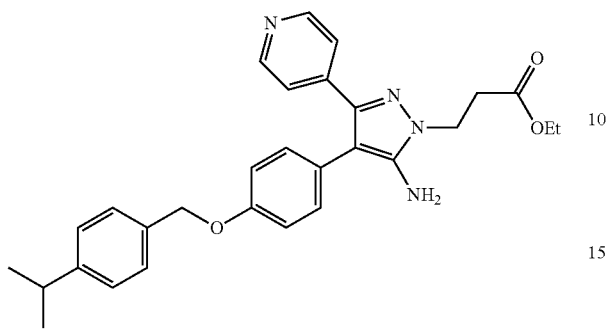

To a suspension of 4 (2.00 g, 5.20 mmol) in pyridine (838 µL) was added ethyl acrylate (11.0 mL, 10 3 mmol). The reaction was heated at 150° C. using one single mode microwave (Biotage Initiator EXP 60) with a power output ranging from 0 to 400 W for 1 h [fixed hold time]. The reaction mixture was cooled down to r.t. and the precipitate was filtered off and washed with Et$_2$O to give 1.50 g of intermediate 45, white solid (60%). Int. 45 was used without purification in the next reaction step.

b—Synthesis of Compound 16

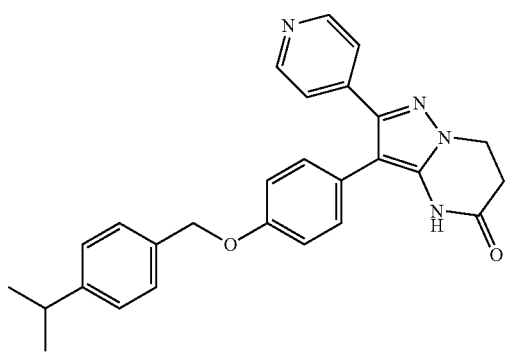 [SMILES: CC(C)c1ccc(COc2ccc(-c3c(-c4ccncc4)nn4c3NC(=O)CC4)cc2)cc1]

To a stirred mixture of 45 (478 mg, 0.986 mmol) in MeOH (15 mL) was added Cs$_2$CO$_3$ (1.61 g, 4.93 mmol). After 1 h 30, the reaction was evaporated to dryness and taken-up in DCM (100 mL). The organic layer was washed with water (100 mL), brine (100 mL) and dried over MgSO$_4$. The solvent was evaporated in vacuo to afford 771 mg of beige solid. The solid was dissolved in ACN (20 mL) and iPr$_2$O (100 mL) was added. The precipitate was filtered off. The filtrate was evaporated in vacuo to afford 229 mg of beige solid which was purified by preparative LC (Regular SiOH 50 µm, 24 g Grace, dry loading, mobile phase gradient: from DCM 100% to DCM 60%, acetone 40%). The pure fractions were collected and solvent evaporated until dryness to give 85 mg of Compound 16, white solid (20%). m.p.=290° C. (dsc).

Example A17: Preparation of Co. 17 and Co. A

First Method:

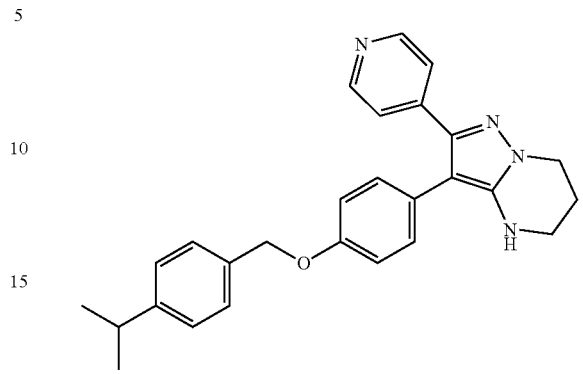

To a mixture of Compound 16 (175 mg, 0.399 mmol) in THF (5 mL) was added dropwise borane tetrahydrofuran complex (2.00 mL, 1.99 mmol). The reaction was heated at 70° C. for 2 h and cooled down to r.t. Then, MeOH (2 mL) was carefully added before the addition of 6N HCl (2 mL). The homogeneous solution was stirred at r.t. for 30 min and evaporated in vacuo. The crude mixture was then basified with a 30% solution of NaOH until pH 14. The aqueous layer was extracted with DCM (3×50 mL) and the combined organic layers were washed with a saturated solution of NaCl, dried over MgSO$_4$ and evaporated in vacuo to afford 98 mg of light yellow solid. The residue was purified by preparative LC (Regular SiOH 50 µm, 24 g Grace, solid sample, mobile phase gradient: from DCM 100% to DCM 60%, Acetone 40%). The pure fractions were collected and solvent evaporated until dryness. The residue was triturated in Et$_2$O, filtered and dried to give 36 mg of Compound 17, white powder (21%). m.p.=205° C. (dsc).

Second Method:

a—Synthesis of Compound A (Co. of Formula (I'))

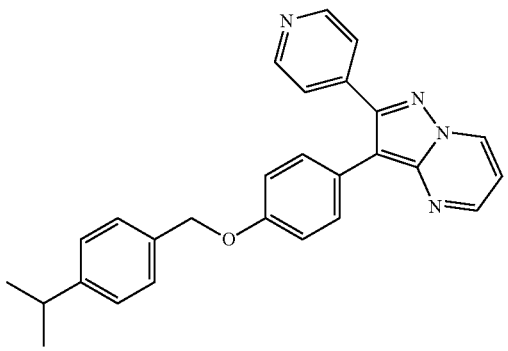 [SMILES: CC(C)c1ccc(COc2ccc(-c3c(-c4ccncc4)nn4cccnc34)cc2)cc1]

To a solution of 4 (5.00 g, 13.0 mmol) in acetic acid (50 mL) was added 1,1,3,3-tetramethoxypropane (2.57 mL, 15.6 mmol). The mixture was heated at 110° C. for 16 h. The mixture was evaporated to dryness and co-evaporated with toluene (3 times). The residue was taken-up in DCM and washed with a saturated aqueous solution of NaHCO$_3$, water and brine. The organic layer was dried over MgSO$_4$, filtered and evaporated in vacuo to give 5.43 g of Compound A, brown solid (99%). The product was used in the next step without further purification.

b—Synthesis of Co. 17

To a mixture of Compound A (600 mg, 1.43 mmol) in EtOH (6 mL) at r.t. was added NaBH$_4$ (108 mg, 2.85 mmol). The mixture was heated at 80° C. for 1 h then cooled down to r.t., quenched with water and evaporated until dryness. The residue was taken up in DCM and washed with water. The organic layer was separated, dried over MgSO$_4$, filtered off and evaporated in vacuo to give 600 mg of Co. 17, yellow solid (99%).

Example A18: Preparation of Co. 18 and Co. B a—Synthesis of Intermediate 47:

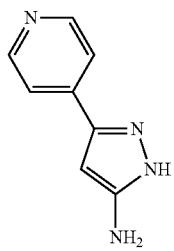 [SMILES: Nc1cc(-c2ccncc2)n[nH]1]

To a solution of 6 (500 mg, 2.71 mmol) in EtOH (5 mL) at 0° C. were added HCl 37% in water (0.25 mL) and ethyl carbazate (339 mg, 3.26 mmol). The solution was stirred at r.t. for 18 h and then K$_2$CO$_3$ (225 mg, 1.63 mmol) was added. The mixture was heated at 90° C. for 1 h and was then evaporated in vacuo. The residue was diluted with EtOAc and washed with water. The aqueous layer was extracted twice with EtOAc. The combined organic layers were dried over MgSO$_4$, filtered off and evaporated in vacuo to give 315 mg which was triturated in Et$_2$O and filtered on a glass frit to give 161 mg of intermediate 47, white solid (37%).

b—Synthesis of Intermediate 48:

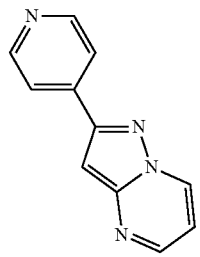 [SMILES: c1cnc2cc(-c3ccncc3)nn2c1]

To a solution of 47 (161 mg, 1.00 mmol) in acetic acid (2.8 mL) was added 1,1,3,3-tetramethoxypropane (0.199 mL, 1.21 mmol). The solution was heated at 110° C. for 16 h, then, evaporated in vacuo and co-evaporated with toluene twice. The residue was dissolved in DCM and neutralized with a saturated aqueous solution of NaHCO$_3$. The organic layer was separated, dried over MgSO$_4$, filtered off and evaporated in vacuo to give 189 mg of intermediate 48, beige solid (96%).

c—Synthesis of Intermediate 49:

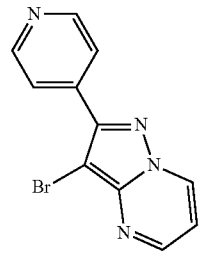 [SMILES: Brc1c(-c2ccncc2)nn2cccnc12]

To a solution of 48 (560 mg, 2.85 mmol) in ACN (10 mL) was added dropwise NBS (533 mg, 3.00 mmol) in ACN (10 mL) at r.t. The solution was stirred at r.t. for 1 h and the solvent was removed in vacuo. DCM and a saturated aqueous solution of NaHCO$_3$ were added to the residue, the organic layer was separated, dried over MgSO$_4$, filtered off and evaporated in vacuo to give 900 mg of intermediate 49 as white solid (quantitative yield).

d—Synthesis of Compound B (Co. of Formula (I'))

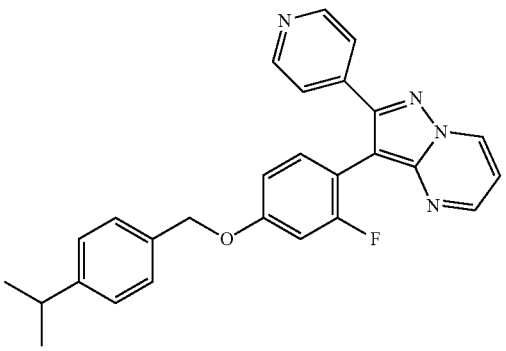 [SMILES: CC(C)c1ccc(COc2ccc(-c3c(-c4ccncc4)nn4cccnc34)c(F)c2)cc1]

In a sealed tube, a mixture of 49 (470 mg, 1.71 mmol), 18 (949 mg, 2.56 mmol) and K$_3$PO$_4$ (1.45 g, 6.83 mmol) in 1,4-dioxane (7.50 mL) and H$_2$O (2.70 mL) was carefully purged with N$_2$. PdCl$_2$(dppf)$_2$ (140 mg, 171 μmol) was added and the reaction mixture was purged once again with N$_2$. The tube was then sealed and the reaction mixture was heated at 80° C. for 18 h. The crude material was diluted in DCM and washed with water. The organic layer was separated, dried over MgSO$_4$ and evaporated in vacuo to give 986 mg of brown oil. This oil and another batch (with 100 mg of reactant 49 in the same conditions) were combined and purified by preparative LC (Irregular SiOH 15-40 μm, 80 g Grace, mobile phase gradient: from DCM 100% to DCM 90%, acetone 10%). The pure fractions were collected and solvent evaporated until dryness to give 635 mg of yellow oil which crystallized. The residue was triturated once in Et$_2$O, twice in pentane, filtered off and dried in vacuo to give 517 mg of Compound B, pale yellow solid (57%). m.p.=187° C. (DSC).

e—Synthesis of Co. 18

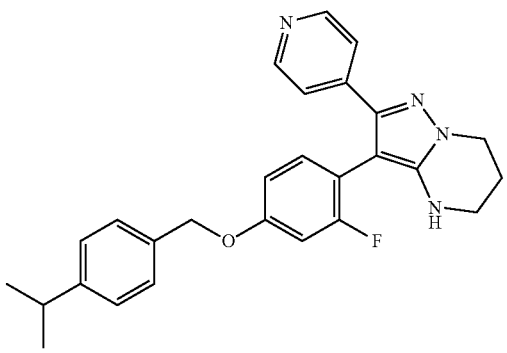 [SMILES: CC(C)c1ccc(COc2ccc(-c3c(-c4ccncc4)nn4c3NCCC4)c(F)c2)cc1]

To a mixture of Compound B (100 mg, 0.228 mmol) in EtOH (1 mL) at rt was added NaBH$_4$ (17 mg, 0.456 mmol). The mixture was heated at 80° C. for 1 h, and was then cooled down to r.t. This mixture and another batch in the same conditions, with same quantities, were combined, quenched with water and evaporated until dryness. The residue was taken up in DCM and washed with water. The organic layer was separated, dried over MgSO$_4$, filtered off and evaporated in vacuo to give a yellow oil which crystallized. The product was triturated in Et$_2$O and filtered on a glass frit to give 108 mg of a pale yellow solid. The solid and the filtrate were combined and purified by preparative LC (Irregular SiOH 15-40 µm, 24 g Grace, mobile phase gradient: from DCM 100% to DCM 98%, MeOH 2%). The pure fractions were collected and solvent evaporated until dryness to give pale yellow oil which was triturated in Et$_2$O. The off-white solid obtained was filtered and dried in vacuo to give 143 mg of Compound 18 (71%). m.p.=188° C. (DSC).

Example A19: Preparation of Co. 19

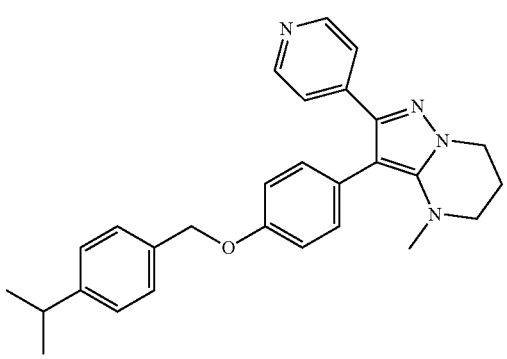 [SMILES: CC(C)c1ccc(COc2ccc(-c3c(-c4ccncc4)nn4c3N(C)CCC4)cc2)cc1]

To a solution of Compound 17 (300 mg, 0.707 mmol) in DCM (7.2 mL) were added paraformaldehyde (21 mg, 2 eq of monomer) and NaBH(OAc)$_3$ (600 mg, 2.83 mmol) and the mixture was heated at 50° C. for 18 h. Then paraformaldehyde (21 mg, 2 eq of monomer) and NaBH(OAc)$_3$ (300 mg, 1.41 mmol) were added and the mixture was refluxed for 3 h. After cooling down to r.t., water and DCM were added. The organic layer was separated, washed with a saturated aqueous solution of NaCl, dried over MgSO$_4$, filtered off and evaporated in vacuo to give a residue. This residue and another batch (with 50 mg of Co. 17 in the same conditions) were combined and purified by preparative LC (Irregular SiOH 15-40 µm, 10 g Merck, mobile phase gradient: from DCM 70%, EtOAc 30% to DCM 20%, EtOAc 80%). The desired fractions were collected and solvent evaporated until dryness to give colorless oil which was triturated in Et$_2$O, filtered and dried to give 226 mg of off-white solid. This solid was purified again by achiral SFC (Stationary phase: Chiralpak IA 5 µm 250*20 mm, mobile phase: 70% CO$_2$, 30% MeOH). The pure fractions were collected and solvent evaporated until dryness to give colorless oil which was triturated in Et$_2$O, filtered and dried to give 137 mg of product which was carefully heated in a minimum of MeOH until complete dissolution. The solvent was then allowed to slowly evaporate overnight at r.t. The solid was dried in vacuo (45° C.) overnight to give 134 mg of Compound 19, white solid (37%). m.p.=120° C. (DSC).

Example A20: Preparation of Co. 20 a—Synthesis of Intermediate 51:

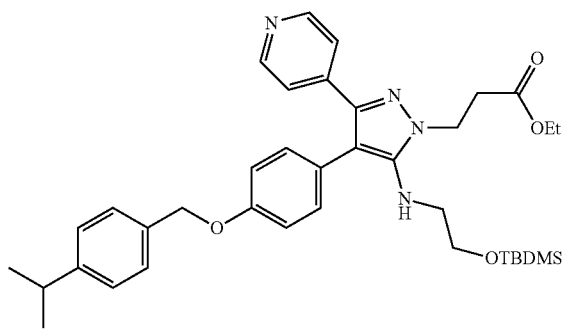 [SMILES: CCOC(=O)CCn1nc(-c2ccncc2)c(-c2ccc(OCc3ccc(C(C)C)cc3)cc2)c1NCCO[Si](C)(C)C(C)(C)C]

To a solution of 45 (1.50 g, 3.10 mmol) in DCE (30 mL) were added (tert-butyldimethylsilyloxy)acetate (1.17 mL, 6.19 mmol) and NaBH(OAc)$_3$ (2.62 g, 12.4 mmol) and the mixture was stirred at r.t. for 96 h. Water and DCM were added to the mixture, the organic layer was separated, dried over MgSO$_4$, filtered off and evaporated in vacuo to give 4.3 g of yellow residue. The residue was triturated in Et$_2$O, the precipitate was filtered off on a glass frit and washed with Et$_2$O (twice). The filtrate was evaporated in vacuo to give 2.68 g of intermediate 51, yellow oil (quantitative; purity 91%).

b—Synthesis of Intermediate 52:

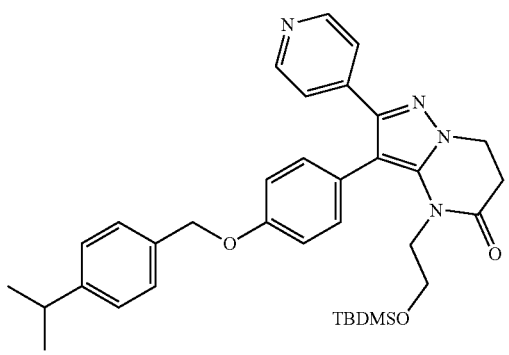 [SMILES: CC(C)c1ccc(COc2ccc(-c3c(-c4ccncc4)nn4c3N(CCO[Si](C)(C)C(C)(C)C)C(=O)CC4)cc2)cc1]

To a suspension of 51 (1.30 g; impure) in MeOH (10 mL) was added Cs$_2$CO$_3$ (2.27 g, 6.98 mmol) and the mixture was stirred at r.t. for 18 h. The solvent was removed in vacuo and the residue was diluted with DCM and water. The organic layer was separated, dried over MgSO$_4$, filtered off and evaporated in vacuo. The solid obtained was triturated in Et$_2$O and filtered on a glass frit to give a white solid. The filtrate was evaporated in vacuo to give 660 mg of a pale yellow oil which was purified by preparative LC (Irregular SiOH 15-40 μm, 30 g Merck, mobile phase gradient: from DCM 100% to DCM 90%, MeOH 10%). The pure fractions were collected and solvent evaporated until dryness to give 255 mg of intermediate 52, colorless oil and 17 mg of Compound 20, white solid (3%).

c—Synthesis of Compound 20

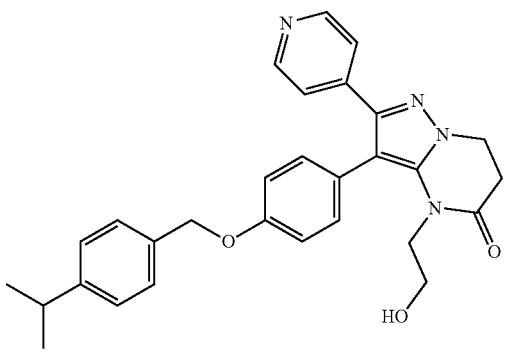 [SMILES: CC(C)c1ccc(COc2ccc(-c3c(-c4ccncc4)nn4c3N(CCO)C(=O)CC4)cc2)cc1]

To a solution of 52 (255 mg, 0.427 mmol) in THF (4.30 mL) at 0° C. was added TBAF (430 μL, 0.430 mmol). The reaction mixture was stirred at 0° C. for 2 h and at r.t. for 20 h. The crude mixture was diluted with water and DCM. The organic layer was washed with brine, dried over MgSO$_4$, filtered off and evaporated in vacuo to give 216 mg of a white solid. 216 mg and 17 mg (obtained in the previous step) were combined to give 233 mg which was recrystallized, carefully heated in a minimum of EtOH until complete dissolution. After cooling, the precipitate was filtered on a glass frit and the solid was washed with Et$_2$O (twice) then dried under high vacuum at 50° C. for 18 h to give 178 mg of Compound 20, white solid (81%). m.p.=205° C. (DSC).

Example A21: Preparation of Co. 21

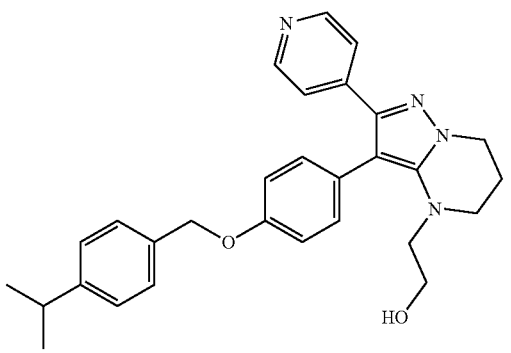 [SMILES: CC(C)c1ccc(COc2ccc(-c3c(-c4ccncc4)nn4c3N(CCO)CCC4)cc2)cc1]

To a solution of 52 (500 mg, 838 μmol) in THF (10 mL) was added dropwise BH$_3$.THF (4.20 mL, 4.20 mmol). The solution was heated at 70° C. for 2 h and cooled down to r.t. A 3N aqueous solution of HCl was added and the solution was stirred for 15 min. A 10% aqueous solution of K$_2$CO$_3$ was then added to reach pH 10 and EtOAc was added. The organic layer was separated, dried over MgSO$_4$, filtered off and evaporated in vacuo to give 510 mg of yellow oil. This oil was purified by preparative LC (Irregular SiOH 15-40 μm, 24 g Grace, mobile phase gradient: from DCM 100% to DCM 95%, MeOH 5%). The desired fractions were collected and solvent evaporated until dryness to give 58 mg of colorless oil (impure) and 369 mg of yellow oil which was dissolved in DCM and a 3N aqueous solution of HCl was added. The mixture was stirred for 96 h then basified with a saturated aqueous solution of NaHCO$_3$ and extracted with DCM. The organic layer was separated, dried over MgSO$_4$, filtered off and evaporated in vacuo to give 234 mg of pale yellow oil which was triturated in Et$_2$O. The precipitate was filtered on a glass frit and the solid was dried under high vacuum at 50° C. for 2 h to give 175 mg of Compound 21, yellow solid (45%). m.p.=147° C. (dsc).

Example A22: Preparation of Co. 22

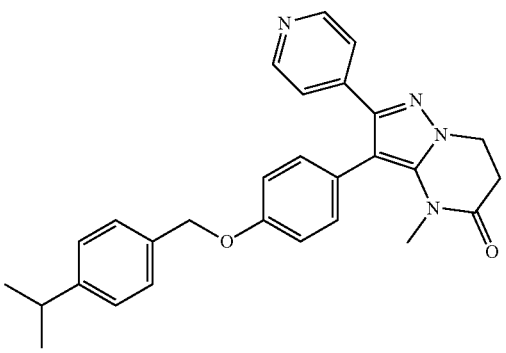 [SMILES: CC(C)c1ccc(COc2ccc(-c3c(-c4ccncc4)nn4c3N(C)C(=O)CC4)cc2)cc1]

To a solution of Compound 16 (300 mg, 0.684 mmol) in DMF (5 mL) was added silver(I) oxide (160 mg, 0.684 mmol) and MeI (44.8 μL, 0.718 mmol). The reaction was stirred for 5 h at r.t. and diluted with DCM. The crude was filtered on a pad of silica and washed with DCM (25 mL) and 10% MeOH in DCM (25 mL). The filtrate was evaporated to dryness to afford 320 mg of a residue which was purified by preparative LC (Regular SiOH 50 μm, 24 g Grace, dry loading, mobile phase gradient: from DCM 100% to DCM 90%, Methanol 10%). The pure fractions were collected and solvent evaporated until dryness. The product was triturated in Et$_2$O, filtered-off and dried to give 92 mg of Compound 22, white powder (30%). m.p.=160° C. (dsc).

Example A23: Preparation of Co. 23 Co. C and Co. D a—Synthesis of Intermediate 53:

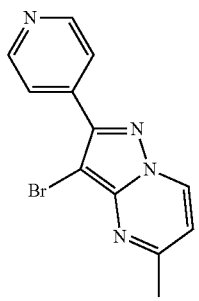 [SMILES: Cc1ccn2nc(-c3ccncc3)c(Br)c2n1]

A solution of 9 (730 mg, 3.05 mmol) and acetylacetaldehydedimethyl acetate (807 µL, 6.11 mmol) in EtOH (15 mL) and acetic acid (175 µL, 3.05 mmol) was stirred at 50° C. for 17 h. The r.m. was concentrated and filtered on a glass frit. The solid was washed with Et₂O to give 650 mg of intermediate 53, white solid (74%).

b—Synthesis of Co. C (Co. of Formula (I')):

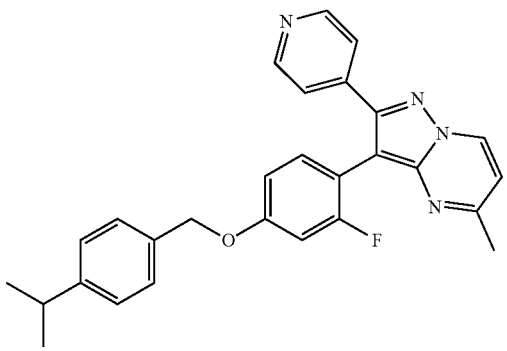 [SMILES: Cc1ccn2nc(-c3ccncc3)c(-c3ccc(OCc4ccc(C(C)C)cc4)cc3F)c2n1]

A solution of 53 (625 mg, 2.16 mmol) and 18 (1.20 g, 3.24 mmol) in 1,4-dioxane (8 mL) and H₂O (4 mL) was treated with K₃PO₄ (1.15 g, 5.40 mmol) and purged with N₂. PdCl₂(dppf)₂ (142 mg, 173 µmol) was then added and the r.m. was carefully purged with N₂. The mixture was heated at 120° C. using one single mode microwave (Biotage Initiator EXP 60) with a power output ranging from 0 to 400 W for 25 minutes [fixed hold time]. The crude mixture was diluted in DCM and water. The organic layer was separated, dried over MgSO₄ and evaporated in vacuo to give a residue. The residue was purified by preparative LC (irregular SiOH 15-40 µm, 50 g, Merck, mobile phase gradient: from DCM 100% to DCM 95%, MeOH 5%). The pure fractions were collected and solvent evaporated until dryness to give 550 mg of Compound C, beige solid (56%).

c—Synthesis of Co. D (Co. of Formula (I')):

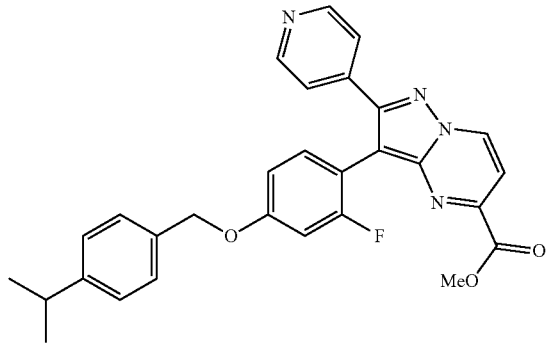 [SMILES: COC(=O)c1ccn2nc(-c3ccncc3)c(-c3ccc(OCc4ccc(C(C)C)cc4)cc3F)c2n1]

A solution of Compound C (550 mg, 1.22 mmol) in 1,4-dioxane (25 mL) was treated with selenium dioxide (405 mg, 3.65 mmol) and stirred at 80° C. for 17 h. The r.m. was then filtered and evaporated in vacuo to give 640 mg of brown solid. This solid was dissolved in MeOH (15 mL) and treated with H₂SO₄ (2 6 µL, 0.486 mmol). The r.m. was stirred at 80° C. for 4 h. The r.m. was diluted with DCM, washed with a saturated solution of NaHCO₃, dried over MgSO₄ and evaporated in vacuo to give 580 mg of Compound D, yellow solid (96%).

d—Synthesis of Co. 23

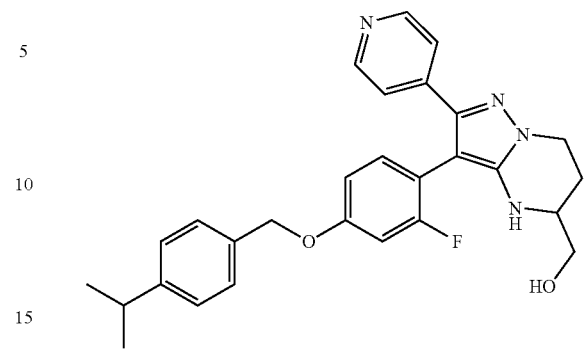

To a solution of Compound D (580 mg, 1.17 mmol) in THF (10 mL) and MeOH (10 mL) in a sealed tube were added calcium chloride (519 mg, 4.67 mmol) and NaBH₄ (354 mg, 9.35 mmol). The mixture was heated at 80° C. for 5 minutes. After cooling down to r.t., water and DCM were added. The organic layer was separated, dried over MgSO₄, filtered off and evaporated in vacuo to give a yellow oil. This oil was purified by preparative LC (irregular SiOH 15-40 µm, 80 g, Grace, mobile phase gradient: from DCM 100% to DCM 92%, MeOH 8%). The pure fractions were collected and solvent evaporated until dryness to give 195 mg of Compound 23, white solid (35%).

Example A24: Preparation of Co. 24, Co. E, Co. F and Co. G a—Synthesis of Co. E (Co. of Formula (I')):

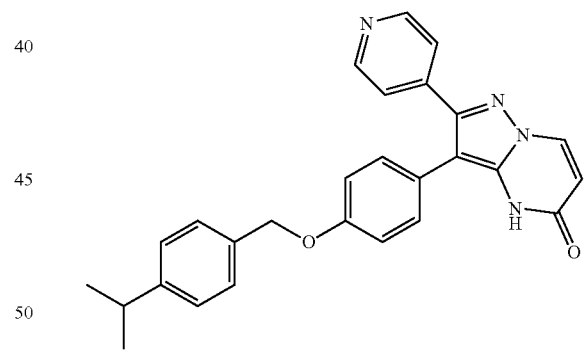

To a suspension of 4 (100 mg, 0.26 mmol) and 1,3-dimethyluracil (104 mg, 0.742 mmol) in 2-methyl-2-butanol (2.5 mL) was added sodium ethoxide (0.253 mL, 0.78 mmol). The reaction was heated at 110° C. overnight and cooled down to r.t. Water was added to the mixture and the aqueous layer was extracted with DCM. The combined organic layers were washed with saturated NaHCO₃, brine, dried over MgSO₄ and evaporated in vacuo to afford 120 mg. The residue was purified by preparative LC (Regular SiOH 50 µm, 30 g Merck, liquid loading, mobile phase gradient: from DCM 100% to DCM 90%, MeOH 10%). The pure fractions were collected and solvent evaporated until dryness to give 80 mg of Compound E, beige powder (70%). m.p.=243° C. (dsc).

b—Synthesis of Co. F (Co. of Formula (I')):

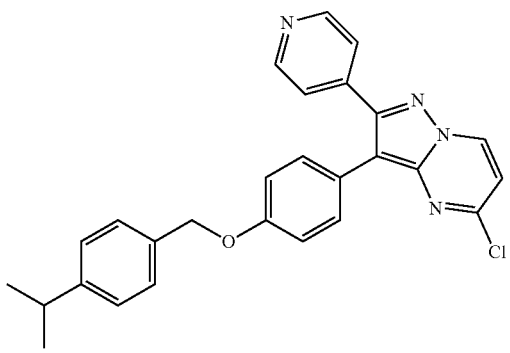 [SMILES: CC(C)c1ccc(COc2ccc(-c3c(-c4ccncc4)nn4ccc(Cl)nc34)cc2)cc1]

To a suspension of Compound E (1.31 g, 3.00 mmol) in DCE (30 mL) were added $SOCl_2$ (2.18 mL, 30.0 mmol) and DMF (0.232 mL, 3.00 mmol). The r.m. was stirred at 100° C. overnight, cooled down to r.t. and evaporated in vacuo. The residue was co-evaporated with toluene (3 times) to afford orange solid which was triturated in $Et_2O$ and filtered off to afford 1.21 g of Compound F, orange solid (88%).

c—Synthesis of Co. G (Co. of Formula (I')):

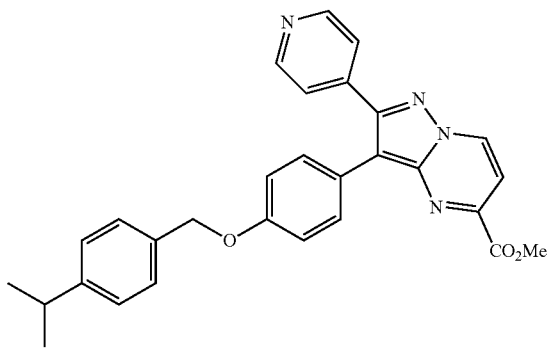 [SMILES: COC(=O)c1ccn2nc(-c3ccncc3)c(-c3ccc(OCc4ccc(C(C)C)cc4)cc3)c2n1]

To a mixture of Compound F (1.20 g, 2.64 mmol) and $Et_3N$ (1.47 mL, 10.6 mmol) in MeOH (45 mL) in a steel sealed reactor were added $Pd(OAc)_2$ (29.6 mg, 0.132 mmol) and 1,2-bis(diphenylphosphino)ethane (105 mg, 0.264 mmol). The reactor was carefully closed and purged with CO (3 times). The reaction was then stirred at 100° C. overnight under CO atmosphere (100 psi). The reaction was cooled down to r.t., diluted with DCM and filtered on a pad of silica. Silica was added to the filtrate and the mixture was evaporated in vacuo to give a residue. The residue was purified by preparative LC (Irregular SiOH 15-40 µm, 120 g Grace, solid deposit, mobile phase gradient: from heptane 50%, EtOAc 50% to heptane 30%, EtOAc 70%). The pure fractions were collected and solvent evaporated until dryness to give 1.00 g of Compound G, orange solid (79%).

d—Synthesis of Co. 24:

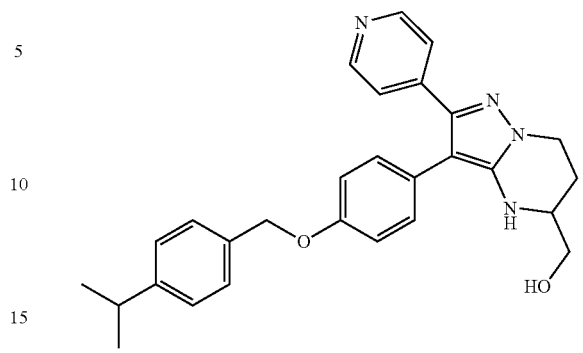

To a solution of Compound G (300 mg, 0.627 mmol) in dry THF (6 mL) and dry MeOH (6 mL) in a sealed tube were added calcium chloride (278 mg, 2.51 mmol) and $NaBH_4$ (190 mg, 5.02 mmol). The mixture was heated at 110° C. for 5 min. After cooling down to r.t., water was added and the solvent was removed in vacuo. DCM was added to the residue and the organic layer was separated, dried over $MgSO_4$, filtered off and evaporated in vacuo to give 434 mg of a yellow oil. This oil was purified by preparative LC (Irregular SiOH 15-40 µm, 12 g Grace, mobile phase gradient: from DCM 100% to DCM 90%, iPrOH 10%). The desired fractions were collected and solvent evaporated until dryness to give 316 mg of a white solid. This solid was put into a vial and recrystallized in a minimum of MeOH. After cooling, the solid obtained was dried in vacuo (50° C.) for 2 h to give 269 mg of a white solid. This solid was recrystallized from ACN. The precipitate was filtered on a glass frit and the filtrate was evaporated in vacuo. The recrystallization was repeated once. The solid was dried in high vacuum at 55° C. for 3 h to give 165 mg of Compound 24, white solid (58%). m.p.=199° C. (DSC).

Example A25: Preparation of Co. 25 and Co. H a—Synthesis of Co. H (Co. of Formula (I')):

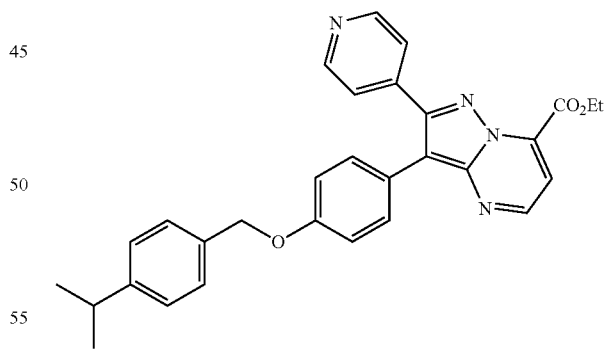

A mixture of ethyl pyruvate (0.173 mL, 1.56 mmol) and N,N-dimethylformamide dimethyl acetate (0.207 mL, 1.56 mmol) was heated at 100° C. for 30 min. Then, the mixture was cooled down to r.t. and acetic acid (5 mL) and 4 (500 mg, 1.30 mmol) were added and the reaction was heated at 100° C. for 1 h. The solvents were evaporated in vacuo and the residue was co-evaporated with toluene (3 times). The crude was taken-up in DCM and washed with a saturated solution of $NaHCO_3$, brine, dried over $MgSO_4$ and evaporated in vacuo to afford 365 mg of dark yellow oil. The residue was purified by preparative LC (Regular SiOH 50 µm, 24 g Grace, liquid loading, mobile phase gradient: from DCM 100% to DCM 60%, EtOAc 40%). The pure fractions were collected and the solvent evaporated until dryness to give 140 mg of Compound H, orange powder (22%). m.p.=128° C. and 140° C. polymorph (DSC).

b—Synthesis of Co. 25

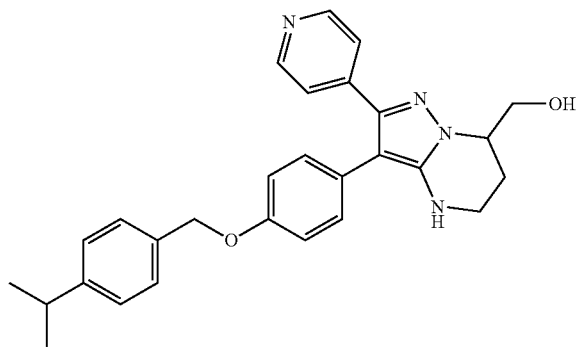 [SMILES: CC(C)c1ccc(COc2ccc(-c3c(-c4ccncc4)nn4c3NCCC4CO)cc2)cc1]

To a suspension of Compound H (110 mg, 0.223 mmol) in EtOH (4 mL) was added NaBH₄ (16.9 mg, 0.447 mmol). The reaction was heated at 80° C. for 1 h and cooled down to r.t. Water was added and the mixture was evaporated to dryness. Then, the residue was taken-up in DCM, washed with water, dried over MgSO₄ and evaporated in vacuo to afford 152 mg of a beige solid. The crude material was combined with another batch (with 30 mg of Compound H as reactant in the same conditions) and was purified by preparative LC (Irregular SiOH 15-40 µm, 24 g Grace Resolv, mobile phase gradient: from DCM 100% to DCM 90%, MeOH 10%). The pure fractions were collected and solvent evaporated until dryness to give 60 mg of Compound 25, pale beige solid (46%). m.p.=155° C. (dsc).

Example A26: Preparation of Co. 26 and Co. J a—Synthesis of Co. J (Co. of Formula (I')):

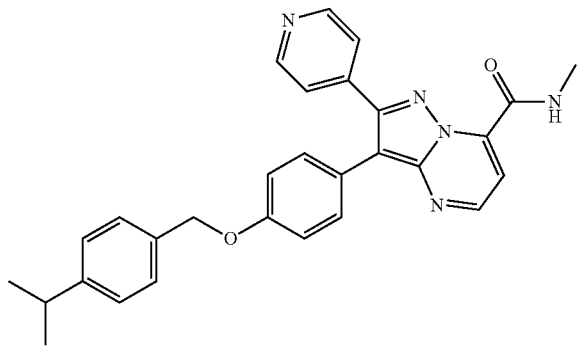 [SMILES: CNC(=O)c1ccnc2c(-c3ccc(OCc4ccc(C(C)C)cc4)cc3)c(-c3ccncc3)nn12]

A mixture of Compound H (386 mg, 0.807 mmol) in methylamine in 2M THF (8.07 mL, 16.1 mmol) was heated at 120° C. using one single mode microwave (Biotage Initiator EXP 60) with a power output ranging from 0 to 400 W for 1 h [fixed hold time]. After cooling down to r.t., the mixture was evaporated to dryness to afford 380 mg of dark orange oil. The crude mixture was purified by preparative LC (Regular SiOH 50 µm, 24 g Grace, solid sample, mobile phase: DCM 100% to DCM 90%, MeOH 10%). The pure fractions were collected and solvent evaporated until dryness to give 159 mg of yellow solid (41%). This solid was triturated in Et₂O filtered off and dried to give 101 mg of Compound J, yellow solid (26%). M.p.=207° C. (dsc).

b—Synthesis of Compound 26

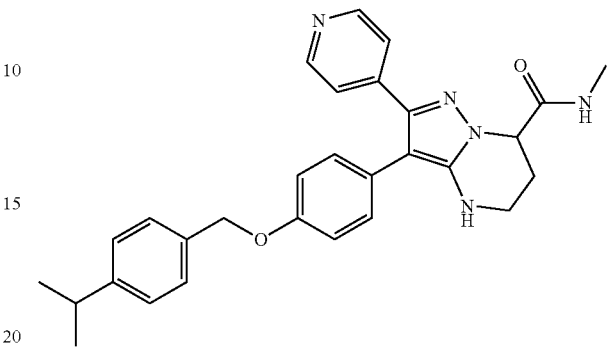

To a suspension of Compound J (86 mg, 0.18 mmol) in EtOH (2 mL) was added NaBH₄ (13.6 mg, 0.36 mmol). The r.m. was stirred at 80° C. for 30 min and then cooled down to r.t. The mixture was quenched with water and evaporated to dryness under reduced pressure. The crude mixture was taken-up in DCM and washed with water, a saturated solution of NaCl, dried over MgSO₄ and evaporated in vacuo. The oil was taken-up in Et₂O and heptane. The solution was evaporated in vacuo to afford 86 mg of Compound 26, pale beige solid (99%).

Example A27: Preparation of Co. 27

To a solution of Compound 26 (343 mg, 0.712 mmol) in dry THF (8.5 mL) under N₂ was added BH₃.THF (3.56 mL, 3.56 mmol). The reaction was stirred at 70° C. for 3 h and cooled down to r.t. Then, MeOH and 3N HCl were carefully added and the mixture was stirred overnight. A 10% solution of K₂CO₃ was added until pH 9. After evaporation of the solvents, the residue was taken-up in water and DCM. The aqueous layer was extracted with DCM (3 times). The combined organic layers were washed with brine, dried over MgSO₄, filtered off and evaporated in vacuo to give 336 mg of yellow solid. The residue was purified by preparative LC (Regular SiOH 50 µm, 12 g Grace, solid loading, mobile phase: DCM 100% to DCM 80%, MeOH 20%). The desired fractions were collected and solvent evaporated until dryness to give 67 mg of off-white solid. The solid was purified by Reverse phase (Stationary phase: X-Bridge-C18 5 µm 30*150 mm, Mobile phase Gradient: from 70% HCOONH₄ 0.5% w/w aqueous solution (pH=4.5), 30% ACN to 100% ACN). The pure fractions were collected and solvent evaporated until dryness to give 15 mg of Compound 27 (0.8 HCOOH) as a beige solid (4%).

The compounds listed in Table 1 below have been prepared. The values of salt stoichiometry or acid content in the compounds as provided herein, are those obtained experimentally and may vary dependent on the analytical method used (for compound 27, ¹H NMR was used). In case no salt form is indicated, the compound was obtained as a free base. Salt forms of the free bases can easily be obtained by using typical procedures known to those skilled in the art.

TABLE 1

Compounds

Compound 1; Method A1

Compound 6; Method A6

Compound 2; Method A2

Compound 7; Method A7

Compound 3; Method A3

Compound 8; Method A8

TABLE 1-continued
Compounds
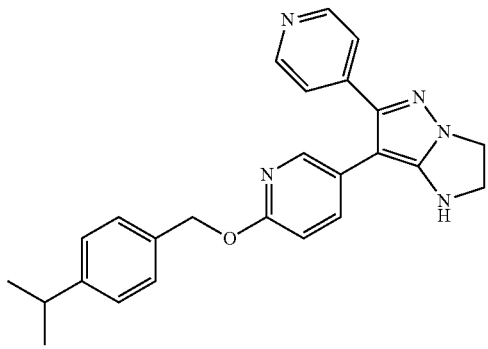 [SMILES: CC(C)c1ccc(COc2ccc(-c3c(-c4ccncc4)nn4c3NCC4)cn2)cc1]
Compound 4; Method A4
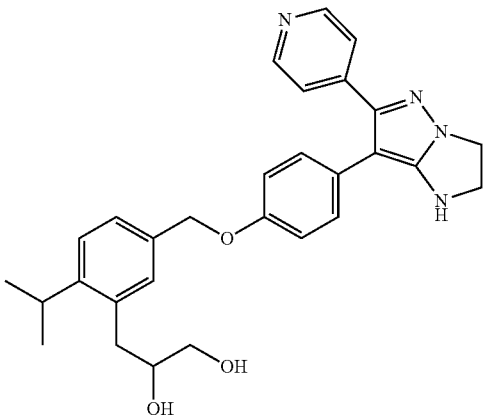 [SMILES: CC(C)c1ccc(COc2ccc(-c3c(-c4ccncc4)nn4c3NCC4)cc2)cc1CC(O)CO]
Compound 9; Method A9
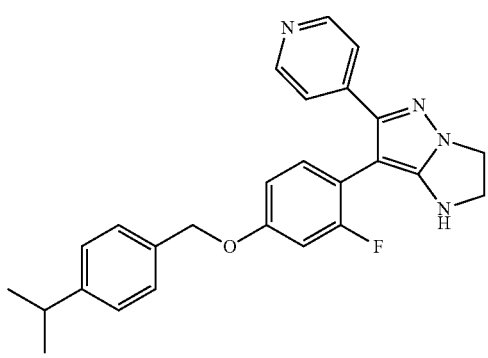 [SMILES: CC(C)c1ccc(COc2ccc(-c3c(-c4ccncc4)nn4c3NCC4)c(F)c2)cc1]
Compound 5; Method A5
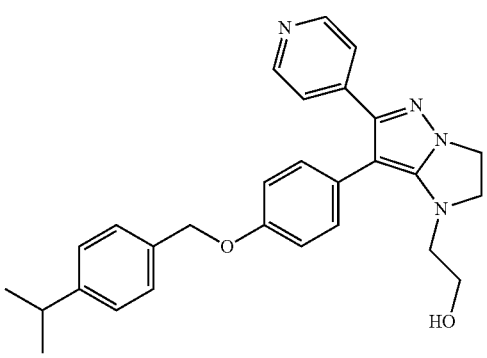 [SMILES: CC(C)c1ccc(COc2ccc(-c3c(-c4ccncc4)nn4c3N(CCO)CC4)cc2)cc1]
Compound 10; Method A10
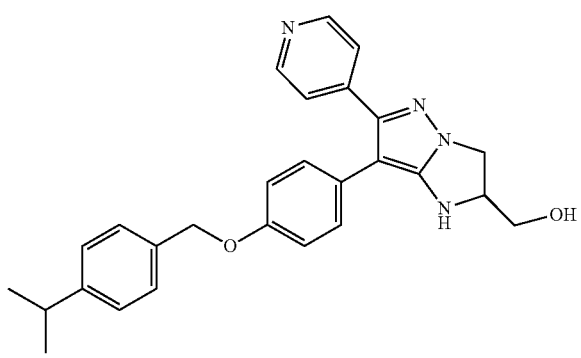 [SMILES: CC(C)c1ccc(COc2ccc(-c3c(-c4ccncc4)nn4c3NC(CO)C4)cc2)cc1]
Compound 11; Method A11
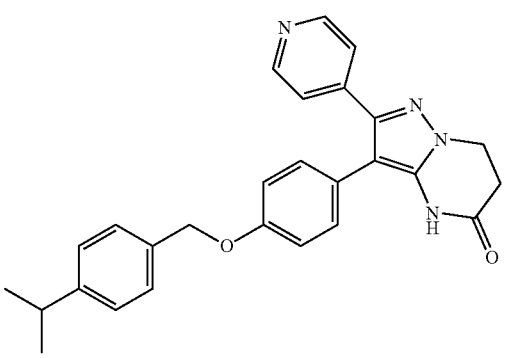 [SMILES: CC(C)c1ccc(COc2ccc(-c3c(-c4ccncc4)nn4c3NC(=O)CC4)cc2)cc1]
Compound 16; Method A16

TABLE 1-continued
Compounds
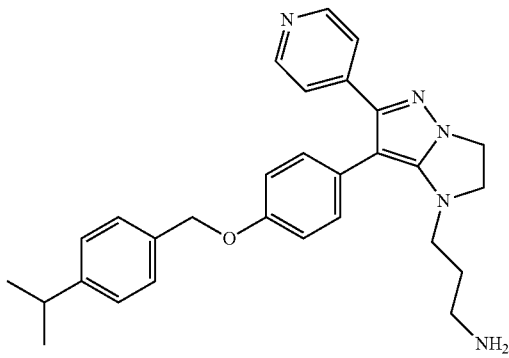 [SMILES: CC(C)c1ccc(COc2ccc(-c3c(-c4ccncc4)nn4c3N(CCCN)CC4)cc2)cc1]
Compound 12; Method A12
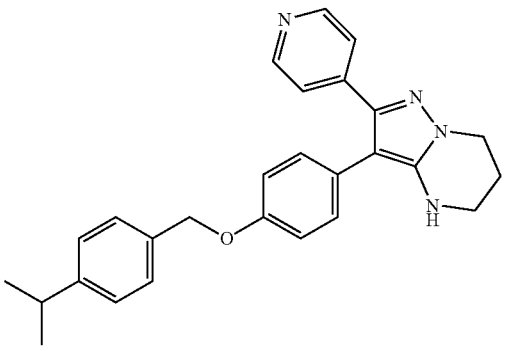 [SMILES: CC(C)c1ccc(COc2ccc(-c3c(-c4ccncc4)nn4c3NCCC4)cc2)cc1]
Compound 17; Method A17
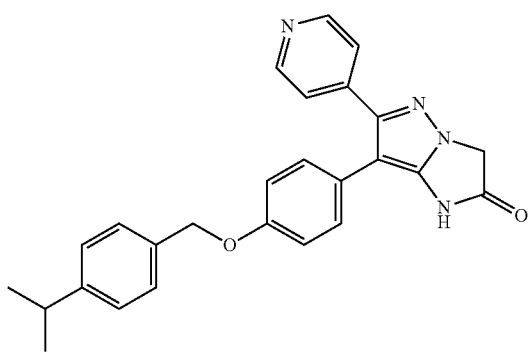 [SMILES: CC(C)c1ccc(COc2ccc(-c3c(-c4ccncc4)nn4c3NC(=O)C4)cc2)cc1]
Compound 13; Method A13
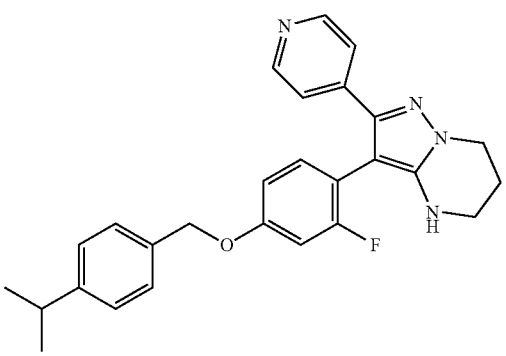 [SMILES: CC(C)c1ccc(COc2ccc(-c3c(-c4ccncc4)nn4c3NCCC4)c(F)c2)cc1]
Compound 18; Method A18
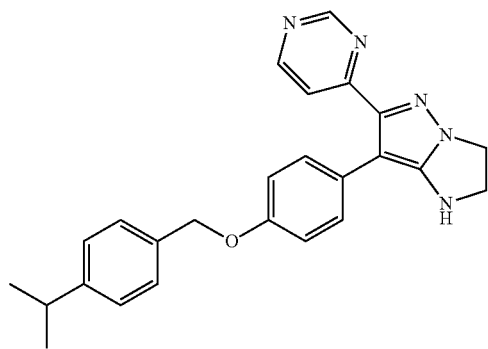 [SMILES: CC(C)c1ccc(COc2ccc(-c3c(-c4ccncn4)nn4c3NCC4)cc2)cc1]
Compound 14; Method A14
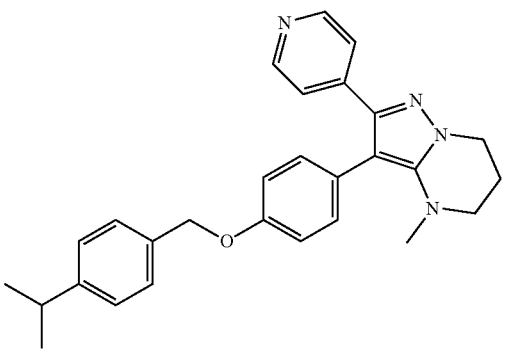 [SMILES: CC(C)c1ccc(COc2ccc(-c3c(-c4ccncc4)nn4c3N(C)CCC4)cc2)cc1]
Compound 19; Method A19
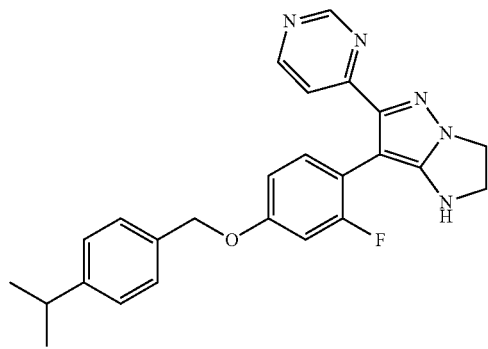 [SMILES: CC(C)c1ccc(COc2ccc(-c3c(-c4ccncn4)nn4c3NCC4)c(F)c2)cc1]
Compound 15; Method A15
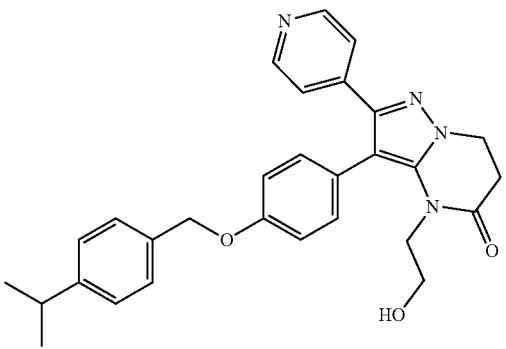 [SMILES: CC(C)c1ccc(COc2ccc(-c3c(-c4ccncc4)nn4c3N(CCO)C(=O)CC4)cc2)cc1]
Compound 20; Method A20

TABLE 1-continued
Compounds
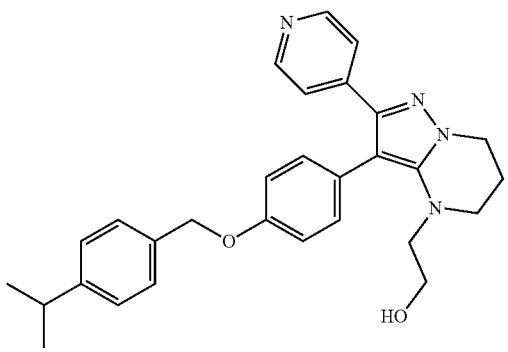 [SMILES: CC(C)c1ccc(COc2ccc(-c3c(-c4ccncc4)nn4c3N(CCO)CCC4)cc2)cc1]
Compound 21; Method A21
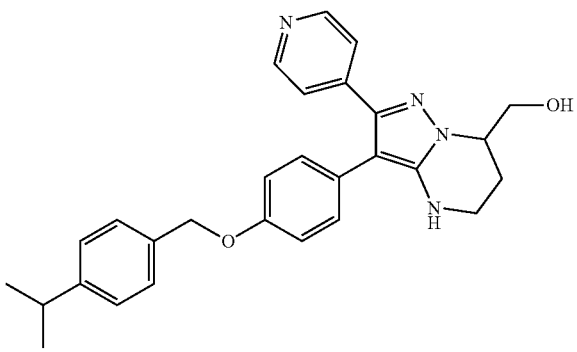 [SMILES: CC(C)c1ccc(COc2ccc(-c3c(-c4ccncc4)nn4c3NCCC4CO)cc2)cc1]
Compound 25; Method A25
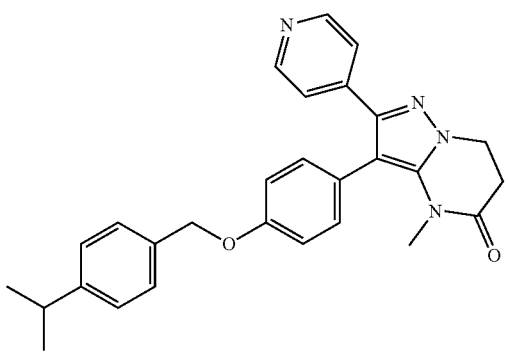 [SMILES: CC(C)c1ccc(COc2ccc(-c3c(-c4ccncc4)nn4c3N(C)C(=O)CC4)cc2)cc1]
Compound 22; Method A22
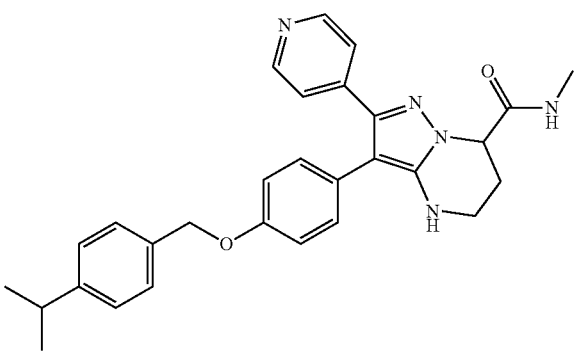 [SMILES: CNC(=O)C1CCNc2c(-c3ccc(OCc4ccc(C(C)C)cc4)cc3)c(-c3ccncc3)nn21]
Compound 26; Method A26
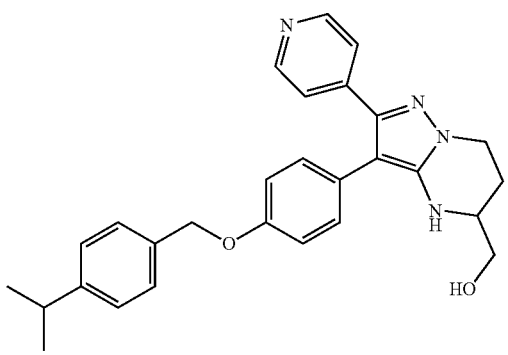 [SMILES: CC(C)c1ccc(COc2ccc(-c3c(-c4ccncc4)nn4c3NC(CO)CC4)cc2)cc1]
Compound 24; Method A24
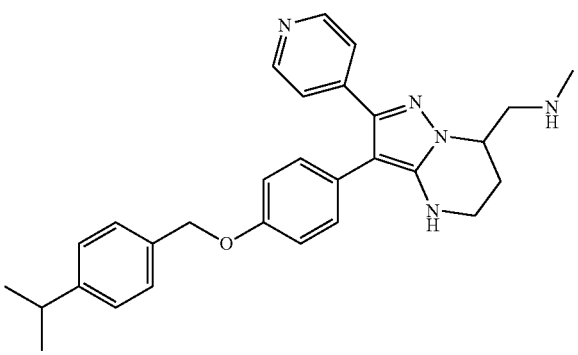 [SMILES: CNCC1CCNc2c(-c3ccc(OCc4ccc(C(C)C)cc4)cc3)c(-c3ccncc3)nn21]
Compound 27; Method A27
0.8 HCOOH
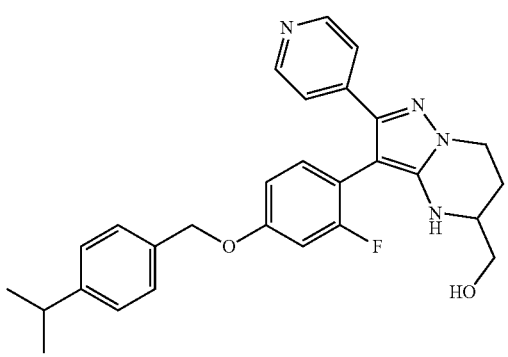 [SMILES: CC(C)c1ccc(COc2ccc(-c3c(-c4ccncc4)nn4c3NC(CO)CC4)c(F)c2)cc1]
Compound 23; Method A23
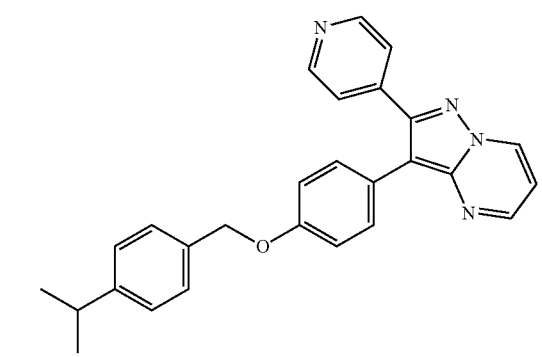 [SMILES: CC(C)c1ccc(COc2ccc(-c3c(-c4ccncc4)nn4cccnc34)cc2)cc1]
Compound A (Compound of formula I');
Method A17

TABLE 1-continued
Compounds
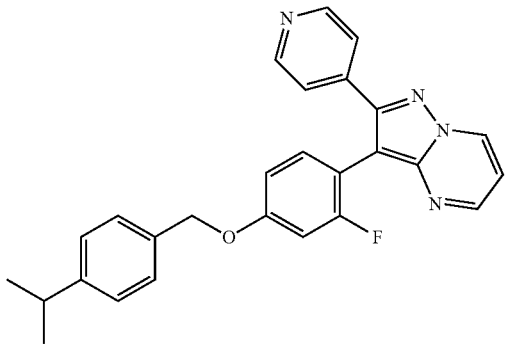 [SMILES: CC(C)c1ccc(COc2ccc(-c3c(-c4ccncc4)nn4cccnc34)c(F)c2)cc1]
Compound B (Compound of formula I');
Method A18
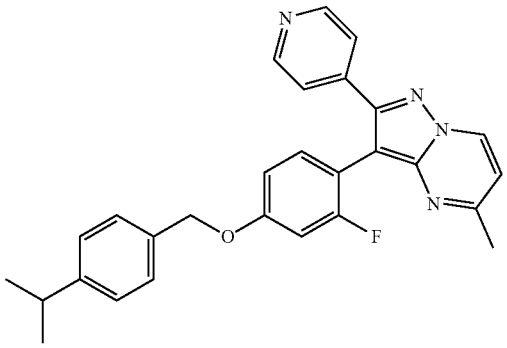 [SMILES: Cc1ccn2nc(-c3ccncc3)c(-c3ccc(OCc4ccc(C(C)C)cc4)cc3F)c2n1]
Compound C (Compound of formula I');
Method A23
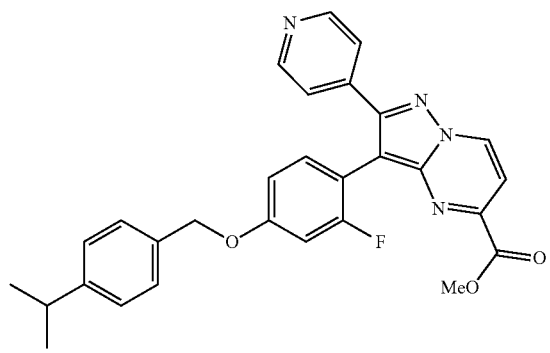 [SMILES: COC(=O)c1ccn2nc(-c3ccncc3)c(-c3ccc(OCc4ccc(C(C)C)cc4)cc3F)c2n1]
Compound D (Compound of formula I');
Method A23
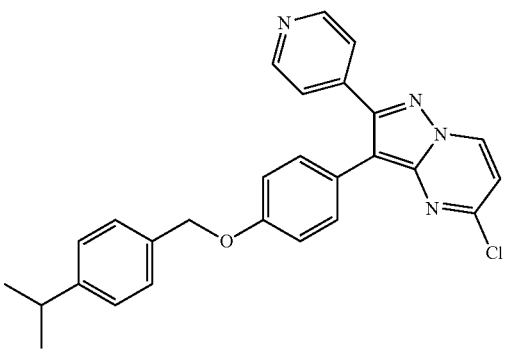 [SMILES: CC(C)c1ccc(COc2ccc(-c3c(-c4ccncc4)nn4ccc(Cl)nc34)cc2)cc1]
Compound F (Compound of formula I');
Method A24
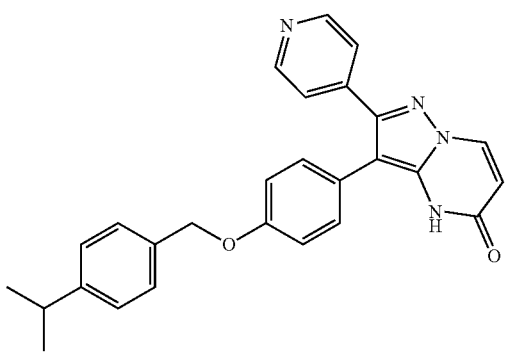 [SMILES: CC(C)c1ccc(COc2ccc(-c3c(-c4ccncc4)nn4ccc(=O)[nH]c34)cc2)cc1]
Compound E (Compound of formula I');
Method A24
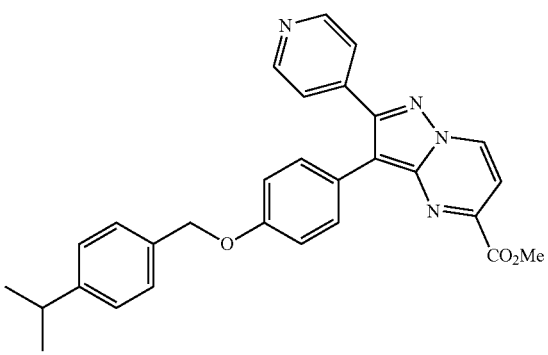 [SMILES: COC(=O)c1ccn2nc(-c3ccncc3)c(-c3ccc(OCc4ccc(C(C)C)cc4)cc3)c2n1]
Compound G (Compound of formula I');
Method A24

TABLE 1-continued

Compounds

Compound H (Compound of formula I');
Method A25

Compound J (Compound of formula I');
Method A26

Compound 28; Method A9

Analytical Part
LCMS (Liquid Chromatography/Mass Spectrometry)
LCMS General Procedure The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]+ (protonated molecule) and/or [M−H]− (deprotonated molecule). In case the compound was not directly ionizable the type of adduct is specified (i.e. [M+NH4]+, [M+HCOO]−, etc. . . . ). For molecules with multiple isotopic patterns (e.g. Br, Cl), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 2

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| (1) | Waters: Acquity UPLC ®- DAD and | Waters: BEH C18 (1.7 µm, 2.1 × 100 mm) | A: 95% CH3COONH4 7 mM/5% CH3CN, B: | 84.2% A for 0.49 min, to 10.5% A in 2.18 min, held for 1.94 min, back to | 0.343 40 | 6.2 |

TABLE 2-continued

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| (2) | Quattro Micro ™ Waters: Acquity UPLC ® H-Class - DAD and SQD 2 | Waters: BEH C18 (1.7 µm, 2.1 × 100 mm) | $CH_3CN$ A: 95% $CH_3COONH_4$ 7 mM/5% $CH_3CN$, B: $CH_3CN$ | 84.2% A in 0.73 min, held for 0.73 min. 84.2% A for 0.49 min, to 10.5% A in 1.81 min, held for 2.31 min, back to 84.2% A in 0.73 min, held for 0.73 min. | 0.343 40 | 6.1 |
| (3) | Waters: Acquity UPLC ® H-Class - DAD and SQD 2 | Macherey Nagel: Nucleoshell ® RP18 (2.7 µm, 3 × 50 mm) | A: 95% $CH_3COONH_4$ 7 mM/5% $CH_3CN$, B: $CH_3CN$ | 95% A for 0.25 min, to 5% A in 0.75 min, held for 1.9 min, back to 95% A in 0.3 min, held for 0.3 min. | 0.6 40 | 3.5 |

Melting Points

For a number of compounds, melting points (m.p.) were determined with a DSC 1 STAR$^e$ System from Mettler Toledo. Melting points were measured with a temperature gradient of 10° C./minute up to 350° C. Melting points are given by peak values.

The results of the analytical measurements are shown in table 3.

TABLE 3

Retention time ($R_t$) in min., $[M + H]^+$ peak (protonated molecule), LCMS method and m.p. (melting point in ° C.) (n.d. means not determined).

| Co. No. | $R_t$ | $[M + H]^+$ | LCMS Method | m.p. (° C.) |
|---|---|---|---|---|
| 1 | 3.16 | 411 | 1 | 156 |
| 2 | 3.18 | 447 | 1 | 153 |
| 3 | 3.1 | 436 | 1 | 191 |
| 4 | 3.06 | 412 | 1 | 159 |
| 5 | 3.19 | 429 | 1 | 141 |
| 6 | 2.94 | 436 | 1 | 158 |
| 7 | 3 | 409 | 1 | 159 |
| 8 | 3.22 | 447 | 1 | 149 |
| 9 | 2.45 | 485 | 1 | n.d. |
| 10 | 3.03 | 455 | 1 | 151 |
| 11 | 2.93 | 441 | 1 | n.d. |
| 12 | 2.63 | 468 | 1 | n.d. |
| 13 | 3.05 | 425 | 1 | 157/248 |
| 14 | 3.1 | 412 | 1 | 109 |
| 15 | 3.15 | 430 | 1 | n.d. |
| 16 | 3.03 | 439 | 1 | 290 |
| 17 | 3.29 | 425 | 1 | 205 |
| 18 | 3.77 | 443 | 2 | 188 |
| 19 | 3.59 | 439 | 1 | 120 |
| 20 | 2.96 | 483 | 1 | 205 |
| 21 | 3.08 | 469 | 1 | 147 |
| 22 | 3.31 | 453 | 1 | 160 |
| 23 | 2.99 | 473 | 1 | n.d. |
| 24 | 2.98 | 455 | 1 | 199 |
| 25 | 3.13 | 455 | 1 | 155 |
| 26 | 3.03 | 482 | 1 | n.d. |
| 27 | 3.05 | 468 | 1 | n.d. |
| A | 1.95 | 421 | 3 | n.d. |
| B | 3.5 | 439 | 1 | 187 |
| C | n.d. | n.d. | n.d. | n.d. |
| D | n.d. | n.d. | n.d. | n.d. |
| E | 3.05 | 437 | 1 | 243 |
| F | 2.08 | 455 | 3 | n.d. |
| G | n.d. | n.d. | n.d. | n.d. |
| H | 3.73 | 493 | 1 | 128/140 |
| J | 3.54 | 478 | 1 | 207 |

NMR

NMR was carried out using a Bruker Avance 500 spectrometer equipped with a reverse triple-resonance ($^1$H, $^{13}$C, $^{15}$N TXI) probe head with z gradients and operating at 500 MHz for the proton and 125 MHz for carbon, or using a Bruker 400 spectrometer equipped with a reverse resonance ($^1$H, $^{13}$C, SEI) probe head with z gradients and operating at 400 MHz for the proton.

TABLE 4

$^1$H NMR results

| Co. No. | $^1$H NMR result |
|---|---|
| 1 | (400 MHz, DMSO-$d_6$) δ ppm 8.46 (d, J = 6.1 Hz, 2H), 7.37 (d, J = 8.1 Hz, 2H), 7.33 (d, J = 6.1 Hz, 2H), 7.26 (d, J = 8.1 Hz, 2H), 7.10 (d, J = 8.6 Hz, 2H), 6.96 (d, J = 8.6 Hz, 2H), 6.02 (br. s., 1H), 5.04 (s, 2H), 4.13-4.24 (m, 2H), 3.83-3.94 (m, 2H), 2.89 (spt, J = 6.9 Hz, 1H), 1.20 (d, J = 6.9 Hz, 6H) |
| 5 | (500 MHz, DMSO-$d_6$) δ ppm 8.43 (d, J = 6.0 Hz, 2H), 7.38 (d, J = 8.2 Hz, 2H), 7.25-7.30 (m, 4H), 7.17 (t, J = 8.7 Hz, 1H), 6.93 (dd, J = 2.4, 11.8 Hz, 1H), 6.86 (dd, J = 2.4, 8.7 Hz, 1H), 5.93 (t, J = 2.5 Hz, 1H), 5.08 (s, 2H), 4.21 (t, J = 8.0 Hz, 2H), 3.85-3.92 (m, 2H), 2.90 (spt, J = 6.9 Hz, 1H), 1.20 (d, J = 6.9 Hz, 6H) |

TABLE 4-continued $^1$H NMR results

| Co. No. | $^1$H NMR result |
|---|---|
| 7 | (400 MHz, DMSO-$d_6$) δ ppm 8.46 (d, J = 5.6 Hz, 2H), 7.25-7.40 (m, 4H), 7.03-7.17 (m, 4H), 6.95 (d, J = 8.6 Hz, 2H), 6.02 (br. s., 1H), 5.03 (s, 2H), 4.13-4.25 (m, 2H), 3.84-3.95 (m, 2H), 1.85-1.98 (m, 1H), 0.88-1.00 (m, 2H), 0.61-0.72 (m, 2H) |
| 10 | (500 MHz, DMSO-$d_6$) δ ppm 8.39 (d, J = 6.3 Hz, 2H), 7.39 (d, J = 8.2 Hz, 2H), 7.28 (d, J = 8.2 Hz, 2H), 7.21 (d, J = 6.3 Hz, 2H), 7.14 (d, J = 8.8 Hz, 2H), 7.02 (d, J = 8.8 Hz, 2H), 5.05 (s, 2H), 4.69 (t, J = 5.4 Hz, 1H), 4.19 (t, J = 8.0 Hz, 2H), 3.87 (t, J = 8.0 Hz, 2H), 3.39 (q, J = 5.4 Hz, 2H), 2.87-2.95 (m, 3H), 1.21 (d, J = 6.9 Hz, 6H) |
| C | (400 MHz, DMSO-$d_6$) δ ppm 9.09 (d, J = 7.07 Hz, 1H), 8.49-8.63 (m, 2H), 7.51 (d, J = 5.56 Hz, 2H), 7.38-7.44 (m, 3H), 7.29 (d, J = 8.08 Hz, 2H), 7.07 (d, J = 7.07 Hz, 1H), 7.01 (m, 2H), 5.14 (s, 2H), 2.88-2.94 (m, 1H), 2.52 (s, 3H), 1.22 (d, J = 6.57 Hz, 6H) |
| D | (400 MHz, DMSO-$d_6$) δ ppm 9.41 (d, J = 7.58 Hz, 1H), 8.63 (d, J = 6.06 Hz, 2H), 7.65 (d, J = 7.58 Hz, 1H), 7.55 (d, J = 6.06 Hz, 2H), 7.37-7.46 (m, 3H), 7.30 (d, J = 7.58 Hz, 2H), 6.96-7.11 (m, 2H), 5.06-5.18 (m, 2H), 3.91 (s, 3H), 2.82-2.97 (m, 1H), 1.22 (d, J = 7.07 Hz, 6H) |
| G | (400 MHz, DMSO-$d_6$) δ ppm 9.36 (d, J = 7.07 Hz, 1H), 8.56-8.65 (m, 2H), 7.62 (d, J = 7.07 Hz, 1H), 7.52-7.58 (m, 2H), 7.35-7.43 (m, 4H), 7.29 (d, J = 8.08 Hz, 2H), 7.12 (d, J = 9.09 Hz, 2H), 5.12 (s, 2H), 3.92 (s, 3H), 2.84-2.96 (m, 1H), 1.22 (d, J = 7.07 Hz, 6H) |

Pharmacology

Ros1 Enzymatic Assay

Compounds were spotted onto white 384-well Proxiplate plus plates (Perkin Elmer) to which 5 µl of enzyme mix (0.5 µg/ml Ros1 enzyme, 50 mM Tris-HCl pH7.5, 1 mM EGTA, 10 mM MgCl2, 0.01% Tween-20) and 5 µl of substrate mix (6 µg/ml IRS-Tide [American Peptide Company], 20 µM ATP, 13.33 µCi/ml ATP (adenosine 5'-triphosphate) $P^{33}$, 50 mM Tris-HCl pH7.5, 1 mM EGTA (ethylene glycol-bis(2-aminoethylether)-N,N,N',N'-tetraacetic acid), 10 mM $MgCl_2$, 0.01% Tween-20) were added. After incubation for 120 minutes at room temperature, 10 µl of stop reaction buffer (5 mM EDTA, 50 µM ATP, 0.1% BSA (bovine serum albumin), 0.1% Triton X-100, 50 mM Tris-HCl pH7.5, 1 mM EGTA, 10 mM $MgCl_2$, 0.01% Tween-20) containing 2 mg/ml streptavidin coupled polystyrene imaging beads (Amersham Biosciences) was added and incubated for 15 minutes at room temperature. Plates were centrifuged for 3 minutes at 1500 rpm and signals detected in a LEADseeker imaging system (GE).

In this assay, the inhibitory effects of different compound concentrations (ranging from 10 µM to 0.3 nM) were determined and used to calculate an $IC_{50}$ (M) and $pIC_{50}$ (–log $IC_{50}$) value.

Ba/F3-Ros1 Cell Proliferation Assay

This assay was carried out with Ba/F3 cells containing three different versions of Ros1: the wild-type protein, protein with a mutation at the gatekeeper residue (L2026M), and protein with a mutation identified in a tumor from a patient that became resistant to crizotinib (Xalkori®) treatment (G2032R). Compounds were solubilized in 100% DMSO (dimethyl sulfoxide) and sprayed into polystyrene, tissue culture treated 384-well plates. A 50 µl volume of cell culture medium (phenol red free RPMI-1640, 10% FBS (fetal bovine serum), 2 mM L-Glutamine) containing 20000 Ba/F3-Ros1 cells was added to each well and the plates were placed in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader. In this assay, the inhibitory effects of different compound concentrations (ranging from 10 µM to 0.3 nM) were determined and used to calculate an $IC_{50}$ (M) and $pIC_{50}$ (–log $IC_{50}$) value.

As a counter-screen the same experiment was performed for the wild-type protein in the presence of 10 ng/ml murine IL-3.

HCC78 Cell Proliferation Assay

Approximately 1000 HCC78 non-small cell lung cancer cells in 180 µl of cell culture medium (RPMI-1640, 10% FBS, 2 mM L-Glutamine, 10 mM Hepes, 1 mM sodium pyruvate, 4.5 g/L glucose, 1.5 g/L sodium bicarbonate, 25 µg/ml Gentamycin) were seeded in each well of a 96-well polystyrene, tissue-culture treated plate and incubated at 37° C. and 5% $CO_2$. After 24 hours, compounds were diluted in cell culture medium from which 20 µl was added to the wells containing cells and incubated for 4 days at 37° C. and 5% $CO_2$. A 5 mg/ml solution of the tetrazolium dye MTT was prepared in PBS (phosphate-buffered saline) and 25 µl was added to each well. After 2 hours the medium was removed and replaced by 125 µL of 4/1 DMSO/glycine buffer (0.1M glycine, 0.1M NaCl, pH 10.5) before absorbance was determined at 538 nm. In this assay, the inhibitory effects of different compound concentrations (ranging from 10 µM to 30 nM) were determined and used to calculate an $EC_{50}$ (M) and $pEC_{50}$ (–log $EC_{50}$) value.

pROS1 Immunofluorescence Assay in HCC78 Cells

Approximately 20000 HCC78 non-small cell lung cancer cells in 180 µl of cell culture medium (RPMI-1640, 10% FBS, 2 mM L-Glutamine, 10 mM Hepes, 1 mM sodium pyruvate, 4.5 g/L glucose, 1.5 g/L sodium bicarbonate, 25 µg/ml Gentamycin) were seeded in each well of a 96-well polystyrene, poly-D-lysine coated plate and incubated at 37° C. and 5% $CO_2$. After 24 hours, compounds were diluted in cell culture medium from which 20 µl was added to the wells containing cells and incubated for 4 hours at 37° C. and 5% $CO_2$. The medium was removed and the cells were fixed by adding 100 µl of 5% formaldehyde in TBS (tris-buffered saline) (50 mM Tris.HCl, pH 7.4, 150 mM NaCl) and incubating for 15 minutes at room temperature. The formaldehyde was removed and replaced with methanol for 10 minutes at room temperature, after which the cells were washed 3 times with TBS containing 1% Triton X-100 and incubated in Odyssee (Li-Cor) blocking buffer for 1 hour at room temperature. The cells were then incubated with the primary rabbit antibody directed against Ros pY2274 (cst-3078) diluted 1/200 in blocking buffer for 24 hours at room temperature. The cells were washed three times with TBS containing 0.1% Triton X-100 and incubated with a secondary anti-rabbit antibody conjugated to the fluorescent dye Alexafluor 680 in blocking buffer for 1 hour at room temperature. The cells were washed three times with TBS containing 0.1% Triton X-100 and left to dry before measuring RFUs (Relative Fluorescence Units) at 700 nm using a fluorescence imager.

The same experiment was performed using total Ros1 antibody (sc-6347) diluted 1/1000 instead of Ros1 pY2274 antibody and an anti-goat antibody conjugated to IRDye800cw as a secondary antibody. RFUs were measured at 800 nM. The signals from total Ros1 detection were used to normalize the Ros1pY2274 values.

In this assay, the inhibitory effects of different compound concentrations (ranging from 10 μM to 3 nM) were determined and used to calculate an $IC_{50}$ (M) and $pIC_{50}$ ($-\log IC_{50}$) value.

The results of the above in vitro test are shown in table 5:

Efficacy Studies in Mice Bearing Ba/F3-Ros1 Tumors

Approximately $2\times10^6$ Ba/F3 cells containing either wild-type or L2026M mutant Ros1 are inoculated into the inguinal region of NMRI nude mice. When the resulting tumors reach a size of 250 to 350 mm$^3$, mice are randomly assigned to the different treatment groups (8 to 12 mice per group). Compounds formulated in 20% cyclodextrin are administered to the mice by oral gavage at various doses for 10-days once (QD) or twice (BID) a day. Tumor sizes are determined by caliper measurement on day 1 prior to treatment and then twice weekly for the duration of the study using the commonly following formula: tumor volume (mm$^3$)=(a×b$^2$/2); where 'a' represents the length, and 'b' the width of the tumor. Treatment/control (T/C) ratios are calculated at the end of the study based on the change in final relative tumor volumes.

Approximately $2\times10^6$ Ba/F3 cells containing G2032R mutant Ros1 were inoculated into the inguinal region of NMRI nude mice. When the resulting tumors reached a size of 250 to 350 mm$^3$, mice were randomly assigned to the different treatment groups (8 to 12 mice per group). Compounds formulated in 20% cyclodextrin were administered to the mice by oral gavage at various doses for 10-days once (QD) or twice (BID) a day (see table below for administration frequency used in the study). Tumor sizes were determined by caliper measurement on day 1 prior to treatment and then twice weekly for the duration of the study using the commonly following formula: tumor volume (mm$^3$)=(a×b$^2$/2); where 'a' represents the length, and 'b' the width of the tumor. Treatment/control (T/C) ratios were calculated at the end of the study based on the change in final relative tumor volumes.

| Co. | ROS1 pIC50 | BaF3-ROS1 − IL3 pIC50 | BaF3-ROS1 + IL3 pIC50 | Ba/F3 Ros1 L2026M (-IL-3) pIC50 | Ba/3 Ros1 G2032R (-IL-3) pIC50 | HCC-78 PROL pEC50 | HCC78 pRos pIC50 |
|---|---|---|---|---|---|---|---|
| Co. 16 | 6.9 | 7.0 | <5 | 7.3 | | 7.0 | ~5.4 |
| Co. 13 | 6.8 | 6.8 | <5 | 6.7 | | 6.3 | 6.8 |
| Co. 17 | 7.4 | 7.1 | <5 | 6.9 | | 7.0 | 7.6 |
| Co. 22 | 6.3 | 6.4 | <5 | | | | |
| Co. B | 7.6 | 7.2 | <5 | | | | |
| Co. A | 7.1 | 6.8 | <5 | | | | |
| Co. 18 | 7.7 | 7.6 | <5 | 7.8 | | 6.4 | |
| Co. H | 6.3 | 5.8 | <5 | | | | |
| Co. 25 | 6.9 | 7.0 | <5 | 6.8 | | 6.1 | |
| Co. 1 | 6.9 | 7.0 | 5.3 | ~6.7 | 6.4 | 6.1 | |
| Co. E | 7.2 | 7.1 | <5 | 6.9 | | 6.3 | |
| Co. G | 6.0 | <5 | <5 | | | | |
| Co. 19 | 7.0 | 6.7 | <5 | 6.4 | | 6.1 | |
| Co. 24 | 7.2 | 7.5 | 5.1 | 7.6 | | 7.1 | |
| Co. 26 | 7.5 | 7.1 | <5 | 6.7 | | 6.8 | |
| Co. J | 6.3 | 6.8 | <5 | 6.8 | | 5.7 | |
| Co. 20 | 6.5 | 6.8 | <5 | | | | |
| Co. 10 | 6.9 | 7.1 | <5 | 6.8 | 6.4 | 5.6 | |
| Co. 21 | 7.2 | 7.4 | <5 | 6.9 | | | |
| Co. 3 | 7.2 | 7.2 | <5 | 6.6 | | | |
| Co. 6 | 6.7 | 6.7 | <5 | 6.4 | | | |
| Co. 4 | 7.0 | 7.1 | 5.9 | 7.1 | | 6.2 | |
| Co. 5 | ~6.9 | 7.1 | <5 | <5 | 6.7 | 6.1 | |
| Co. 7 | 6.6 | 6.8 | <5 | 7.5 | 6.2 | 6.2 | |
| Co. 8 | 5.8 | 6.3 | 5.4 | 7.5 | | 5.7 | |
| Co. 14 | 6.4 | 6.5 | ~5.13 | 6.6 | | 6.0 | |
| Co. 15 | 6.6 | 6.8 | <5 | <5 | | 6.2 | |
| Co. 2 | 7.6 | ~8.03 | <5 | 7.7 | | 7.9 | |
| Co. 9 | 7.2 | 7.3 | <5 | 5.5 | | 6.3 | |
| Co. 27 | 6.3 | 6.3 | ~5.2 | 5.5 | | | |
| Co. 12 | 6.3 | 6.3 | ~5.35 | 6 | | 5.8 | |
| Co. C | 7.5 | 7.5 | <5 | 7.5 | | 6.7 | |
| Co. 23 | 7.5 | 7.9 | <5 | 7.8 | | 7.0 | |
| Co. 11 | 6.6 | 7.0 | 5.6 | 6.8 | | 6.1 | |

| Tumor model | Co. | Dose (mg/kg) | administration frequency | T/C (%) | number of mice per group |
|---|---|---|---|---|---|
| Ba/F3-Ros1 G2032R | Co. 1 | 12.5 | BID | 64 | 8 |
| Ba/F3-Ros1 G2032R | Co. 1 | 25 | BID | 16 | 8 |
| Ba/F3-Ros1 G2032R | Co. 1 | 50 | BID | −18 | 8 |

Composition Examples

"Active ingredient" (a.i.) as used throughout these examples relates to a compound of Formula (I) or (I'), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:
1. A compound of Formula (I)

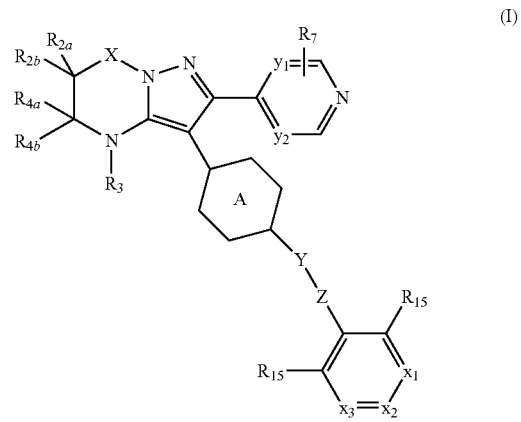

a tautomer or a stereoisomeric form thereof, wherein
$y_1$ is $CR_{7a}$ or N;
$y_2$ is CH or N;
$R_{7a}$ is hydrogen, halo, trifluoromethyl or cyano;
$R_7$ is hydrogen, —$NH_2$, —$NHCH_3$, —$NH(CH_2CH_3)$, methyl, —$CH_2OH$, halo or cyano;
or when $y_1$ represents $CR_{7a}$, this $R_{7a}$ can be taken together with a $R_7$ on an adjacent carbon atom to form —CH=CH—NH— or —N=CH—NH—;
X is —$CR_1R_{1a}$— or a covalent bond;
$R_1$ is hydrogen or $C_{1-6}$alkyl;
$R_{1a}$ is hydrogen; $C_{1-6}$alkyl; mono- or polyhalo$C_{1-6}$alkyl; $C_{1-6}$alkyl substituted with one or two hydroxyl groups; $C_{1-4}$alkyl substituted with one —$NR_{9a}R_{9b}$; or —C(=O)—$NR_{9a}R_{9b}$;
$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;
$R_{2b}$ is hydrogen or $C_{1-6}$alkyl; or
$R_{2a}$ and $R_{2b}$ are taken together to form —$CH_2$—$CH_2$—, —$CH_2$—$NR_{2c}$—$CH_2$—, —$CH_2$—$CH_2$—$CH_2$—, —$CH_2$—O—$CH_2$—, —$CH_2$—$CH_2$—$CH_2$—$CH_2$—, —$CH_2$—$CH_2$—$NR_{2c}$—$CH_2$— or =O;
$R_{2c}$ is hydrogen; $C_{1-4}$alkyl optionally substituted with one or two hydroxyl groups;
mono- or polyhalo$C_{1-6}$alkyl; $C_{1-6}$alkyloxy; $C_{1-6}$alkyl substituted with one cyano group;
or $C_{1-6}$alkyl substituted with one —$NR_{9a}R_{9b}$;
$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; or $C_{1-6}$alkyl substituted with one $R_{11}$;
$R_{4a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo$C_{1-6}$alkylcarbonyl-; $R_{10a}R_{10b}N$—$C_{1-6}$alkylcarbonyl-; $C_{1-6}$alkyl-O-carbonyl-;
$C_{1-6}$alkylcarbonyloxy-; $C_{1-6}$alkyl substituted with one $R_{11}$; $C_{1-6}$alkyloxy optionally substituted with one —$NR_{10a}R_{10b}$; $C_{2-6}$alkenyl; $C_{2-6}$alkynyl; hydroxy$C_{2-6}$alkenyl; hydroxy$C_{2-6}$alkynyl; $C_{1-6}$alkyloxy$C_{2-6}$alkenyl;

$C_{1-6}$alkyloxy$C_{2-6}$alkynyl; $C_{2-6}$alkenyl substituted with one —NR$_{10a}$R$_{10b}$; $C_{2-6}$alkynyl substituted with one —NR$_{10a}$R$_{10b}$; $C_{1-6}$alkyl substituted with one or two hydroxyl groups and one —NR$_{10}$R$_{10b}$; —C$_{1-6}$alkyl-C(R$_{13}$)=N—O—R$_{13}$; —S(=O)$_2$—C$_{1-6}$alkyl; —S(=O)$_2$—NR$_{9a}$R$_{9b}$;

$C_{1-6}$alkyl substituted with one —(C=O)—R$_{14}$; $C_{1-6}$alkyl substituted with one or two hydroxyl groups and one R$_{14}$; $C_{1-6}$alkyl substituted with one R$_{14}$; $C_{2-6}$alkenyl substituted with one R$_{14}$; $C_{2-6}$alkynyl substituted with one R$_{14}$; or R$_{14}$;

R$_{4b}$ is hydrogen; or

R$_{4a}$ and R$_{4b}$ are taken together to form =O;

Y is —O— or —C(=O)—;

Z is —CHR$_6$— or —CH$_2$—C≡C—;

R$_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —NR$_{9a}$R$_{9b}$; or —C(=O)—NR$_{9a}$R$_{9b}$;

Ring A is phenyl or a 6 membered saturated, partially saturated or aromatic heterocyclyl, said heterocyclyl containing one or two nitrogen atoms; wherein the phenyl or the heterocyclyl is optionally substituted with one or two R$_8$ substituents;

each R$_8$ is independently hydrogen; $C_{1-4}$alkyloxy; hydroxyl; cyano; $C_{1-4}$alkyl or halo;

or a R$_8$ substituent on an atom adjacent to the atom carrying the Y—Z substituent may be taken together with the R$_6$ substituent of Z, by which ring A together with Y—Z forms a bicycle of formula (a-1), (a-2), (a-3) or (a-4):

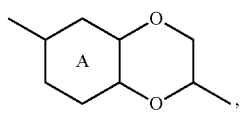 (a-1)

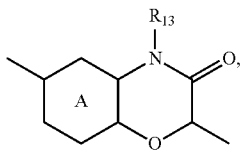 (a-2)

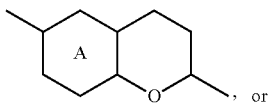 (a-3)

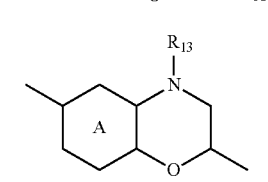 (a-4)

R$_{9a}$ and R$_{9b}$ each independently represent hydrogen; mono- or polyhalo$C_{1-4}$alkyl;

$C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;

R$_{10a}$ and R$_{10b}$ each independently represent hydrogen; $C_{1-4}$alkyl; cyano$C_{1-6}$alkyl;

$C_{1-6}$alkyl substituted with one NR$_{9a}$R$_{9b}$; $C_{1-6}$alkyl substituted with one —C(=O)—NR$_{9a}$R$_{9b}$; $C_{1-6}$alkyloxy optionally substituted with one or two hydroxyl groups;

$C_{1-6}$alkyloxy$C_{1-6}$alkyl wherein each $C_{1-6}$alkyl is optionally substituted with one or two hydroxyl groups; R$_{14}$; $C_{1-6}$alkyl substituted with one R$_{14}$; —(C=O)—R$_{14}$;

$C_{1-6}$alkylcarbonyl-; $C_{1-6}$alkyl-O-carbonyl-; mono- or polyhalo$C_{1-6}$alkylcarbonyl-substituted with one or two hydroxyl groups; mono- or polyhalo$C_{1-6}$alkyl substituted with one or two hydroxyl groups; mono- or polyhalo$C_{1-6}$alkylcarbonyl-; $C_{1-6}$alkyl substituted with one —Si(CH$_3$)$_3$; —S(=O)$_2$—C$_{1-6}$alkyl optionally substituted with one or more halo substituents; —S(=O)$_2$—NR$_{9a}$R$_{9b}$;

$C_{1-6}$alkyl substituted with one —S(=O)$_2$—C$_{1-6}$ alkyl wherein —S(=O)$_2$—C$_{1-6}$alkyl is optionally substituted with one or more halo substituents;

$C_{1-6}$alkyl substituted with one —S(=O)$_2$—NR$_{9a}$R$_{9b}$;

$C_{1-6}$alkyl substituted with one —NH—S(=O)$_2$—C$_{1-6}$alkyl wherein —NH—S(=O)$_2$—C$_{1-6}$alkyl is optionally substituted on a carbon atom with one or more halo substituents;

$C_{1-6}$alkyl substituted with one —NH—S(=O)$_2$—NR$_{9a}$R$_{9b}$;

mono- or polyhalo$C_{1-4}$alkyl; or $C_{1-4}$alkyl substituted with one or two hydroxyl groups;

R$_{11}$ is cyano; —NR$_{10a}$R$_{10b}$; $C_{1-6}$alkyloxy optionally substituted with one or two hydroxyl groups; —S(=O)$_2$—C$_{1-6}$alkyl; —S(=O)$_2$—NR$_{9a}$R$_{9b}$; —NR$_{13}$—S(=O)$_2$—C$_{1-6}$alkyl; —NR$_{13}$—S(=O)$_2$—NR$_{9a}$R$_{9b}$; $C_{1-6}$alkylcarbonyloxy-; —C(=O)—NR$_{10a}$R$_{10b}$; —O—C(=O)—NR$_{10a}$R$_{10b}$; —COOH; —P(=O)(OH)$_2$; or —P(=O)(O—C$_{1-4}$alkyl)$_2$;

R$_{12}$ is —NR$_{9a}$R$_{9b}$, $C_{1-6}$alkyloxy, or cyano;

R$_{13}$ is hydrogen or $C_{1-4}$alkyl;

R$_{14}$ is a $C_{3-8}$cycloalkyl; or a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and NR$_{9a}$R$_{9b}$;

x$_1$ is CR$_{5a}$ or N;

x$_2$ is CR$_{5b}$ or N;

x$_3$ is CR$_{5c}$ or N;

each R$_{15}$ is independently selected from the group consisting of hydrogen, methyl, halo, $C_{1-4}$alkyloxy and hydroxyl;

R$_{5a}$ and R$_{5c}$ each independently are selected from the group consisting of hydrogen;

hydroxyl; cyano; halo; $C_{1-6}$alkyl; $C_{1-6}$alkyl substituted with one or two hydroxyl groups;

mono- or polyhalo$C_{1-6}$alkyl; mono- or polyhalo$C_{1-6}$alkyloxy; $C_{1-6}$alkyl substituted with one —NR$_{9a}$R$_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups;

$C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —NR$_{9a}$R$_{9b}$; and R$_{5b}$ is hydrogen; $C_{1-6}$alkyl; $C_{3-6}$cycloalkyl optionally substituted with one cyano;

hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —Si(CH$_3$)$_3$;

$C_{1-6}$alkyl substituted with one $R_{12}$; $C_{1-6}$alkyl-O-carbonyl-; or $C_{1-6}$alkyloxy substituted with one $R_{12}$;

or a N-oxide, a pharmaceutically acceptable addition salt or a solvate thereof.

2. The compound according to claim 1, wherein $y_1$ is $CR_{7a}$ or N;
$y_2$ is CH;
$R_{7a}$ is hydrogen;
$R_7$ is hydrogen, —NH$_2$, —CH$_2$OH, halo or cyano;
or when $y_1$ represents $CR_{7a}$, this $R_{7a}$ can be taken together with a $R_7$ on an adjacent carbon atom to form —CH=CH—NH—;
X is —CR$_1$R$_{1a}$—;
$R_1$ is hydrogen or $C_{1-6}$alkyl;
$R_{1a}$ is hydrogen;
$R_{2a}$ is hydrogen; $C_{1-6}$alkyl; $C_{1-6}$alkyl substituted with one hydroxyl group; or $C_{1-6}$alkyl substituted with one substituent selected from the group consisting of —NR$_{9a}$R$_{9b}$;
$R_{2b}$ is hydrogen; or
$R_{2a}$ and $R_{2b}$ are taken together to form —CH$_2$—CH$_2$—, —CH$_2$—NR$_{2c}$—CH$_2$— or =O;
$R_{2c}$ is hydrogen; or $C_{1-6}$alkyl substituted with one —NR$_{9a}$R$_{9b}$;
$R_3$ is hydrogen; $C_{1-6}$alkyl; $C_{1-6}$alkyl substituted with one or two hydroxyl groups;
$C_{1-6}$alkyl substituted with one or two hydroxyl groups and one $C_{1-6}$alkyloxy; or
$C_{1-6}$alkyl substituted with one $R_{11}$;
$R_{4a}$ is hydrogen; $C_{1-6}$alkyl; $C_{1-6}$alkyl substituted with one hydroxyl group; or $C_{1-6}$alkyl substituted with one $R_{11}$;
$R_{4b}$ is hydrogen; or
$R_{4a}$ and $R_{4b}$ are taken together to form =O;
Y is —O— or —C(=O)—;
Z is —CHR$_6$— or —CH$_2$—C≡C—;
$R_6$ is hydrogen; $C_{1-4}$alkyl-O-carbonyl-; $C_{1-4}$alkyl; $C_{1-4}$alkyl substituted with one hydroxyl group; $C_{1-4}$alkyl substituted with one —NR$_{9a}$R$_{9b}$; or —C(=O)—NR$_{9a}$R$_{9b}$;
Ring A is phenyl or a 6-membered saturated, partially saturated or aromatic heterocyclyl, said heterocyclyl containing one or two nitrogen atoms; wherein the phenyl or the heterocyclyl is optionally substituted with one or two R$_8$ substituents;
each R$_8$ is independently hydrogen; $C_{1-4}$alkyloxy; cyano; or halo;
or a R$_8$ substituent on an atom adjacent to the atom carrying the Y—Z substituent may be taken together with the R$_6$ substituent of Z, by which ring A together with Y—Z forms a bicycle of formula (a-1a), (a-2a), (a-3a), (a-4a) or (a-4b):

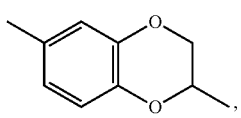
(a-1a)

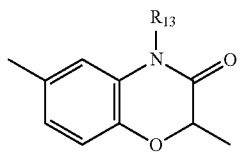
(a-2a)

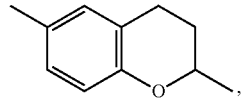
(a-3a)

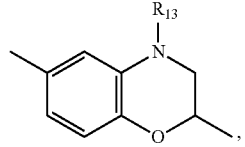
(a-4a)

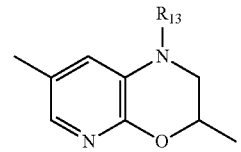
(a-4b)

$R_{9a}$ and $R_{9b}$ each independently represent hydrogen; $C_{1-4}$alkyl substituted with one hydroxyl group; or $C_{1-4}$alkyl;

$R_{10a}$ and $R_{10b}$ each independently represent hydrogen; $C_{1-4}$alkyl; $C_{1-6}$alkyl-O-carbonyl-; mono- or polyhalo$C_{1-4}$alkyl; or $C_{1-4}$alkyl substituted with one hydroxyl group;

$R_{11}$ is cyano; —NR$_{10a}$R$_{10b}$; $C_{1-6}$alkyloxy optionally substituted with one hydroxyl group; —S(=O)$_2$—O$C_{1-6}$alkyl; $C_{1-6}$alkylcarbonyloxy-; —C(=O)—NR$_{10a}$R$_{10b}$; —COOH; or —P(=O)(O—$C_{1-4}$alkyl)$_2$;

$R_{12}$ is —NR$_{9a}$R$_{9b}$, $C_{1-6}$alkyloxy, or cyano;
$R_{13}$ is hydrogen or $C_{1-4}$alkyl;
$R_{14}$ is a 5 membered saturated heterocyclyl which is optionally substituted with one, two or three substituents selected from the group consisting of oxo and $C_{1-4}$alkyl;
$x_1$ is $CR_{5a}$ or N;
$x_2$ is $CR_{5b}$;
$x_3$ is $CR_{5c}$ or N;
each $R_{15}$ is independently selected from the group consisting of hydrogen, methyl, halo, and $C_{1-4}$alkyloxy;
$R_{5a}$ and $R_{5c}$ each independently are selected from the group consisting of hydrogen;
hydroxyl; cyano; halo; $C_{1-6}$alkyl substituted with one or two hydroxyl groups; $C_{1-6}$alkyl substituted with one —NR$_{9a}$R$_{9b}$; $C_{1-6}$alkyloxy$C_{1-6}$alkyl; $C_{1-6}$alkyloxy; $C_{1-6}$alkyloxy substituted with one hydroxyl group; and $C_{1-6}$alkyloxy$C_{1-6}$alkyloxy; and
$R_{5b}$ is hydrogen; $C_{1-6}$alkyl; $C_{3-6}$cycloalkyl optionally substituted with one cyano; cyano;
mono- or polyhalo$C_{1-6}$alkyloxy; mono- or polyhalo $C_{1-6}$alkyl; $C_{1-4}$alkyl substituted with one hydroxyl group; $C_{2-6}$alkenyl; $C_{1-4}$alkyloxy; —Si(CH$_3$)$_3$; $C_{1-6}$alkyl substituted with one $R_{12}$; or $C_{1-6}$alkyl-O-carbonyl-.

3. The compound according to claim 1, wherein
$y_1$ is $CR_{7a}$ or N;
$y_2$ is CH;
$R_{7a}$ is hydrogen;
$R_7$ is hydrogen;
X is —CR$_1$R$_{1a}$— or a covalent bond;
$R_1$ is hydrogen;
$R_{1a}$ is hydrogen; $C_{1-6}$alkyl substituted with one hydroxyl group; $C_{1-6}$alkyl substituted with one —NR$_{9a}$R$_{9b}$; or —C(=O)—NR$_{9a}$R$_{9b}$;
$R_{2a}$ is hydrogen;

R$_{2b}$ is hydrogen;
R$_3$ is hydrogen; C$_{1-6}$alkyl substituted with one hydroxyl group;
R$_{4a}$ is hydrogen; C$_{1-6}$alkyl; C$_{1-6}$alkyl substituted with one hydroxyl group; or C$_{1-6}$alkyl substituted with one R$_{11}$;
R$_{4b}$ is hydrogen; or
R$_{4a}$ and R$_{4b}$ are taken together to form =O;
Y is —O—;
Z is —CHR$_6$—;
R$_6$ is hydrogen;
Ring A is phenyl or a 6 membered aromatic heterocyclyl, said heterocyclyl containing one or two nitrogen atoms; wherein the phenyl or the heterocyclyl is optionally substituted with one or two R$_8$ substituents;
each R$_8$ is independently hydrogen; cyano; or halo;
R$_{9a}$ and R$_{9b}$ each independently represent hydrogen; C$_{1-4}$alkyl;
R$_{10a}$ and R$_{10b}$ each represent hydrogen;
R$_{11}$ is —NR$_{10a}$R$_{10b}$;
x$_1$ is CR$_{5a}$; x$_2$ is CR$_{5b}$; x$_3$ is CR$_{5c}$;
each R$_{15}$ is independently selected from the group consisting of hydrogen and halo;
R$_{5a}$ and R$_{5c}$ each independently are selected from the group consisting of hydrogen;
cyano; halo; and C$_{1-6}$alkyl substituted with one or two hydroxyl groups; and
R$_{5b}$ is C$_{1-6}$alkyl or C$_{3-6}$cycloalkyl.

4. The compound according to claim 1, wherein
y$_1$ is CH; y$_2$ is CH; R$_7$ is hydrogen; X is a covalent bond; R$_{2a}$ is hydrogen; R$_{2b}$ is hydrogen;
R$_3$ is hydrogen, or C$_{1-6}$alkyl substituted with one hydroxyl group;
R$_{4a}$ is hydrogen; R$_{4b}$ is hydrogen;
Y is —O—;
Z is —CHR$_6$—; R$_6$ is hydrogen;
Ring A is phenyl optionally substituted with one R$_8$ substituent;
each R$_8$ is independently hydrogen or halo;
x$_1$ is CH; x$_2$ is CR$_{5b}$; x$_3$ is CH;
each R$_{15}$ is hydrogen; and
R$_{5b}$ is C$_{1-6}$alkyl or C$_{3-6}$cycloalkyl.

5. The compound according to claim 1, wherein
ring A is phenyl or a 6-membered saturated, partially saturated or aromatic heterocyclyl, said heterocyclyl containing one or two nitrogen atoms; wherein the phenyl or the heterocyclyl is optionally substituted with one or two R$_8$ substituents; and
each R$_8$ is independently hydrogen; C$_{1-4}$alkyloxy; hydroxyl; cyano; or halo.

6. The compound according to claim 5, wherein
ring A is phenyl or a 6-membered aromatic heterocyclyl, said heterocyclyl containing one or two nitrogen atoms; wherein the phenyl or the heterocyclyl is optionally substituted with one or two R$_8$ substituents; and
each R$_8$ is independently hydrogen; C$_{1-4}$alkyloxy; hydroxyl; cyano; or halo.

7. The compound according to claim 1, wherein R$_8$ is hydrogen.

8. The compound according to claim 1, wherein x$_1$ and x$_3$ are CH;
x$_2$ is CR$_{5b}$; and R$_{5b}$ is isopropyl.

9. The compound according to claim 1, wherein y$_1$ and y$_2$ are CH.

10. A compound of Formula (I')

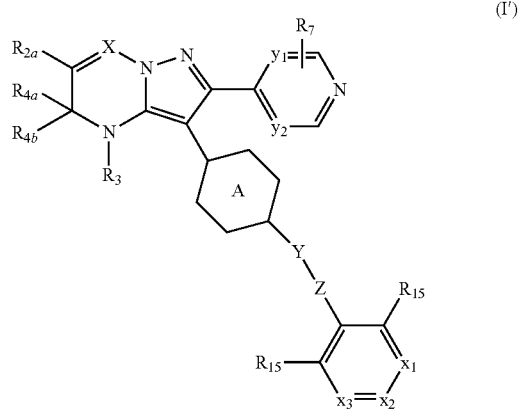

(I')

a tautomer or a stereoisomeric form thereof, wherein
y$_1$ is CR$_{7a}$ or N;
y$_2$ is CH or N;
R$_{7a}$ is hydrogen, halo, trifluoromethyl or cyano;
R$_7$ is hydrogen, —NH$_2$, —NHCH$_3$, —NH(CH$_2$CH$_3$), methyl, —CH$_2$OH, halo or cyano;
or when y$_1$ represents CR$_{7a}$, this R$_{7a}$ can be taken together with a R$_7$ on an adjacent carbon atom to form —CH=CH—NH— or —N=CH—NH—;
X is —CR$_{1a}$—;
R$_{1a}$ is hydrogen; C$_{1-6}$alkyl; mono- or polyhaloC$_{1-6}$alkyl; C$_{1-6}$alkyl substituted with one or two hydroxyl groups; C$_{1-6}$alkyl substituted with one —NR$_{9a}$R$_{9b}$; —C(=O)—NR$_{9a}$R$_{9b}$; or
C$_{1-6}$alkyl-O-carbonyl-;
R$_{2a}$ is hydrogen; C$_{1-6}$alkyl; mono- or polyhaloC$_{1-6}$alkyl; C$_{1-6}$alkyl substituted with one or two hydroxyl groups; C$_{1-6}$alkyloxycarbonyl; or C$_{1-6}$alkyl substituted with one substituent selected from the group consisting of —NR$_{9a}$R$_{9b}$, cyano and C$_{1-4}$alkyloxy;
R$_{4a}$ is hydrogen; halo; C$_{1-6}$alkyl; mono- or polyhalo C$_{1-6}$alkyl; C$_{1-6}$alkyl substituted with one or two hydroxyl groups; C$_{1-6}$alkyl substituted with one or two hydroxyl groups and one C$_{1-6}$alkyloxy; C$_{1-6}$alkylcarbonyl- optionally substituted with one or two hydroxyl groups; mono- or polyhaloC$_{1-6}$alkylcarbonyl-; R$_{10a}$R$_{10b}$N—C$_{1-6}$alkylcarbonyl-; C$_{1-6}$alkyl-O-carbonyl-; C$_{1-6}$alkylcarbonyloxy-; C$_{1-6}$alkyl substituted with one R$_{11}$; C$_{1-6}$alkyloxy optionally substituted with one —NR$_{10a}$R$_{10b}$; C$_{2-6}$alkenyl; C$_{2-6}$alkynyl;
hydroxyC$_{2-6}$alkenyl; hydroxyC$_{2-6}$alkynyl; C$_{1-6}$alkyloxyC$_{2-6}$alkenyl;
C$_{1-6}$alkyloxyC$_{2-6}$alkynyl; C$_{2-6}$alkenyl substituted with one —NR$_{10a}$R$_{10b}$; C$_{2-6}$alkynyl substituted with one —NR$_{10a}$R$_{10b}$; C$_{1-6}$alkyl substituted with one or two hydroxyl groups and one —NR$_{10}$R$_{10b}$; —C$_{1-6}$alkyl-C(R$_{13}$)=N—O—R$_{13}$; —S(=O)$_2$—C$_{1-6}$alkyl; —S(=O)$_2$—NR$_{9a}$R$_{9b}$;
C$_{1-6}$alkyl substituted with one —(C=O)—R$_{14}$; C$_{1-6}$alkyl substituted with one or two hydroxyl groups and one R$_{14}$; C$_{1-4}$alkyl substituted with one R$_{14}$; C$_{2-6}$alkenyl substituted with one R$_{14}$; C$_{2-6}$alkynyl substituted with one R$_{14}$; or R$_{14}$;
R$_{4b}$ and R$_3$ are taken together to form a bond; or
R$_{4a}$ and R$_{4b}$ together form =O, in which case R$_3$ is hydrogen; C$_{1-6}$alkyl; mono- or polyhaloC$_{1-6}$alkyl; C$_{1-6}$alkyl substituted with one or two hydroxyl groups;

$C_{1-6}$alkyl substituted with one or two hydroxyl groups and one $C_{1-6}$alkyloxy; or $C_{1-6}$alkyl substituted with one $R_{11}$;

Y is —O— or —C(=O)—;

Z is —CHR$_6$— or —CH$_2$—C≡C—;

$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —NR$_{9a}$R$_{9b}$; or —C(=O)—NR$_{9a}$R$_{9b}$;

Ring A is phenyl or a 6 membered saturated, partially saturated or aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; $C_{1-4}$alkyl or halo;

or a $R_8$ substituent on an atom adjacent to the atom carrying the Y—Z substituent is taken together with the $R_6$ substituent of Z, by which ring A together with Y—Z forms a bicycle of formula (a-1), (a-2), (a-3) or (a-4):

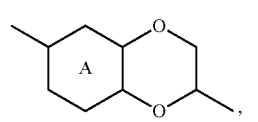
(a-1)

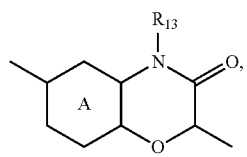
(a-2)

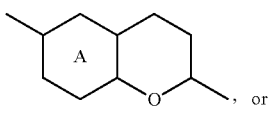
(a-3)

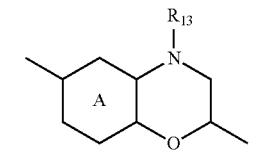
(a-4)

$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;

$R_{10a}$ and $R_{10b}$ each independently represent hydrogen; $C_{1-4}$alkyl; cyano$C_{1-4}$alkyl;

$C_{1-6}$alkyl substituted with one NR$_{9a}$R$_{9b}$; $C_{1-6}$alkyl substituted with one —C(=O)—NR$_{9a}$R$_{9b}$; $C_{1-6}$alkyloxy optionally substituted with one or two hydroxyl groups;

$C_{1-6}$alkyloxy$C_{1-6}$alkyl wherein each $C_{1-6}$alkyl is optionally substituted with one or two hydroxyl groups; $R_{14}$; $C_{1-6}$alkyl substituted with one $R_{14}$; —(C=O)—$R_{14}$;

$C_{1-6}$alkylcarbonyl-; $C_{1-6}$alkyl-O-carbonyl-; mono- or polyhalo$C_{1-6}$alkylcarbonyl- substituted with one or two hydroxyl groups; mono- or polyhalo$C_{1-6}$alkyl substituted with one or two hydroxyl groups; mono- or polyhalo$C_{1-6}$alkylcarbonyl-; $C_{1-4}$alkyl substituted with one —Si(CH$_3$)$_3$; —S(=O)$_2$—$C_{1-6}$alkyl optionally substituted with one or more halo substituents; —S(=O)$_2$—NR$_{9a}$R$_{9b}$;

$C_{1-6}$alkyl substituted with one —S(=O)$_2$—$C_{1-6}$alkyl wherein —S(=O)$_2$—$C_{1-6}$alkyl is optionally substituted with one or more halo substituents;

$C_{1-6}$alkyl substituted with one —S(=O)$_2$—NR$_{9a}$R$_{9b}$;

$C_{1-6}$alkyl substituted with one —NH—S(=O)$_2$—$C_{1-6}$alkyl wherein —NH—S(O)$_2$—$C_{1-6}$alkyl is optionally substituted on a carbon atom with one or more halo substituents;

$C_{1-6}$alkyl substituted with one —NH—S(=O)$_2$—NR$_{9a}$R$_{9b}$;

mono- or polyhalo$C_{1-4}$alkyl; or $C_{1-4}$alkyl substituted with one or two hydroxyl groups;

$R_{11}$ is cyano, —NR$_{10a}$R$_{10b}$; $C_{1-6}$alkyloxy optionally substituted with one or two hydroxyl groups; —S(=O)$_2$—$C_{1-6}$alkyl; —S(=O)$_2$—NR$_{9a}$R$_{9b}$; —NR$_{13}$—S(=O)$_2$—$C_{1-6}$alkyl; —NR$_{13}$—S(=O)$_2$—NR$_{9a}$R$_{9b}$; $C_{1-6}$alkylcarbonyloxy-; —C(=O)—NR$_{10a}$R$_{10b}$; —O—C(=O)—NR$_{10a}$R$_{10b}$; —COOH—, —P(=O)(OH)$_2$; or —P(=O)(O—$C_{1-4}$alkyl)$_2$;

$R_{12}$ is —NR$_{9a}$R$_{9b}$, $C_{1-6}$alkyloxy, or cyano;

$R_{13}$ is hydrogen or $C_{1-4}$alkyl;

$R_{14}$ is a $C_{3-8}$cycloalkyl; or a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and NR$_{9a}$R$_{9b}$;

$x_1$ is CR$_{5a}$ or N;

$x_2$ is CR$_{5b}$ or N;

$x_3$ is CR$_{5c}$ or N;

each $R_{15}$ is independently selected from the group consisting of hydrogen, methyl, halo, $C_{1-4}$alkyloxy and hydroxyl;

$R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups;

mono- or polyhalo$C_{1-6}$alkyl; mono- or polyhalo$C_{1-6}$alkyloxy; $C_{1-6}$alkyl substituted with one —NR$_{9a}$R$_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups;

$C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —NR$_{9a}$R$_{9b}$; and $R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —Si(CH$_3$)$_3$;

$C_{1-6}$alkyl substituted with one $R_{12}$; $C_{1-6}$alkyl-O-carbonyl-; or $C_{1-6}$alkyloxy substituted with one $R_{12}$;

or a N-oxide, a pharmaceutically acceptable addition salt or a solvate thereof.

11. The compound according to claim 10, wherein $y_1$ is CH; $y_2$ is CH;

$R_7$ is hydrogen;

X is —CR$_{1a}$—;

$R_{1a}$ is hydrogen; —C(=O)—NR$_{9a}$R$_{9b}$; or $C_{1-6}$alkyl-O-carbonyl-;

$R_{2a}$ is hydrogen;

$R_{4a}$ is hydrogen; halo; $C_{1-6}$alkyl; or $C_{1-6}$alkyl-O-carbonyl-;

$R_{4b}$ and $R_3$ are taken together to form a bond; or $R_{4a}$ and $R_{4b}$ together form =O, in which case $R_3$ is hydrogen;

Y is —O—; Z is —CHR$_6$—; R$_6$ is hydrogen;

Ring A is phenyl optionally substituted with one or two $R_8$ substituents;

each $R_8$ is independently hydrogen; or halo;

$R_{9a}$ and $R_{9b}$ each independently represent hydrogen; or $C_{1-4}$alkyl;

$x_1$ is $CR_{5a}$; $x_2$ is $CR_{5b}$; $x_3$ is $CR_{5c}$;

each $R_{15}$ is hydrogen;

$R_{5a}$ and $R_{5c}$ are hydrogen; and $R_{5b}$ is $C_{1-6}$alkyl.

12. A pharmaceutical composition comprising a pharmaceutically acceptable carrier and, as active ingredient, a therapeutically effective amount of a compound according to claim 1.

13. A method for the treatment of a disease or condition selected from non-small cell lung cancer, adenocarcinoma, cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer or chronic myelogenous leukemia comprising administering a compound according to claim 1 to a patient suffering from said disease or condition.

14. The method according to claim 13 wherein the disease or condition is selected from non-small-cell lung cancer, cholangiocarcinoma, and glioblastoma.

\* \* \* \* \*